(12) United States Patent
Walker et al.

(10) Patent No.: US 12,065,421 B2
(45) Date of Patent: Aug. 20, 2024

(54) INHIBITORS OF OPLOPHORUS LUCIFERASE-DERIVED BIOLUMINESCENT COMPLEXES

(71) Applicant: PROMEGA CORPORATION, Madison, WI (US)

(72) Inventors: Joel R. Walker, San Luis Obispo, CA (US); Mary Hall, Waunakee, WI (US); Christopher Todd Eggers, Madison, WI (US); Horacio Lazaro, Madison, WI (US)

(73) Assignee: Promega Corporation, Madison, WI (US)

( * ) Notice: Subject to any disclaimer, the term of this patent is extended or adjusted under 35 U.S.C. 154(b) by 136 days.

(21) Appl. No.: 17/841,613

(22) Filed: Jun. 15, 2022

(65) Prior Publication Data

US 2022/0365086 A1 Nov. 17, 2022

Related U.S. Application Data

(63) Continuation of application No. 16/428,274, filed on May 31, 2019, now Pat. No. 11,390,599.

(60) Provisional application No. 62/679,205, filed on Jun. 1, 2018.

(51) Int. Cl.
| | | |
|---|---|---|
| C07D 333/38 | (2006.01) | |
| C07C 311/21 | (2006.01) | |
| C07C 311/29 | (2006.01) | |
| C07C 317/38 | (2006.01) | |
| C07D 333/66 | (2006.01) | |
| C07D 333/78 | (2006.01) | |
| G01N 21/76 | (2006.01) | |
| G01N 33/543 | (2006.01) | |
| G01N 33/573 | (2006.01) | |

(52) U.S. Cl.
CPC .......... *C07D 333/38* (2013.01); *C07C 311/21* (2013.01); *C07C 311/29* (2013.01); *C07C 317/38* (2013.01); *C07D 333/66* (2013.01); *C07D 333/78* (2013.01); *G01N 21/763* (2013.01); *G01N 33/54306* (2013.01); *G01N 33/573* (2013.01); *C07C 2601/14* (2017.05); *C07C 2602/10* (2017.05)

(58) Field of Classification Search
CPC .. C07D 333/38; C07D 333/66; C07D 333/78; C07D 333/68; C07C 311/21; C07C 311/29; C07C 317/38; C07C 2601/14; C07C 2602/10; C07C 311/44; C07C 311/46; G01N 21/763; G01N 33/54306; G01N 33/573; G01N 33/542; G01N 33/6845; C07B 2200/07; C12Q 1/66
See application file for complete search history.

(56) References Cited

U.S. PATENT DOCUMENTS

| | | | |
|---|---|---|---|
| 8,557,970 B2 | 10/2013 | Encell et al. | |
| 8,669,103 B2 | 3/2014 | Binkowski et al. | |
| 9,797,889 B2 | 10/2017 | Dixon et al. | |
| 9,797,890 B2 | 10/2017 | Dixon et al. | |
| 2002/0193422 A1* | 12/2002 | Brendel | A61K 31/381 514/447 |
| 2008/0248511 A1 | 10/2008 | Daily et al. | |
| 2012/0107849 A1 | 5/2012 | Klaubert et al. | |
| 2012/0117667 A1 | 5/2012 | Klaubert et al. | |
| 2013/0130289 A1 | 5/2013 | Benink et al. | |
| 2015/0212078 A1 | 7/2015 | Zhou et al. | |
| 2015/0307916 A1 | 10/2015 | Zhou et al. | |
| 2017/0190675 A1 | 7/2017 | Chen et al. | |

FOREIGN PATENT DOCUMENTS

| | | |
|---|---|---|
| CA | 2 336 702 | 1/2000 |
| EP | 0 216 028 | 4/1987 |
| EP | 1 839 655 | 10/2007 |
| GB | 2 378 179 | 2/2003 |
| WO | 00/78145 | 12/2000 |
| WO | 01/87294 | 11/2001 |
| WO | 01/98264 | 12/2001 |
| WO | 02/17897 | 3/2002 |
| WO | 2003/040100 | 5/2003 |
| WO | 03/057225 | 7/2003 |
| WO | 2004/052357 | 6/2004 |
| WO | 2005/085188 | 9/2005 |
| WO | WO 2007/101225 | 9/2007 |
| WO | 2014/152895 | 9/2014 |
| WO | 2016/210294 | 12/2016 |
| WO | 2018/125992 | 7/2018 |

OTHER PUBLICATIONS

Kim, J., "Ruthenium-Catalyzed Direct C H Amidation of Arenes Including Weakly Coordinating Aromatic Ketones." Chemistry—A European Journal 19.23 (2013): 7328-7333.*

Correa, A., "Novel alternative for the N—N bond formation through a PIFA-mediated oxidative cyclization and its application to the synthesis of indazol-3-ones." The Journal of Organic Chemistry 71.9 (2006): 3501-3505.*

Kim et al., "Ruthenium-Catalyzed Direct C—H Amidation of Arenas Including Weakly Coordinating Aromatic Ketones" Chem. Eur. J. 2013, 19:7328-7333.

Mustafa et al., "Action of Grignard solutions on (a) naphthsultone, (b) tolylene-3: 4-sulphonylide, and (c) NN'-diarylsulphonyl derivatives of dianthranilide", Journal of the Chemical Society, Jan. 1, 1949, pp. 384-387.

(Continued)

*Primary Examiner* — John M Mauro
(74) *Attorney, Agent, or Firm* — Casimir Jones, S.C.; Anne M. Reynolds

(57) ABSTRACT

Compounds that may selectively inhibit *Oplophorus* luciferase-derived bioluminescent complexes, e.g., NanoBiT® bioluminescent complex, are disclosed as well as compositions and kits comprising the compounds, and methods of using the compounds.

20 Claims, 3 Drawing Sheets

Specification includes a Sequence Listing.

(56) References Cited

OTHER PUBLICATIONS

Peukert et al., "Pharmacophore-based search, synthesis, and biological evaluation of anthranilic amides as novel blockers of the Kv1.5 channel" Bioorganic & Medicinal Chemistry Letters 2004, 14: 2823-2827.
Thorne et al., "Firefly Luciferase in Chemical Biology: A Compendium of Inhibitors, Mechanistic Evaluation of Chemotypes, and Suggested Use as a Reporter" Chemistry & Biology, Aug. 24, 2012, 19: 1060-1072.
International Search Report & Written Opinion, Application No. PCT/US2019/034922, mailed Jul. 31, 2019, 22 pages.
Huggins, D J et al. "Rational Methods for the Selection of Diverse Screening Compounds" ACS Chemical Biology, vol. 6, No. 3, Mar. 18, 2011, pp. 208-217.
Kauppi, A M et al. "Inhibitors of type III secretion in Yersinia: Design, synthesis and multivariate QSAR of 2- arylsulfonylaminobenzanilides" Bioorganic & Medicinal Chemistry, vol. 15, No. 22, Sep. 26, 2007, pp. 6994-7011.
Nieland, T J F et al. "Chemical Genetic Screening Identifies Sulfonamides That Raise Organellar pH and Interfere with Membrane Traffic: Sulfonamide Inhibitors of Membrane Traffic", Traffic, vol. 5, No. 7, Jul. 1, 2004, pp. 478-492.
Kakiuchi, N et al. "Non-peptide inhibitors of HCV serine proteinase" FEBS Letters, vol. 421, No. 3, Jan. 16, 1998, pp. 217-220.
Mikhailitsyn, F S et al. "Search for novel antiparasitic agents. Communication 2. Synthesis of novel halide-containing sulphamidobenzamides and study of their acute toxicity" Meditsinkaya Parazitologiya I Parazitamnye Bolezni, No. 1, 1991, pp. 51-52.

\* cited by examiner

INHIBITORS OF OPLOPHORUS LUCIFERASE-DERIVED BIOLUMINESCENT COMPLEXES

CROSS-REFERENCE TO RELATED APPLICATIONS

This application is a continuation of U.S. patent application Ser. No. 16/428,274, which claims the priority benefit of U.S. Provisional Patent Application Ser. No. 62/679,205, filed on Jun. 1, 2018, which is incorporated herein by reference in its entirety.

TECHNICAL FIELD

The present disclosure is directed to compounds that may inhibit *Oplophorus* luciferase-derived bioluminescent complexes, in particular a bioluminescent complex of two or more non-luminescent peptide and/or polypeptide units from an *Oplophorus*-derived luciferase.

BACKGROUND

Protein fragment complementation (PFC) or enzyme fragment complementation (EFC) systems are valuable tools for monitoring co-localization and/or molecular interactions. In such systems, complementary amino acid chains, e.g., peptides or polypeptides, from a reporter molecule, e.g., a bioluminescent protein or enzyme, are fused to co-localizing and/or interacting molecules. Reporter molecules are routinely used to monitor molecular events in the fields of biology, biochemistry, immunology, cell biology, and molecular biology. Luciferases based on the luciferase secreted from the deep-sea shrimp, *Oplophorus gracilirostris*, may be used as reporter molecules and have been shown to have advantageous characteristics including broad substrate specificity, high activity, and high quantum yield. For example, non-luminescent peptides and/or polypeptides units of an *Oplophorus* luciferase variant can be fused to co-localizing/interacting molecules (e.g., proteins). When the molecules co-localize and/or interact, the non-luminescent peptide and/or polypeptide units associate to form a bioluminescent complex that, in the presence of a substrate (e.g., coelenterazine or coelenterazine derivative substrate), can generate a luminescent signal, which indicates the co-localization/interaction of the molecules. It may be further advantageous, in certain applications, to control the luminescent signal from the *Oplophorus* luciferase-derived bioluminescent complexes. Selective inhibitors for such bioluminescent complexes are useful in luminescent assays. Luciferase inhibitors may be further derivatized to provide desirable properties useful for studying enzyme activities and cellular processes.

SUMMARY

In one aspect, the disclosure provides a compound of formula (I), or a salt thereof:

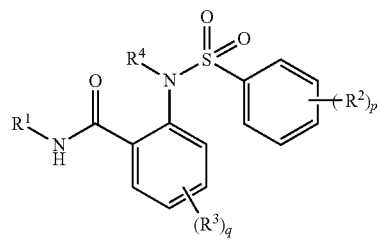

(I)

wherein:

$R^1$ is an aryl, a cycloalkyl, a heteroaryl, a heterocycle, an arylalkyl, a cycloalkylalkyl, a heteroarylalkyl, or a heterocyclylalkyl, wherein the aryl, cycloalkyl, heteroaryl, and heterocycle are optionally substituted with one or more $R^W$, wherein each $R^W$ is independently selected from the group consisting of $C_{1-10}$alkyl, $C_{1-10}$haloalkyl, halogen, —CN, —$OR^A$, —$C_{1-10}$alkylene-$OR^A$, —CO—$R^A$, —$C_{1-10}$alkylene-CO—$R^A$, —CO—$OR^A$, —$C_{1-10}$alkylene-CO—$OR^A$, —CO—$NHR^A$, —$C_{1-10}$alkylene-CO—$NHR^A$, —$NR^BR^C$, —$C_{1-10}$alkylene-$NR^BR^C$, —NH—CO—$C_{1-4}$alkyl, —$C_{1-10}$alkylene-NH—CO—$C_{1-4}$alkyl, phenyl, and phenyl substituted with 1, 2, 3, or 4 $R^D$ groups;

each $R^2$ is independently $C_{1-10}$alkyl, $C_{1-10}$haloalkyl, halogen, —CN, —$OR^A$, —$C_{1-4}$alkylene-$OR^A$, —CO—$R^A$, —$C_{1-4}$alkylene-CO—$R^A$, —CO—$OR^A$, —$C_{1-4}$alkylene-CO—$OR^A$, —CO—$NHR^A$, —$C_{1-4}$alkylene-CO—$NR^A$, —$NR^BR^C$, —$C_{1-4}$alkylene-$NR^BR^C$, —NH—CO—$C_{1-4}$alkyl, —$C_{1-4}$alkylene-NH—CO—$C_{1-4}$alkyl, phenyl, phenyl substituted with 1, 2, 3, or 4 $R^D$ groups, —C≡C—$R^A$, or —C≡$C_{1-4}$alkylene-$OR^A$, or two $R^2$ together with the carbon atoms of the

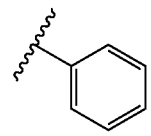 [SMILES: *c1ccccc1]

moiety to which they are attached form a 5- or 6-membered fused ring;

each $R^3$ is independently $C_{1-10}$alkyl, $C_{1-10}$haloalkyl, halogen, —CN, —$OR^A$, —$C_{1-4}$alkylene-$OR^A$, —CO—$R^A$, —CO—$OR^A$, or —CO—$NHR^A$, or two $R^3$ together with the carbon atoms of the

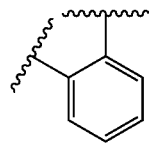 [SMILES: *c1ccccc1*]

moiety to which they are attached form a 5- or 6-membered fused ring;

$R^4$ is H or $C_{1-4}$alkyl;

p is 0, 1, 2, 3, or 4;

q is 0, 1, 2, 3, or 4;

$R^A$ at each occurrence is independently H, $C_{1-4}$alkyl, or $C_{1-4}$haloalkyl;

$R^B$ and $R^C$ at each occurrence are independently H or $C_{1-4}$alkyl, or $R^B$ and $R^C$ together with the N atom to which they are attached form a 5- or 6-membered heterocycle; and $R^D$ at each occurrence is independently $C_{1-4}$alkyl, $-OC_{1-4}$alkyl, $-CN$, or halogen.

In one aspect, the disclosure provides a method of inhibiting an *Oplophorus* luciferase-derived bioluminescent complex, the method comprising contacting the bioluminescent complex with a compound described herein.

In one aspect, the disclosure provides a method for modulating luminescence of an *Oplophorus* luciferase-derived bioluminescent complex in a sample, the method comprising,
- (a) contacting the sample with a coelenterazine substrate and a compound described herein, and
- (b) detecting luminescence in the sample,
  wherein the compound causes a decrease in the luminescence from the bioluminescent complex.

In one aspect, the disclosure provides a method to detect an interaction or co-localization between a first molecule and a second molecule in a sample, the method comprising:
- (a) contacting a sample with a coelenterazine substrate and a compound described herein, wherein the sample comprises:
  - (i) a first fusion, wherein the first fusion comprises a non-luminescent peptide of an *Oplophorus*-derived luciferase and a first molecule; and
  - (ii) a second fusion, wherein the second fusion comprises a non-luminescent polypeptide of an *Oplophorus*-derived luciferase and a second molecule, wherein the non-luminescent polypeptide is capable of forming a bioluminescent complex with the non-luminescent peptide; and
- (b) detecting luminescence in the sample,
  wherein the detection of luminescence indicates an interaction or co-localization between the first molecule and the second molecule.

In one aspect, the disclosure provides a method to detect an interaction or co-localization between a first molecule and a second molecule in a sample, the method comprising:
- (a) contacting a sample with a coelenterazine substrate and a compound described herein, wherein the sample comprises:
  - (i) a first polynucleotide encoding a first fusion, wherein the first fusion comprises a non-luminescent peptide of an *Oplophorus*-derived luciferase and a first molecule; and
  - (ii) a second polynucleotide encoding a second fusion, wherein the second fusion comprises a non-luminescent polypeptide of an *Oplophorus*-derived luciferase and a second molecule, wherein the non-luminescent polypeptide is capable of forming a bioluminescent complex with the non-luminescent peptide; and
- (b) detecting luminescence in the sample,
  wherein the detection of luminescence indicates an interaction or co-localization between the first molecule and the second molecule.

In one aspect, the disclosure provides a method to detect an interaction or co-localization of a first molecule and a second molecule in a sample, the method comprising:
- (a) contacting a sample with a non-luminescent polypeptide of an *Oplophorus*-derived luciferase, a coelenterazine substrate, and a compound described herein, wherein the sample comprises:
  - (i) a first polynucleotide encoding a first fusion, wherein the first fusion comprises an non-luminescent peptide of an *Oplophorus*-derived luciferase and a first molecule, wherein the non-luminescent peptide is capable of forming a bioluminescent complex with the non-luminescent polypeptide; and
  - (ii) a second polynucleotide encoding a second fusion, wherein the second fusion comprises a fluorescent acceptor molecule and a second molecule; and
- (b) detecting bioluminescence resonance energy transfer (BRET) in the sample indicating an interaction or co-localization of the first molecule and the second molecule.

In one aspect, the disclosure provides a method to detect an interaction or co-localization of a first molecule and a second molecule in a sample, the method comprising:
- (a) contacting a sample with a non-luminescent peptide of an *Oplophorus*-derived luciferase, a coelenterazine substrate, and a compound described herein, wherein the sample comprises:
  - (i) a first polynucleotide encoding a first fusion, wherein the first fusion comprises an non-luminescent polypeptide of an *Oplophorus*-derived luciferase and a first molecule, wherein the non-luminescent polypeptide is capable of forming a bioluminescent complex with the non-luminescent peptide; and
  - (ii) a second polynucleotide encoding a second fusion, wherein the second fusion comprises a fluorescent acceptor molecule and a second molecule; and
- (b) detecting bioluminescence resonance energy transfer (BRET) in the sample indicating an interaction or co-localization of the first molecule and the second molecule.

In one aspect, the disclosure provides a method to detect interaction or co-localization of molecules in a sample, the method comprising:
- (a) contacting a sample with a coelenterazine substrate and a compound described herein, wherein the sample comprises:
  - (i) a first fusion comprising a non-luminescent polypeptide of an *Oplophorus*-derived luciferase and a first molecule;
  - (ii) a second fusion comprising a non-luminescent peptide of an *Oplophorus*-derived luciferase and a second molecule, wherein the non-luminescent peptide is capable of forming a bioluminescent complex with the non-luminescent polypeptide; and
  - (iii) a third fusion comprising a fluorescent acceptor molecule and a third molecule; and
- (b) detecting bioluminescence resonance energy transfer (BRET) in the sample, indicating an interaction or co-localization between the first molecule, second molecule, and third molecule in the sample.

In one aspect, the disclosure provides a method to detect a molecule of interest in a sample, the method comprising:
- (a) contacting a sample comprising the molecule of interest fused to a non-luminescent peptide of an *Oplophorus*-derived luciferase with (i) a coelenterazine substrate;
(ii) a compound described herein; and
(iii) a non-luminescent polypeptide of an *Oplophorus*-derived luciferase, wherein the non-luminescent polypeptide is capable of forming a bioluminescent complex with the non-luminescent peptide; and
(b) detecting luminescence in the sample,
wherein detection of luminescence indicates formation of a bioluminescent complex between the non-luminescent peptide and the non-luminescent polypeptide.

In one aspect, the disclosure provides a method to detect a molecule of interest in a sample, the method comprising:
(a) contacting a sample comprising the molecule of interest fused to a non-luminescent polypeptide of an *Oplophorus*-derived luciferase with
(i) a coelenterazine substrate;
(ii) a compound disclosed herein; and
(iii) a non-luminescent peptide of an *Oplophorus*-derived luciferase, wherein the non-luminescent peptide is capable of forming a bioluminescent complex with the non-luminescent polypeptide; and
(b) detecting luminescence in the sample,
wherein detection of luminescence indicates formation of a bioluminescent complex between the non-luminescent peptide and the non-luminescent polypeptide.

In one aspect, the disclosure provides a method to detect a molecule of interest in a sample, the method comprising:
(a) contacting a sample comprising the molecule of interest fused to a non-luminescent peptide of an *Oplophorus*-derived luciferase with
(i) a coelenterazine substrate;
(ii) a compound described herein; and
(iii) a fusion comprising a non-luminescent polypeptide of an *Oplophorus*-derived luciferase and a fluorescent moiety, wherein the non-luminescent polypeptide is capable of forming a bioluminescent complex with the non-luminescent peptide; and
(b) detecting bioluminescence resonance energy transfer (BRET) in the sample, indicating detection of the molecule.

In one aspect, the disclosure provides a method to detect a molecule of interest in a sample, the method comprising:
(a) contacting a sample comprising the molecule of interest fused to a non-luminescent polypeptide of an *Oplophorus*-derived luciferase with
(i) a coelenterazine substrate;
(ii) a compound disclosed herein; and
(iii) a fusion comprising a non-luminescent peptide of an *Oplophorus*-derived luciferase and a fluorescent moiety, wherein the non-luminescent peptide is capable of forming a bioluminescent complex with the non-luminescent polypeptide; and
(b) detecting bioluminescence resonance energy transfer (BRET) in the sample, indicating detection of the molecule.

In one aspect, the disclosure provides a bioluminescence resonance energy transfer (BRET) system comprising:
(a) a first fusion comprising a non-luminescent peptide of an *Oplophorus*-derived luciferase and a first molecule;
(b) a second fusion comprising a non-luminescent polypeptide of an *Oplophorus*-derived luciferase and a fluorescent moiety, wherein the non-luminescent polypeptide is capable of forming a bioluminescent complex with the non-luminescent peptide;
(c) a coelenterazine substrate; and
(d) a compound described herein.

In one aspect, the disclosure provides a bioluminescence resonance energy transfer (BRET) system comprising:
(a) a first fusion comprising a non-luminescent polypeptide of an *Oplophorus*-derived luciferase and a first molecule;
(b) a second fusion comprising a non-luminescent peptide of an *Oplophorus*-derived luciferase and a fluorescent moiety, wherein the non-luminescent peptide is capable of forming a bioluminescent complex with the non-luminescent polypeptide;
(c) a coelenterazine substrate; and
(d) a compound described herein.

In one aspect, the disclosure provides a bioluminescence resonance energy transfer (BRET) system comprising:
(a) a first fusion comprising a first molecule and a non-luminescent peptide of an *Oplophorus*-derived luciferase;
(b) a second fusion comprising a second molecule and a fluorescent acceptor molecule;
(c) a non-luminescent polypeptide of *Oplophorus*-derived luciferase capable of forming a bioluminescent complex with the non-luminescent polypeptide of an *Oplophorus*-derived luciferase;
(d) a coelenterazine substrate; and
(e) a compound described herein.

In one aspect, the disclosure provides a bioluminescence resonance energy transfer (BRET) system comprising:
(a) a first fusion comprising a first molecule and a non-luminescent polypeptide of an *Oplophorus*-derived luciferase;
(b) a second fusion comprising a second molecule and a fluorescent acceptor molecule;
(c) a non-luminescent peptide of *Oplophorus*-derived luciferase capable of forming a bioluminescent complex with the non-luminescent polypeptide of an *Oplophorus*-derived luciferase;
(d) a coelenterazine substrate; and
(e) a compound described herein.

In one aspect, the disclosure provides a kit comprising:
(a) a compound described herein;
(b) a first polynucleotide encoding a non-luminescent peptide of an *Oplophorus*-derived luciferase; and
(c) a second polynucleotide encoding a non-luminescent polypeptide of an *Oplophorus*-derived luciferase, wherein the non-luminescent polypeptide is capable of forming a bioluminescent complex with the non-luminescent peptide.

BRIEF DESCRIPTION OF THE DRAWINGS

FIG. 1A shows inhibition of the NanoBiT® HiBiT/LgBiT bioluminescent complex. FIG. 1B shows the inhibition of the NanoBiT® SmBiT/LgBiT bioluminescent complex. FIG. 1C is a bar graph showing the calculated $IC_{50}$ values of the exemplary compounds shown in FIGS. 1A and 1B.

FIG. 3A shows inhibition of NanoBiT® HiBit/LgBit bioluminescent complex with HL-0005 in a cellular context. FIG. 3B compares $IC_{50}$ values in lytic and non-lytic conditions indicating HL-0005 is mostly cell permeable.

DETAILED DESCRIPTION

Figure 1A:
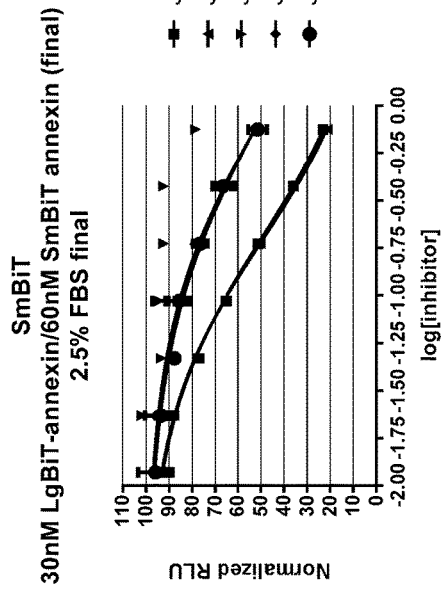
FIGS. 1A-1C show the inhibition of bioluminescent complexes by exemplary compounds of the present invention.

The disclosed compounds may selectively inhibit *Oplophorus*-luciferase derived bioluminescent complexes. For example, the disclosed compounds may selectively inhibit a *Oplophorus*-luciferase derived bioluminescent complex comprising: (a) a peptide comprising a peptide amino acid sequence having less than 100% sequence identity (e.g., >99%, <95%, <90%, <80%, <70%, <60%, <50%, etc.) and greater than 40% (e.g., >40%, >45%, >50%, >55%, >60%, >65%, >70%, >75%, >80%, >85%, >90%, >95%, >98%, >99%) with SEQ ID NO: 2; and (b) a polypeptide comprising a polypeptide amino acid sequence having less than 100% (e.g., >99%, <95%, <90%, <80%, <70%, <60%, <50%, etc.) and greater than 40% (e.g., >40%, >45%, >50%, >55%, >60%, >65%, >70%, >75%, >80%, >85%, >90%, >95%, >98%, >99%) sequence identity with SEQ ID NO: 3, wherein the bioluminescent complex exhibits detectable luminescence in the presence of a coelenterazine substrate. In certain embodiments, the disclosed compounds may selectively inhibit a *Oplophorus*-luciferase derived bioluminescent complex: (a) a peptide comprising a peptide amino acid sequence SEQ ID NO: 4 or SEQ ID NO: 6; and (b) a polypeptide comprising a polypeptide amino acid sequence having SEQ ID NO: 5, wherein the bioluminescent complex exhibits detectable luminescence in the presence of a coelenterazine substrate. Exemplary bioluminescent complexes that may be inhibited using the disclosed compounds are described in U.S. Pat. Nos. 9,797,889 and 9,797,890, the entire contents of which are incorporated by reference in their entirety. For example, the disclosed compounds may selectively inhibit a NanoBiT® HiBiT/LgBiT bioluminescent complex. As another example, the disclosed compounds may selectively inhibit a NanoBiT® LgBiT/SmBiT bioluminescent complex.

Due to their stabilities, the potential to be excreted from cells, and the presence of cell debris arising from culturing cells, it may be advantageous to use the selective inhibitors of the present invention to suppress the luminescence from *Oplophorus* luciferase-derived bioluminescent complexes in certain applications. For example, in applications involving temporal multiplexing of multiple luminescent systems, it can be beneficial to have selective inhibitors for each system to allow for the measurement and/or detection of only one luminescent signal at a time. Additionally, in some plate-based assays, a certain amount of luciferase may be excreted from cells or may be present in culture media from cellular debris. An extracellular inhibitor compound would allow for luminescence from luciferase in media to be selectively suppressed and may, therefore, help to improve the signal-to-background ratio in certain assays.

In particular embodiments, the light generated from NanoBiT® bioluminescent complexes may be selectively suppressed by the compounds disclosed herein. Advantageously, such selective inhibition may be used to enable temporal multiplexing of multiple bioluminescent systems such as NanoBiT and NanoLuc. Further, the disclosed compounds provide selective bioluminescent suppression (e.g., intracellular or extracellular selectivity) to enable certain plate-based assays. The compounds may compete for binding of the coelenterazine substrates of the luciferases and can be modified to produce both cell-permeable and cell-impermeable inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "substituent" or "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, sulfonic acid groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkyl-amino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents. The substituents can also be in salt forms (e.g., a sulfonic acid group can be in the form of a sulfonate group.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry, $5^{th}$ Edition*, John Wiley & Sons, Inc., New York, 2001; Larock, *Comprehensive Organic Transformations*, VCH Publishers, Inc., New York, 1989; Carruthers, Some *Modern Methods of Organic Synthesis, $3^{rd}$* Edition, Cambridge University Press, Cambridge, 1987; the entire contents of each of which are incorporated herein by reference.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkoxy" refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, ethoxycarbonylmethyl, 3-methoxycarbonylpropyl, 4-ethoxycarbonylbutyl, and 2-tert-butoxycarbonylethyl.

As used herein, the term "alkyl" refers to a linear or branched hydrocarbon radical, suitably having 1 to 30 carbon atoms, 1 to 12 carbon atoms, 1 to 10 carbon atoms, 1 to 8 carbon atoms, 1 to 6 carbon atoms, or 1 to 4 carbon atoms. The term "$C_1$-$C_8$-alkyl" is defined to include alkyl groups having 1, 2, 3, 4, 5, 6, 7 or 8 carbons in a linear or branched arrangement. For example, "$C_1$-$C_8$-alkyl" specifically includes methyl, ethyl, n-propyl, iso-propyl, n-butyl, sec-butyl, iso-butyl, tert-butyl, pentyl (e.g., n-pentyl), hexyl (e.g., n-hexyl), heptyl (e.g., n-heptyl) and octyl (e.g., n-octyl). The term "$C_1$-$C_6$-alkyl" is defined to include alkyl groups having 1, 2, 3, 4, 5, or 6 carbons in a linear or branched arrangement. For example, "$C_1$-$C_6$-alkyl" specifically includes methyl, ethyl, n-propyl, iso-propyl, n-butyl, sec-butyl, iso-butyl, tert-butyl, pentyl (e.g., n-pentyl), and hexyl (e.g., n-hexyl). The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, sec-butyl, iso-butyl and tert-butyl. Alkyl groups of the present invention may be unsubstituted or substituted by one or more suitable substituents, such as 1 to 3 suitable substituents, as defined above. For example, an alkyl group can be substituted with one or more halo substituents to form a haloalkyl group, or with one or more hydroxy substituents to form a hydroxyalkyl group, or with one or more alkoxy groups to form an alkoxyalkyl group.

As used herein, the term "alkylamino" refers to an alkyl group, as defined herein, appended to the parent molecular moiety through an amino group, as defined herein. Representative examples of alkylamino include, but are not limited to, methylamino, ethylamino, iso-propylamino, butylamino and sec-butylamino.

As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

As used herein, the term "alkylcarbonylalkyl" refers to an alkylcarbonyl group, as defined herein, appended to the parent molecular moiety through an alkyl group, as defined herein.

As used herein, the term "alkylcarbonylalkylamido" refers to an alkylcarbonyl group, as defined herein, appended to the parent molecular moiety through an alkylamido group, as defined herein.

The term "alkylene" means a divalent group derived from a saturated, straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2C(CH_3)_2$—, and —$CH_2CH(CH_3)CH_2$—.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present invention include, but are not limited to, ethynyl, propynyl, and butynyl. Alkynyl groups of the present invention may be unsubstituted or substituted by one or more suitable substituents, preferably 1 to 3 suitable substituents, as defined above.

As used herein, the term "amido" refers to an amino group appended to the parent molecular moiety through a carbonyl group, as defined herein (i.e., —$CONH_2$). The term "alkylamido," as used herein, refers to an alkylamino group or dialkylamino group appended to the parent molecular moiety through a carbonyl group, as defined herein. Representative examples of alkylamido include, but are not limited to, methylaminocarbonyl, dimethylaminocarbonyl, ethylmethylaminocarbonyl, and n-hexylaminocarbonyl.

As used herein, the term "amino" refers to an —$NH_2$ group.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl, 3-aminopropyl, 4-aminobutyl, 5-aminopentyl, and 6-aminohexyl.

As used herein, the term "aminoalkylamido" refers to at least one amino group, as defined herein, appended to the parent molecular moiety through an alkylamido group, as defined herein.

As used herein, the term "amino protecting group," refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include, but are not limited to, carbobenzyloxy (—NHCO—OCH$_2$C$_6$H$_5$ or —NH-Cbz); t-butyloxycarbonyl (—NHCO—OC(CH$_3$)$_3$ or —NH-Boc); 9-fluorenylmethyloxycarbonyl (—NH—Fmoc), 2,2,2-trichloroethyloxycarbonyl (—NH-Troc), and allyloxycarbonyl (—NH-Alloc). In each of the above, the —NH— represents the nitrogen from the amino group that is being protected.

As used herein, the term "aminoluciferin" refers to (4S)-2-(6-amino-1,3-benzothiazol-2-yl)-4,5-dihydrothiazole-4-carboxylic acid, or a substituted analog of this molecule.

As used herein, the term "aryl" means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined above. The aryl as used herein includes a phenyl appended to the parent molecular moiety and fused to a cycloalkyl group (e.g., indanyl or 5,6,7,8-tetrahydronaphthalen-2-yl), a phenyl group (i.e., naphthyl), or a non-aromatic heterocycle (e.g., benzo[d][1,3]dioxol-5-yl).

As used herein, the term "arylalkyl" refers to an aryl group, as defined herein, appended to the parent molecular moiety through an alkyl group, as defined herein. Representative examples of arylalkyl include, but are not limited to, phenylmethyl (i.e. benzyl) and phenylethyl.

As used herein, the term "arylcarbonyl" refers to an aryl group, as defined herein, appended to the parent molecular moiety through a carbonyl group, as defined herein.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "carboxy" refers to a —C(O)OH group.

As used herein, the term "carboxyalkyl" refers to a carboxy group as defined herein, appended to the parent molecular moiety through an alkyl group as defined herein.

As used herein, the term "carboxyalkylamido" refers to a carboxyalkyl group as defined herein, appended to the parent molecular moiety through an amido group as defined herein.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "cycloalkylalkyl" refers to a cycloalkyl group, as defined herein, appended to the parent molecular moiety through an alkyl group, as defined herein. Representative examples of cycloalkylalkyl include, but are not limited to, cyclohexylmethyl.

As used herein, the term "cycloalkylamido" refers to a cycloalkyl group, as defined herein, appended to the parent molecular moiety through an amido group, as defined herein.

As used herein, the term "dialkylamino" refers to two independently selected alkyl groups, as defined herein, appended to the parent molecular moiety through an amino group, as defined herein. Representative examples of dialkylamino include, but are not limited to, N,N-dimethylamino, N-ethyl-N-methylamino, and N-isopropyl-N-methylamino.

As used herein, the term "dialkylaminoalkyl" refers to a dialkylamino group, as defined herein, appended to the parent molecular moiety through an alkyl group, as defined herein. Representative examples of dialkylaminoalkyl include, but are not limited to, N,N-dimethylaminoethyl and N,N-methyl(2-propyl)aminoethyl.

As used herein, the term "dialkylaminoalkylamido" refers to a dialkylamino group, as defined herein, appended to the parent molecular moiety through an alkylamido group, as defined herein.

As used herein, the term "halogen" or "halo" refers to a fluoro, chloro, bromo or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4-trifluorobutyl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, 5,6,7,8-tetrahydroquinolin-5-yl, cyclopenta[b]thiophen-2-yl, and 4,5,6,7-tetrahydrobenzo[b]thiophen-2-yl. Heteroaryl groups of the present invention may be unsubstituted or substituted by one or more suitable substituents, preferably 1 to 5 suitable substituents, as defined above.

As used herein, the term "heteroarylalkyl" refers to a heteroaryl group, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may be unsubstituted or substituted by one or more suitable substituents, preferably 1 to 3 suitable substituents, as defined above. Heterocyclic groups of the present invention may contain one or more oxo groups (=O) or thioxo (=S) groups attached to the ring.

As used herein, the term "heterocyclylalkyl" refers to a heterocyclyl group, as defined herein, appended to the parent molecular moiety through an alkyl group, as defined herein. Representative examples of heterocyclylalkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl, and 3-morpholinopropyl.

As used herein, the term "heterocyclylamido" refers to a heterocyclyl group, as defined herein, appended to the parent molecular moiety through an amido group, as defined herein.

As used herein, the term "hydroxy" refers to an —OH group.

As used herein, the term "hydroxyalkoxy" refers to an alkoxy group, as defined herein, substituted by at least one hydroxy group. Representative examples of hydroxyalkoxy include, but are not limited to, hydroxyethoxy, and 2-hydroxypropoxy.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "hydroxyalkylamido" as used herein refers to a hydroxyalkyl group attached to an amido group, e.g., -amido-alkyl-OH.

As used herein, the term "hydroxycarbonyl" refers to a hydroxy group, as defined herein, appended to the parent molecular moiety through a carbonyl group, as defined herein.

As used herein, the term "methylenedioxy" refers to a —OCH$_2$O— group wherein the oxygen atoms of the methylenedioxy are attached to the parent molecular moiety through two adjacent carbon atoms.

As used herein, the term "oxo" refers to a double bonded oxygen (=O) radical wherein the bond partner is a carbon atom. Such a radical can also be thought as a carbonyl group.

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

A prefix attached to a multi-component substituent only applies to the first component it precedes. To illustrate, the term "cycloalkylalkyl" contains two components: alkyl and cycloalkyl. Thus, the $C_{1-10}$ prefix on $C_{1-10}$cycloalkylalkyl means that the alkyl component of the cycloalkylalkyl contains from 1 to 6 carbon atoms; the $C_1$-$C_6$-prefix does not describe the cycloalkyl component. To illustrate further, the term $C_{1-10}$haloalkyl refers to halomethyl, haloethyl, halopropyl, halobutyl, halopentyl, and halohexyl. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxyhaloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted," a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted," it means that the substituent does not have any substituents. If a substituent is described as being "optionally substituted," the substituent may be either (1) unsubstituted or (2) substituted. If a substituent is described as being optionally substituted with up to a particular number of non-hydrogen radicals, which substituent may be either (1) unsubstituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

As used herein, the term "bioluminescence" or "luminescence" may refer to light produced as a result of a reaction between an enzyme and a substrate that generates light. Examples of such enzymes (bioluminescent enzymes) include *Oplophorus* luciferase, e.g., *Oplophorous gracilirostris*, firefly luciferase, e.g. *Photinus pyralis* or *Photuris pennsylvanica*, click beetle luciferase, *Renilla* luciferase, cypridina luciferase, Aequorin photoprotein, obelin photoprotein, and the like.

As used herein, the term "complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules (e.g., a peptide and polypeptide) is formed under assay conditions such that the complex is thermodynamically favored (e.g., compared to a non-aggregated, or non-complexed, state of its component molecules). As used herein the term "complex," unless described as otherwise, refers to the assemblage of two or more molecules (e.g., peptides, polypeptides, or a combination thereof).

The terms "bioluminescent complex" or "*Oplophorus* luciferase-derived bioluminescent complex" as used interchangeably herein, refer to the assembled complex of two or more non-luminescent peptides and/or non-luminescent polypeptides. The bioluminescent complex catalyzes or enables the conversion of a substrate for the bioluminescent complex into an unstable form; the substrate subsequently emits light. When uncomplexed, two non-luminescent elements that form a bioluminescent complex may be referred to as a "non-luminescent pair." If a bioluminescent complex is formed by three or more non-luminescent peptides and/or non-luminescent polypeptides, the uncomplexed constituents of the bioluminescent complex may be referred to as a "non-luminescent group." An *Oplophorus* luciferase-derived bioluminescent complex may include (a) a peptide comprising a peptide amino acid sequence having less than 100% sequence identity (e.g., >99%, <95%, <90%, <80%, <70%, <60%, <50%, etc.) and greater than 40% (e.g., >40%, >45%, >50%, >55%, >60%, >65%, >70%, >75%, >80%, >85%, >90%, >95%, >98%, >99%) with SEQ ID NO: 2; and (b) a polypeptide comprising a polypeptide amino acid sequence having less than 100% identity (e.g., >99%, <95%, <90%, <80%, <70%, <60%, <50%, etc.) and greater than 40% (e.g., >40%, >45%, >50%, >55%, >60%, >65%, >70%, >75%, >80%, >85%, >90%, >95%, >98%, >99%) sequence identity with SEQ ID NO: 3, wherein the bioluminescent complex exhibits detectable luminescence. In certain embodiments, the present invention provides bioluminescent complexes comprising: (a) a peptide comprising a peptide amino acid sequence having SEQ ID NO: 4 or 6; and (b) a polypeptide comprising a polypeptide amino acid sequence having SEQ ID NO: 5, wherein the bioluminescent complex exhibits detectable luminescence. Exemplary *Oplophorus* luciferase-derived bioluminescent complexes include the NanoBliT® technology that includes a SmBiT non-luminescent peptide (SEQ ID NO: 6), NanoBliT® HiBiT non-luminescent peptide (SEQ ID NO: 4), and/or NanoBliT® LgBiT non-luminescent polypeptide (SEQ ID NO: 5).

As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent." For example, a non-luminescent polypeptide (NLpoly) is substantially non-luminescent, exhibiting, for example, a 10-fold or more (e.g., 100-fold, 200-fold, 500-fold, $1 \times 10^3$-fold, $1 \times 10^4$-fold, $1 \times 10^5$-fold, $1 \times 10^6$-fold, $1×10^7$-fold, etc.) reduction in luminescence compared to a complex of the NLpoly with its non-luminescent complement peptide. In some embodiments, an entity is "non-luminescent" if any light emission is sufficiently minimal so as not to create interfering background for a particular assay.

As used herein, the terms "non-luminescent peptide" (e.g., NLpep) and "non-luminescent polypeptide" (e.g., NLpoly) refer to peptides and polypeptides that exhibit substantially no luminescence (e.g., in the presence of a substrate), or an amount that is beneath the noise, or a 10-fold or more (e.g., 100-fold, 200-fold, 500-fold, $1×10^3$-fold, $1×10^4$-fold, $1×10^5$-fold, $1×10^6$-fold, $1×10^7$-fold, etc.) when compared to a significant signal (e.g., luminescent complex) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex. As used herein, a "non-luminescent element" is a non-luminescent peptide or non-luminescent polypeptide.

As used herein, the term "interaction element" or "interaction molecule" refers to a moiety that assists in bringing together a pair of non-luminescent elements or a non-luminescent group to form a bioluminescent complex. In a typical embodiment, a pair of interaction elements (a.k.a. "interaction pair") is attached to a pair of non-luminescent elements (e.g., non-luminescent peptide/polypeptide pair), and the attractive interaction between the two interaction elements facilitates formation of the bioluminescent complex; although the present invention is not limited to such a mechanism, and an understanding of the mechanism is not required to practice the invention. Interaction elements may facilitate formation of the bioluminescent complex by any suitable mechanism (e.g., bringing non-luminescent pair/group into close proximity, placing a non-luminescent pair/group in proper conformation for stable interaction, reducing activation energy for complex formation, combinations thereof, etc.). An interaction element may be a protein, polypeptide, peptide, small molecule, cofactor, nucleic acid, lipid, carbohydrate, antibody, etc. An interaction pair may be made of two of the same interaction elements (i.e. homopair) or two different interaction elements (i.e. heteropair). In the case of a heteropair, the interaction elements may be the same type of moiety (e.g., polypeptides) or may be two different types of moieties (e.g., polypeptide and small molecule). In some embodiments, in which complex formation by the interaction pair is studied, an interaction pair may be referred to as a "target pair" or a "pair of interest," and the individual interaction elements are referred to as "target elements" (e.g., "target peptide," "target polypeptide," etc.) or "elements of interest" (e.g., "peptide of interest," "polypeptide or interest," etc.).

As used herein, the terms "fusion", "fusion polypeptide", and "fusion protein" refer to a chimeric protein containing a first protein or polypeptide of interest (e.g., target sequence, etc.) joined to a second different peptide, polypeptide, or protein (e.g., detectable sequence, isolatable sequence, tag, etc.). The term "traditional fusion" refers to a fusion in which the first polypeptide or protein and the second peptide, polypeptide, or protein are fused end to end (e.g., C-terminus to N-terminus or N-terminus to C-terminus).

As used herein, the term "coelenterazine", "coelenterazine substrate", "coelenterazine derivative", or "coelenterazine derivative substrate" refers to a class of reporter molecules that luminesce when acted upon by a wide variety of bioluminescent proteins such as luciferases (e.g., marine luciferases). As used herein, the terms "coelenterazine", "coelenterazine substrate", "coelenterazine derivative", or "coelenterazine derivative substrate" refer to naturally-occurring ("native") coelenterazine. As used herein, the terms "a coelenterazine", "a coelenterazine substrate", "a coelenterazine derivative", or "a coelenterazine derivative substrate" refers to native coelenterazine as well as synthetic, e.g., derivative or variant, and natural analogs thereof, including furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100; U.S. application Ser. No. 12/056,073 (paragraph [0086]); and U.S. Pat. No. 8,669,103; the disclosures of which are incorporated by reference herein in their entireties.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals and industrial samples. Such examples are not however to be construed as limiting the sample types applicable to the present invention.

The term "energy acceptor" or "acceptor molecule" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes) (Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog). In certain embodiments, energy acceptors include but are not limited to small molecule fluorescent dyes such as NCT, quenchers, fluorescent particles such as Quantum dots, luminescent metal complexes, and any other known energy acceptors.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a pre-luciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as Aequorin, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the terms "*Oplophorus* luciferase" and "*Oplophorus*-derived luciferase" are used interchangeably and refer to a luciferase secreted from the deep-sea shrimp *Oplophorus gracilirostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety.

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluoroluciferin, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a flurophore, such as coumarin, R110, fluoroscein, DDAO, resorufin, cresyl violet, sily xanthene, or carbopyronine. Fluorescence may be detected using a fluorometer.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

Provided herein are compounds that may selectively inhibit *Oplophorus* luciferase-derived bioluminescent complex, e.g., inhibit luciferase activity of the bioluminescent complex. In one aspect, disclosed are compounds of formula (I), or salts thereof:

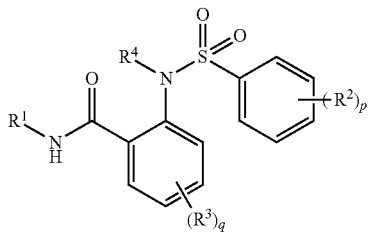

wherein:
R$^1$ is an aryl, a cycloalkyl, a heteroaryl, a heterocycle, an arylalkyl, a cycloalkylalkyl, a heteroarylalkyl, or a heterocyclylalkyl, wherein the aryl, cycloalkyl, heteroaryl, and heterocycle are optionally substituted with one or more R$^W$, wherein each R$^W$ is independently selected from the group consisting of C$_{1-10}$alkyl, C$_{1-10}$haloalkyl, halogen, —CN, —OR$^A$, —C$_{1-10}$alkylene-OR$^A$, —CO—R$^A$, —C$_{1-10}$alkylene-CO—R$^A$, —CO—OR$^A$, —C$_{1-10}$alkylene-CO—OR$^A$, —CO—NHR$^A$, —C$_{1-10}$alkylene-CO—NHR$^A$, —NR$^B$R$^C$, —C$_{1-10}$alkylene-NR$^B$R$^C$, —NH—CO—C$_{1-4}$alkyl, —C$_{1-10}$alkylene-NH—CO—C$_{1-4}$alkyl, phenyl, and phenyl substituted with 1, 2, 3, or 4 R$^D$ groups;
each R$^2$ is independently C$_{1-10}$alkyl, C$_{1-10}$haloalkyl, halogen, —CN, —OR$^A$, —C$_{1-4}$alkylene-OR$^A$, —CO—R$^A$, —C$_{1-4}$alkylene-CO—R$^A$, —CO—OR$^A$, —C$_{1-4}$alkylene-CO—OR$^A$, —CO—NHR$^A$, —C$_{1-4}$alkylene-CO—NR$^A$, —NR$^B$R$^C$, —C$_{1-4}$alkylene-NR$^B$R$^C$, —NH—CO—C$_{1-4}$alkyl, —C$_{1-4}$alkylene-NH—CO—C$_{1-4}$alkyl, phenyl, phenyl substituted with 1, 2, 3, or 4 R$^D$ groups, —C≡C—R$^A$, or —C≡C—C$_{1-4}$alkylene-OR$^A$, or two R$^2$ together with the carbon atoms of the

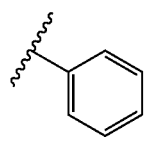 [SMILES: *c1ccccc1]

moiety to which they are attached form a 5- or 6-membered fused ring;
each R$^3$ is independently C$_{1-10}$alkyl, C$_{1-10}$haloalkyl, halogen, —CN, —OR$^A$, —C$_{1-4}$alkylene-OR$^A$, —CO—R$^A$, —CO—OR$^A$, or —CO—NHR$^A$, or two R$^3$ together with the carbon atoms of the

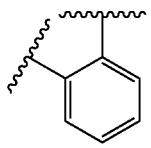

moiety to which they are attached form a 5- or 6-membered fused ring;
R$^4$ is H or C$_{1-4}$alkyl;
p is 0, 1, 2, 3, or 4;
q is 0, 1, 2, 3, or 4;
R$^A$ at each occurrence is independently H, C$_{1-4}$alkyl, or C$_{1-4}$haloalkyl;
R$^B$ and R$^C$ at each occurrence are independently H or C$_{1-4}$alkyl, or R$^B$ and R$^C$ together with the N atom to which they are attached form a 5- or 6-membered heterocycle; and
R$^D$ at each occurrence is independently C$_{1-4}$alkyl, —OC$_{1-4}$alkyl, —CN, or halogen.

In some embodiments, in compounds of formula (I):
R$^1$ is an aryl, a cycloalkyl, a heteroaryl, or a heterocycle, wherein the aryl, cycloalkyl, heteroaryl, and heterocycle are optionally substituted with one or more R$^W$, wherein each R$^W$ is independently selected from the group consisting of C$_{1-10}$alkyl, C$_{1-10}$haloalkyl, halogen, —CN, —OR$^A$, —C$_{1-10}$alkylene-OR$^A$, —CO—R$^A$, —C$_{1-10}$alkylene-CO—R$^A$, —CO—OR$^A$, —C$_{1-10}$alkylene-CO—OR$^A$, —CO—NHR$^A$, —C$_{1-10}$alkylene-CO—NHR$^A$, —NR$^B$R$^C$, —C$_{1-10}$alkylene-NR$^B$R$^C$, —NH—CO—C$_{1-4}$alkyl, —C$_{1-10}$alkylene-NH—CO—C$_{1-4}$alkyl, phenyl, and phenyl substituted with 1, 2, 3, or 4 R$^D$ groups;
each R$^2$ is independently C$_{1-10}$alkyl, C$_{1-10}$haloalkyl, halogen, —CN, —OR$^A$, —C$_{1-4}$alkylene-OR$^A$, —CO—R$^A$, —C$_{1-4}$alkylene-CO—R$^A$, —CO—OR$^A$, —C$_{1-4}$alkylene-CO—OR$^A$, —CO—NHR$^A$, C$_{1-4}$alkylene-CO—NR$^A$, —NR$^B$R$^C$, —C$_{1-4}$alkylene-NR$^B$R$^C$, —NH—CO—C$_{1-4}$alkyl, —C$_{1-4}$alkylene-NH—CO—C$_{1-4}$alkyl, phenyl, phenyl substituted with 1, 2, 3, or 4 R$^D$ groups, —C≡C—R$^A$, or —C≡C—C$_{1-4}$alkylene-OR$^A$, or two R$^2$ together with the carbon atoms of the

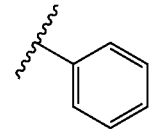 [SMILES: *c1ccccc1]

moiety to which they are attached form a 5- or 6-membered fused ring;
each R$^3$ is independently C$_{1-10}$alkyl, C$_{1-10}$haloalkyl, halogen, —CN, —OR$^A$, —C$_{1-4}$alkylene-OR$^A$, —CO—R$^A$, —CO—OR$^A$, or —CO—NHR$^A$, or two R$^3$ together with the carbon atoms of the

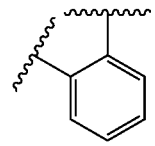 [SMILES: *c1ccccc1*]

moiety to which they are attached form a 5- or 6-membered fused ring;
R$^4$ is H or C$_{1-4}$alkyl;
p is 0, 1, 2, 3, or 4;
q is 0, 1, 2, 3, or 4;
R$^A$ at each occurrence is independently H, C$_{1-4}$alkyl, or C$_{1-4}$haloalkyl;
R$^B$ and R$^C$ at each occurrence are independently H or C$_{1-4}$alkyl, or R$^B$ and R$^C$ together with the N atom to which they are attached form a 5- or 6-membered heterocycle; and
R$^D$ at each occurrence is independently C$_{1-4}$alkyl, —OC$_{1-4}$alkyl, —CN, or halogen.

In some embodiments, $R^1$ is an unsubstituted aryl, an unsubstituted cycloalkyl, an unsubstituted heteroaryl, an unsubstituted heterocycle, or an unsubstituted arylalkyl.

In some embodiments, $R^1$ is an unsubstituted aryl, an unsubstituted cycloalkyl, an unsubstituted heteroaryl, or an unsubstituted heterocycle.

In some embodiments, $R^1$ is an aryl (such as a $C_{6-20}$aryl) or a heteroaryl (such as a 5- to 12-membered heteroaryl), wherein the aryl and heteroaryl are optionally substituted with one or more $R^W$. In some embodiments, $R^1$ is a $C_{6-20}$aryl, wherein the aryl optionally substituted with one or more $R^W$. In some embodiments, $R^1$ is a 5- to 12-membered heteroaryl optionally substituted with one or more $R^W$. In some embodiments, $R^1$ is a $C_{5-10}$cycloalkyl optionally substituted with one or more $R^W$. In some embodiments, $R^1$ is a 5- to 12-membered heterocycle optionally substituted with one or more $R^W$.

In some embodiments, $R^1$ is

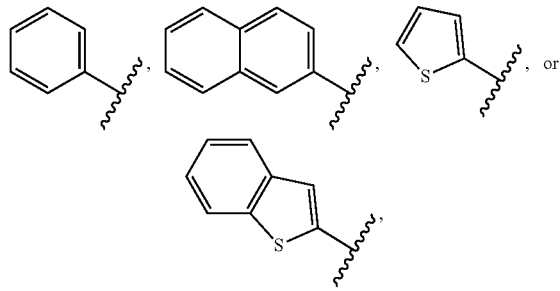

each optionally substituted with one or more $R^W$. In some embodiments, $R^1$ is

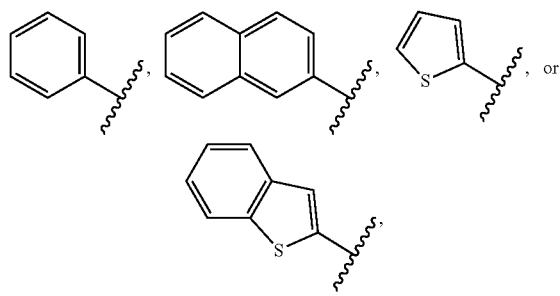

each of which is unsubstituted. In some embodiments, $R^1$ is

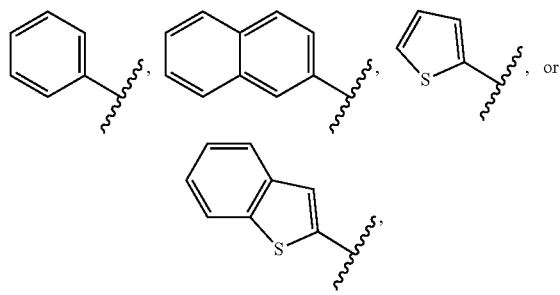

each of which is substituted with $C_{1-4}$alkyl or $C_{1-4}$haloalkyl.

In some embodiments, $R^1$ is

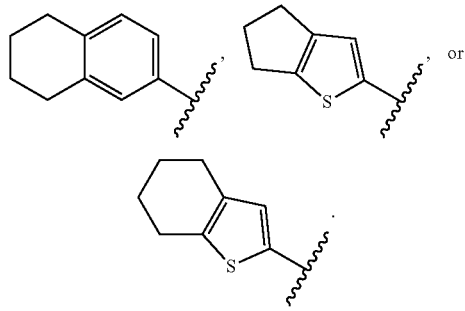

each of which is optionally substituted with one or more $R^W$. In some embodiments, $R^1$ is

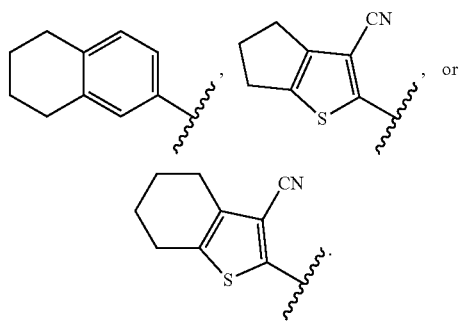

In some embodiments, each $R^W$ is independently selected from the group consisting of $C_{1-10}$alkyl, $C_{1-10}$haloalkyl, halogen, or —CN. In some embodiments, $R^W$ is —$OR^A$, —$C_{1-4}$alkylene-$OR^A$, —CO—$R^A$, —$C_{1-4}$alkylene-CO—$R^A$, —CO—$OR^A$, —$C_{1-4}$alkylene-CO—$OR^A$, —CO—$NHR^A$, or —$C_{1-4}$alkylene-CO—$NHR^A$. In some embodiments, $R^W$ is —$NR^BR^C$, —$C_{1-4}$alkylene-$NR^BR^C$, —NH—CO—$C_{1-4}$alkyl, or —$C_{1-4}$alkylene-NH—CO—$C_{1-4}$alkyl. In some embodiments, $R^W$ is phenyl or phenyl substituted with 1, 2, 3, or 4 $R^D$ groups. In some embodiments, $R^W$ is $C_{1-10}$alkyl, $C_{1-10}$haloalkyl, halogen, or —CN. In some embodiments, $R^W$ is $C_{1-4}$alkyl, such as methyl, ethyl, propyl, or butyl.

In some embodiments, $R^W$ is selected from the group consisting of $C_{1-10}$alkyl, $C_{1-10}$haloalkyl, halogen, —CN, —$OR^A$, —$C_{1-10}$alkylene-$OR^A$, —CO—$OR^A$, —$C_{1-10}$alkylene-CO—$OR^A$, and phenyl. In some embodiments, each $R^A$ is independently selected from hydrogen, methyl, and ethyl.

In some embodiments, $R^1$ is an arylalkyl (such as benzyl) that is optionally substituted with one or more $R^W$.

In some embodiments, $R^1$ is an aryl, a cycloalkyl, a heteroaryl, a heterocycle, or an arylalkyl, wherein the aryl, cycloalkyl, heteroaryl, and heterocycle are substituted with one $R^W$, wherein $R^W$ is selected from the group consisting of $C_{1-10}$alkyl, $C_{1-10}$haloalkyl, halogen, —CN, —$OR^A$, —$C_{1-10}$alkylene-$OR^A$, —CO—$OR^A$, —$C_{1-10}$alkylene-CO—$OR^A$, and phenyl, wherein each $R^A$ is independently selected from hydrogen, methyl, and ethyl.

In some embodiments, $R^1$ is

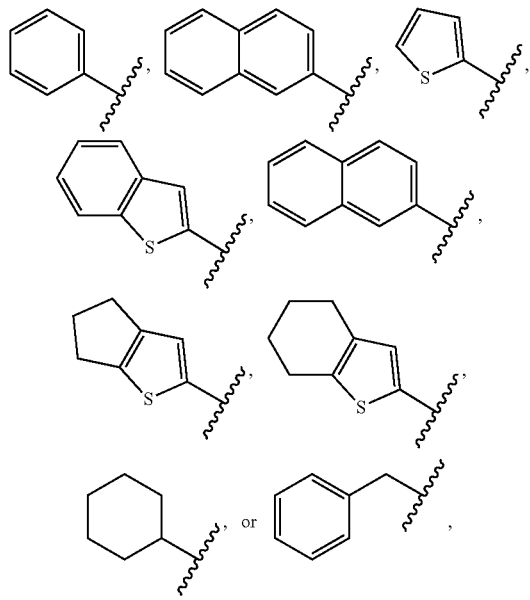

each of which is unsubstituted or substituted with one $R^W$, wherein $R^W$ is selected from the group consisting of $C_{1-10}$alkyl (e.g., methyl, ethyl, isopropyl, n-propyl, n-butyl, n-pentyl, n-hexyl, or n-octyl), $C_{1-10}$haloalkyl (e.g., —(CH$_2$)$_4$Br), halogen (e.g., fluoro, chloro, or bromo), —CN, —OR$^A$ (e.g., —OCH$_3$), —C$_{1-10}$alkylene-OR$^A$ (e.g., —(CH$_2$)$_4$—OH or —(CH$_2$)$_6$—OH), —CO—OR$^A$ (e.g., —COOH, —COOCH$_3$, or —COOCH$_2$CH$_3$), —C$_{1-10}$alkylene-CO—OR$^A$ (e.g., —CH$_2$COOH, —CH$_2$COOCH$_2$CH$_3$, —(CH$_2$)$_5$—COOH, or —(CH$_2$)$_5$—COOCH$_3$), and phenyl.

In some embodiments, p is 0, 1, or 2. In some embodiments, p is 0. In some embodiments, p is 1.

In some embodiments, $R^2$ is $C_{1-10}$alkyl, halogen, $C_{1-4}$haloalkyl, —OH, $C_{1-4}$alkylene-OH, —OC$_{1-4}$alkyl, —NH$_2$, phenyl, or —CO—OC$_{1-4}$alkyl. In some embodiments, $R^2$ is $C_{1-10}$alkyl. In some embodiments, $R^2$ is $C_{1-4}$alkyl, such as methyl, ethyl, propyl, or butyl. In some embodiments, $R^2$ is methyl. In some embodiments, $R^2$ is halogen, $C_{1-4}$haloalkyl, —OH, $C_{1-4}$alkylene-OH, —OC$_{1-4}$alkyl, or —NH$_2$.

In some embodiments, $R^2$ is selected from $C_{1-10}$alkyl, $C_{1-10}$haloalkyl, halogen, —OR$^A$, —C$_{1-4}$alkylene-OR$^A$, —CO—R$^A$, —CO—OR$^A$, —C$_{1-4}$alkylene-CO—OR$^A$, —CO—NHR$^A$, —NR$^B$R$^C$, —NH—CO—C$_{1-4}$alkyl, phenyl, and —C≡C—C$_{1-4}$alkylene-OR$^A$, wherein each $R^A$ is independently selected from hydrogen, methyl, ethyl, and trifluoromethyl.

In some embodiments, $R^2$ is selected from $C_{1-10}$alkyl (e.g., $C_{1-6}$alkyl, such as methyl, ethyl, isopropyl, n-propyl, n-butyl, n-pentyl, or n-hexyl), $C_{1-10}$haloalkyl (e.g., $C_{1-4}$haloalkyl, such as trifluoromethyl), halogen (e.g., fluoro, chloro, or bromo), —OR$^A$ (e.g., —OH, —OCH$_3$, —O(CH$_2$)$_3$CH$_3$, or —OCF$_3$), —C$_{1-4}$alkylene-OR$^A$ (e.g., —CH$_2$OH or —(CH$_2$)$_3$—OH), —CO—R$^A$ (e.g., —COH), —CO—OR$^A$ (e.g., —COOH or —COOCH$_3$), —C$_{1-4}$alkylene-CO—OR$^A$ (e.g., —(CH$_2$)$_2$COOCH$_3$, —CO—NHR$^A$ (e.g., —CONH(CH$_2$)$_3$CH$_3$, —NR$^B$R$^C$ (e.g., —NH$_2$ or —NH(CH$_2$)$_3$CH$_3$, —NH—CO—C$_{1-4}$alkyl (e.g., —NH—CO—CH$_3$), phenyl, —C≡C—R$^A$ (e.g., —C≡C—(CH$_2$)$_3$CH$_3$) and —C≡C—C$_{1-4}$alkylene-OR$^A$ (e.g., —C≡C—CH$_2$—OH). In some embodiments, each $R^A$ is independently selected from hydrogen, methyl, ethyl, n-propyl, and n-butyl.

In some embodiments, p is 2. In some embodiments, two $R^2$ together with the carbon atoms of the

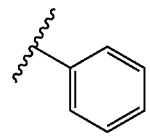 [SMILES: *c1ccccc1]

moiety to which they are attached form a 5- or 6-membered fused ring. For example, two $R^2$ together with the

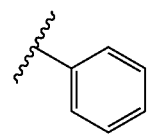

moiety to which they are attached may form

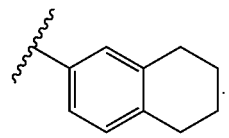 [SMILES: *c1ccc2c(c1)CCCC2]

In some embodiments, q is 0, 1, or 2. In some embodiments, q is 0. In some embodiments, q is 1.

In some embodiments, $R^3$ is selected from $C_{1-10}$alkyl, $C_{1-10}$haloalkyl, halogen, —CN, and —OR$^A$, wherein $R^A$ is selected from hydrogen and $C_{1-4}$alkyl. In some embodiments, $R^3$ is selected from $C_{1-10}$alkyl (e.g., $C_{1-4}$alkyl such as methyl, ethyl, isopropyl, n-propyl, or n-butyl), $C_{1-10}$haloalkyl (e.g., $C_{1-4}$haloalkyl such as trifluoromethyl), halogen (e.g., fluoro, chloro, or bromo), —CN, and —OR$^A$ (e.g., —OH or —OCH$_3$). In some embodiments, $R^3$ is $C_{1-4}$alkyl, halogen, —CN, —OH, or —OC$_{1-4}$alkyl. In some embodiments, $R^3$ is halogen. In some embodiments, $R^2$ is $C_{1-4}$alkyl (such as methyl) and $R^3$ is $C_{1-4}$alkyl, halogen, —CN, —OH, or —OC$_{1-4}$alkyl.

In some embodiments, q is 2. In some embodiments, two $R^3$ together with the carbon atoms of the

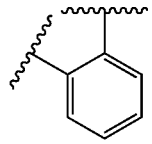 [SMILES: *c1ccccc1*]

moiety to which they are attached form a 5- or 6-membered fused ring. For example, two $R^3$ together with the

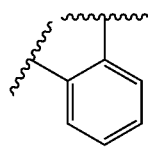 [SMILES: *c1ccccc1*]

moiety to which they are attached may form

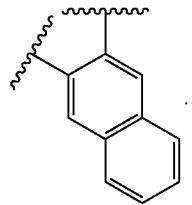 [SMILES: *c1cc2ccccc2cc1*]

In some embodiments, p is 1 and q is 0. In some embodiments, p is 1 and q is 1. In some embodiments, $R^2$ is $C_{1-4}$alkyl (such as methyl), p is 1 and q is 0. In some embodiments, $R^2$ is $C_{1-4}$alkyl (such as methyl), $R^3$ is $C_{1-4}$alkyl, halogen, —CN, —OH, or —OC$_{1-4}$alkyl, p is 1, and q is 1. In some embodiments, $R^2$ is methyl, $R^3$ is —CH$_3$, halogen (such as F), —OCH$_3$, or —CN, p is 1, and q is 1.

In some embodiments, $R^4$ is H. In some embodiments, $R^4$ is $C_{1-4}$alkyl. In some embodiments, $R^4$ is ethyl.

$R^A$ at each occurrence (as a substituent in $R^1$, $R^2$, or $R^3$) is independently H, $C_{1-4}$alkyl, or $C_{1-4}$haloalkyl. In some embodiments, $R^A$ is H. In some embodiments, $R^A$ is $C_{1-4}$alkyl. In some embodiments, $R^A$ is methyl. In some embodiments, $R^A$ is $C_{1-4}$haloalkyl, such as —CF$_3$.

$R^B$ and $R^C$ at each occurrence (as substituents in $R^1$ or $R^2$) are independently H or $C_{1-4}$alkyl, or $R^B$ and $R^C$ together with the N atom to which they are attached form a 5- or 6-membered heterocycle. In some embodiments, $R^B$ and $R^C$ are both H. In some embodiments, $R^B$ is H and $R^C$ is $C_{1-4}$alkyl. In some embodiments, $R^B$ is $C_{1-4}$alkyl and $R^C$ is $C_{1-4}$alkyl. In some embodiments, $R^B$ and $R^C$ together with the N atom to which they are attached form a 5- or 6-membered heterocycle.

In some embodiments, $R^D$ is $C_{1-4}$alkyl, such as methyl. In some embodiments, $R^D$ is —OC$_{1-4}$alkyl, such as —OCH$_3$. In some embodiments, $R^D$ is —CN or halogen.

In some embodiments, $R^1$ is

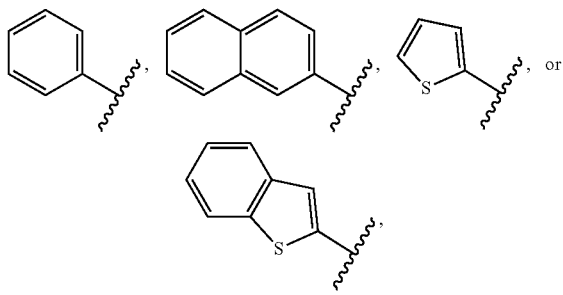

each of which is substituted with $C_{1-4}$alkyl or $C_{1-4}$haloalkyl, or $R^1$ is

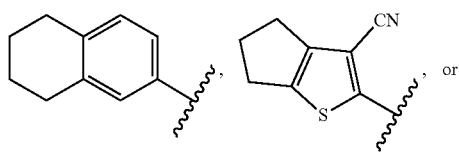

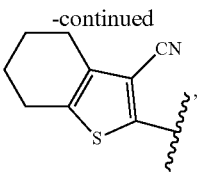

$R^2$ is $C_{1-4}$alkyl, halogen, $C_{1-4}$haloalkyl, —OH, $C_{1-4}$alkylene-OH, —OC$_{1-4}$alkyl, or —NH$_2$, $R^3$ is $C_{1-4}$alkyl, halogen, —CN, —OH, or —OC$_{1-4}$alkyl, p is 1, and q is 0 or 1.

In some embodiments, when p is 0, then $R^1$ is substituted with one or more $R^W$ (e.g., with one $R^W$). In some embodiments, when p is 0 and $R^1$ is phenyl, then $R^1$ is substituted with one or more $R^W$ (e.g., with one $R^W$). In some embodiments, when $R^1$ is unsubstituted, then p is 1, 2, 3, or 4 (e.g., p is 1 or 2, or p is 1). In some embodiments, when $R^1$ is unsubstituted phenyl, then p is 1, 2, 3, or 4 (e.g., p is 1 or 2, or p is 1). In some embodiments, the compound is not N-phenyl-2-(phenylsulfonamido)benzamide.

In some embodiments, the compounds of formula (I) are compounds of formula (I-a), or salts thereof,

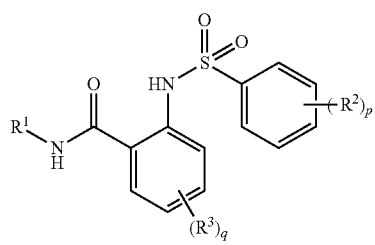

(I-a)

wherein $R^1$ is a $C_{6-20}$aryl or a 5- to 12-membered heteroaryl, wherein the aryl and heteroaryl are optionally substituted with one or more $R^W$;

p is 0, 1, or 2;

q is 0 or 1;

$R^3$ is $C_{1-4}$alkyl, halogen, —CN or —OR$^A$;

$R^A$ is H or $C_{1-4}$alkyl; and $R^2$ and $R^W$ are as defined herein.

In some embodiments, disclosed are compounds of formula (I-a), or salts thereof, wherein $R^1$ is an unsubstituted $C_{6-20}$aryl or an unsubstituted 5- to 12-membered heteroaryl.

In some embodiments, disclosed are compounds of formula (I-a), or salts thereof, wherein $R^1$ is

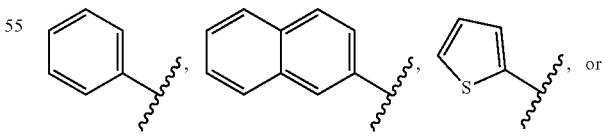

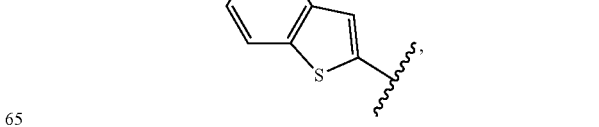

each optionally substituted with one or more $R^W$. In some embodiments, $R^1$ of formula (I-a) is

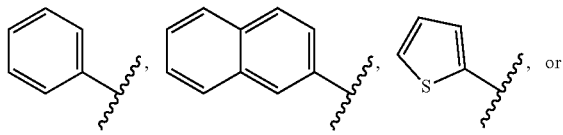, or

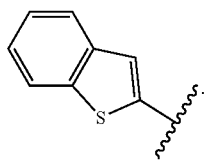.

In some embodiments, disclosed are compounds of formula (I-a), or salts thereof, wherein $R^1$ is substituted with $C_{1-4}$alkyl or $C_{1-4}$haloalkyl. For example, $R^1$ of formula (I-a) may be

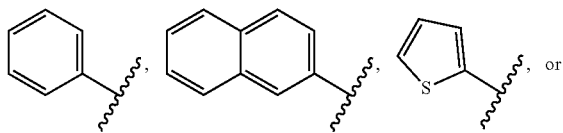, or

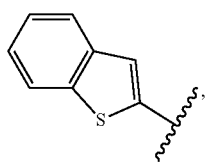, each substituted with $C_{1-4}$alkyl or $C_{1-4}$haloalkyl.

In some embodiments, disclosed are compounds of formula (I-a), or salts thereof, wherein $R^1$ is

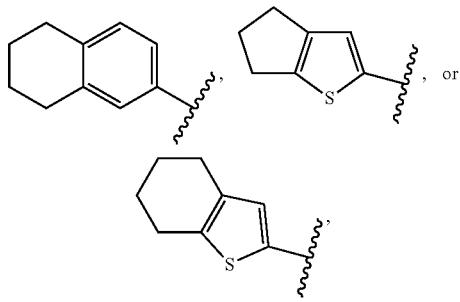

each of which is optionally substituted with one or more $R^W$. In some embodiments, $R^1$ is

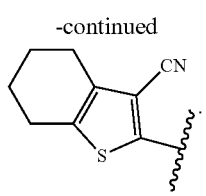.

In some embodiments, disclosed are compounds of formula (I-a), or salts thereof, wherein $R^1$ is

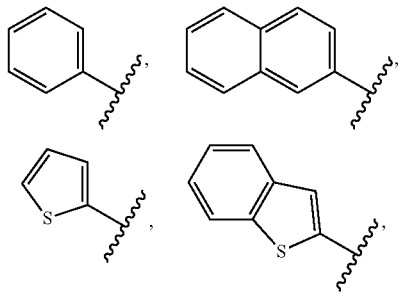

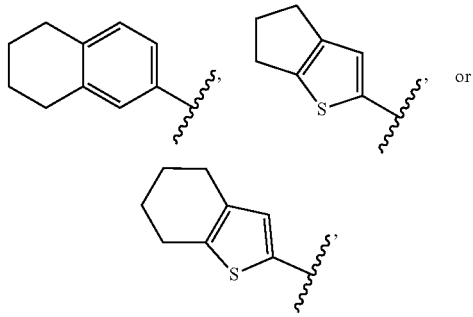

each of which is unsubstituted or substituted with one $R^W$, wherein $R^W$ is selected from the group consisting of $C_{1-10}$alkyl (e.g., methyl, ethyl, isopropyl, n-propyl, n-butyl, n-pentyl, n-hexyl, or n-octyl), $C_{1-10}$haloalkyl (e.g., —(CH$_2$)$_4$Br), halogen (e.g., fluoro, chloro, or bromo), —CN, —OR$^A$ (e.g., —OCH$_3$), —C$_{1-10}$alkylene-OR$^A$ (e.g., —(CH$_2$)$_4$—OH or —(CH$_2$)$_6$—OH), —CO—OR$^A$ (e.g., —COOH, —COOCH$_3$, or —COOCH$_2$CH$_3$), —C$_{1-10}$alkylene-CO—OR$^A$ (e.g., —CH$_2$COOH, —CH$_2$COOCH$_2$CH$_3$, —(CH$_2$)$_5$—COOH, or —(CH$_2$)$_5$—COOCH$_3$), and phenyl.

In some embodiments, disclosed are compounds of formula (I-a), or salts thereof, wherein $R^2$ is $C_{1-4}$alkyl (such as methyl, ethyl, propyl, or butyl), halogen, $C_{1-4}$haloalkyl, —OH, $C_{1-4}$alkylene-OH, —OC$_{1-4}$alkyl, —NH$_2$, phenyl, or —CO—OC$_{1-4}$alkyl, or $R^2$ together with the carbon atoms of the

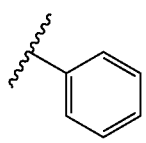 [SMILES: *c1ccccc1]

moiety to which they are attached form a 5- or 6-membered fused ring. For example, two $R^2$ of formula (I-a) together with the

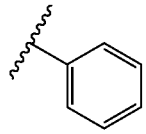

moiety to which it is attached may form

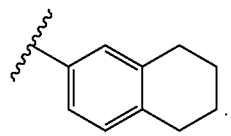 [SMILES: *c1ccc2c(c1)CCCC2]

In some embodiments, disclosed are compounds of formula (I-a), or salts thereof, wherein $R^2$ is $C_{1-4}$alkyl (such as methyl). In some embodiments, disclosed are compounds of formula (I-a), or salts thereof, wherein $R^2$ is —OH, —$C_{1-4}$alkylene-OH (such as —$CH_2$OH), —O$C_{1-4}$alkyl (such as —OCH$_3$), or —NH$_2$. In some embodiments, disclosed are compounds of formula (I-a), or salts thereof, wherein p is 1 and q is 0. In some embodiments, disclosed are compounds of formula (I-a), or salts thereof, wherein $R^2$ is $C_{1-4}$alkyl (such as methyl), —OH, —$C_{1-4}$alkylene-OH (such as —CH$_2$OH), —O$C_{1-4}$alkyl (such as —OCH$_3$), or —NH$_2$, p is 1, and q is 0. In some embodiments, disclosed are compounds of formula (I-a), or salts thereof, wherein p is 1 and q is 1. In some embodiments, disclosed are compounds of formula (I-a), or salts thereof, wherein $R^2$ is methyl, $R^3$ is —CH$_3$, halogen (such as F), —OCH$_3$, or —CN, p is 1, and q is 1.

In some embodiments, disclosed are compounds of formula (I-a), or salts thereof, wherein when p is 0 and $R^1$ is phenyl, then $R^1$ is substituted with one or more $R^W$. In some embodiments, disclosed are compounds of formula (I-a), or salts thereof, wherein when $R^1$ is unsubstituted phenyl, then p is 1, 2, 3, or 4 (e.g., p is 1 or 2, or p is 1). In some embodiments, disclosed are compounds of formula (I-a), or salts thereof, wherein when p is 0, then $R^1$ is substituted with one or more $R^W$ (e.g., with one $R^W$). In some embodiments, disclosed are compounds of formula (I-a), or salts thereof, wherein when p is 0 and $R^1$ is phenyl, then $R^1$ is substituted with one or more $R^W$ (e.g., with one $R^W$). In some embodiments, disclosed are compounds of formula (I-a), or salts thereof, wherein when $R^1$ is unsubstituted, then p is 1, 2, 3, or 4 (e.g., p is 1 or 2, or p is 1). In some embodiments, disclosed are compounds of formula (I-a), or salts thereof, wherein when $R^1$ is unsubstituted phenyl, then p is 1, 2, 3, or 4 (e.g., p is 1 or 2, or p is 1). In some embodiments, disclosed are compounds of formula (I-a), or salts thereof, wherein the compound is not N-phenyl-2-(phenylsulfonamido)benzamide.

In some embodiments, the compounds of formula (I-a) are compounds of formula (I-a-1), or salts thereof,

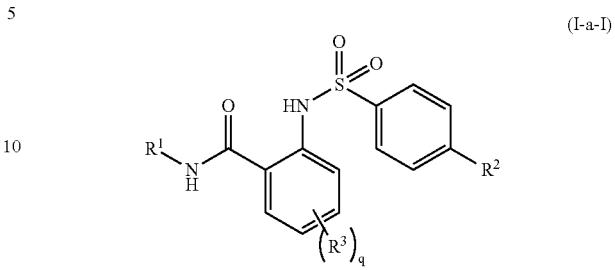

(I-a-I)

wherein:
$R^1$ is

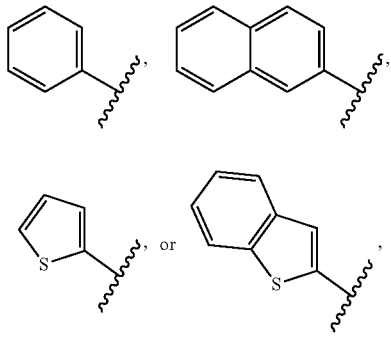 [SMILES: *c1ccccc1 ; *c1ccc2ccccc2c1 ; *c1cccs1 ; *c1cc2ccccc2s1]

each optionally substituted with halogen, $C_{1-4}$alkyl, $C_{1-4}$haloalkyl, or phenyl; or $R^1$ is

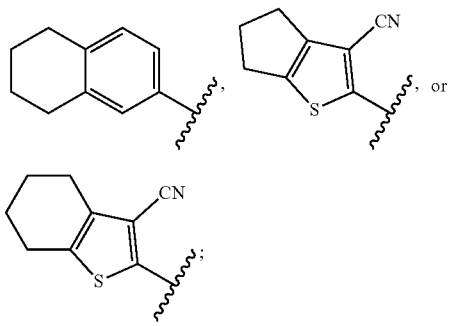 [SMILES: *c1ccc2c(c1)CCCC2 ; *c1sc2c(c1C#N)CCC2 ; *c1sc2c(c1C#N)CCCC2]

$R^2$ is halogen, $C_{1-4}$alkyl, $C_{1-4}$haloalkyl, —OH, $C_{1-4}$alkylene-OH, —O$C_{1-4}$alkyl, or —NH$_2$; and $R^3$ and q are as defined in formula (I-a).

In some embodiments, disclosed are compounds of formula (I-a-1), or salts thereof, wherein $R^1$ is

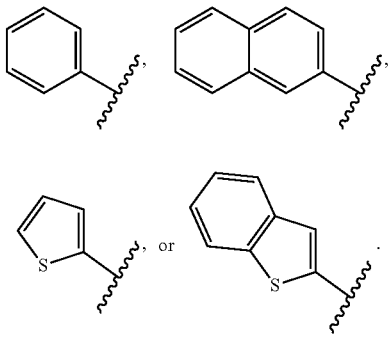 [SMILES: *c1ccccc1 ; *c1ccc2ccccc2c1 ; *c1cccs1 ; *c1cc2ccccc2s1]

In some embodiments, disclosed are compounds of formula (I-a-1), or salts thereof, wherein $R^1$ is

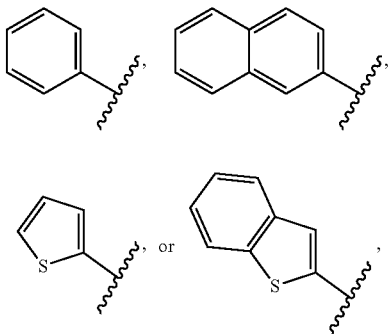 [SMILES: *c1ccccc1 ; *c1ccc2ccccc2c1 ; *c1cccs1 ; *c1cc2ccccc2s1]

each of which is substituted with halogen, $C_{1-4}$alkyl, $C_{1-4}$haloalkyl, or phenyl. In some embodiments, disclosed are compounds of formula (I-a-1), or salts thereof, wherein $R^1$ is

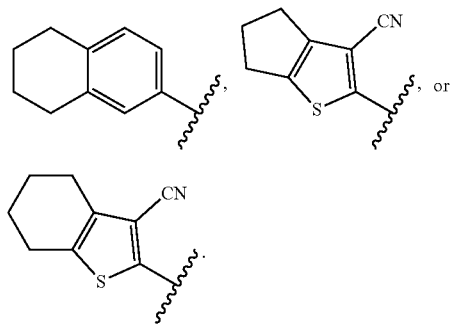 [SMILES: *c1ccc2c(c1)CCCC2 ; *c1sc2c(c1C#N)CCC2 ; *c1sc2c(c1C#N)CCCC2]

In some embodiments, disclosed are compounds of formula (I-a-1), or salts thereof, wherein $R^2$ is $C_{1-4}$alkyl (such as methyl), halogen (such as Br), or $C_{1-4}$haloalkyl (such as —CF3). In some embodiments, disclosed are compounds of formula (I-a-1), or salts thereof, wherein $R^2$ is $C_{1-4}$alkyl (such as methyl). In some embodiments, disclosed are compounds of formula (I-a-1), or salts thereof, wherein $R^2$ is —OH, —$C_{1-4}$alkylene-OH (such as —CH$_2$OH), —OC$_{1-4}$alkyl (such as —OCH$_3$), or —NH$_2$. In some embodiments, disclosed are compounds of formula (I-a-1), or salts thereof, wherein $R^2$ is $C_{1-4}$alkyl (such as methyl), halogen (such as Br), —OH, $C_{1-4}$alkylene-OH (such as —CH$_2$—OH), —OC$_{1-4}$alkyl (such as —OCH$_3$), or —NH$_2$, and q is 0. In some embodiments, disclosed are compounds of formula (I-a-1), or salts thereof, wherein $R^2$ is $C_{1-4}$alkyl (such as methyl) and q is 0. In some embodiments, disclosed are compounds of formula (I-a-1), or salts thereof, wherein $R^2$ is $C_{1-4}$alkyl (such as methyl), $R^3$ is —CH$_3$, halogen (such as F), —OCH$_3$, or —CN, and q is 1.

Suitable compounds include the following:

N-(3-cyano-5,6-dihydro-4H-cyclopenta[b]thiophen-2-yl)-2-((4-methylphenyl)sulfonamido)benzamide;
N-(3-cyano-4,5,6,7-tetrahydrobenzo[b]thiophen-2-yl)-2-((4-methylphenyl)sulfonamido)benzamide;
N-(3-cyanothiophen-2-yl)-2-((4-methylphenyl)sulfonamido)benzamide;
N-(2-cyanophenyl)-2-((4-methylphenyl)sulfonamido)benzamide;
2-((4-methylphenyl)sulfonamido)-N-phenylbenzamide;
N-(3-cyano-5,6-dihydro-4H-cyclopenta[b]thiophen-2-yl)-2-(phenylsulfonamido)benzamide;
N-(benzo[b]thiophen-2-yl)-2-((4-formylphenyl)sulfonamido)benzamide;
methyl 3-(4-(N-(2-(benzo[b]thiophen-2-ylcarbamoyl)phenyl)sulfamoyl)phenyl)propanoate;
N-(benzo[b]thiophen-2-yl)-2-((3-methylphenyl)sulfonamido)benzamide;
N-(benzo[b]thiophen-2-yl)-2-((4-(3-hydroxypropyl)phenyl)sulfonamido)benzamide;
2-([1,1'-biphenyl]-3-sulfonamido)-N-(p-tolyl)benzamide;
methyl 3-(N-(2-(p-tolylcarbamoyl)phenyl)sulfamoyl)benzoate;
3-(N-(2-(p-tolylcarbamoyl)phenyl)sulfamoyl)benzoic acid;
2-((3-acetamidophenyl)sulfonamido)-N-(p-tolyl)benzamide;
2-((3-aminophenyl)sulfonamido)-N-(p-tolyl)benzamide;
2-((3-(hydroxymethyl)phenyl)sulfonamido)-N-(p-tolyl)benzamide;
2-((3-(butylcarbamoyl)phenyl)sulfonamido)-N-(p-tolyl)benzamide;
2-((3-bromophenyl)sulfonamido)-N-(p-tolyl)benzamide;
2-((3-(butylamino)phenyl)sulfonamido)-N-(p-tolyl)benzamide;
2-((3-(hex-1-yn-1-yl)phenyl)sulfonamido)-N-(p-tolyl)benzamide;
2-((3-hexylphenyl)sulfonamido)-N-(p-tolyl)benzamide;
2-((3-(3-hydroxyprop-1-yn-1-yl)phenyl)sulfonamido)-N-(p-tolyl)benzamide;
2-((3-(3-hydroxypropyl)phenyl)sulfonamido)-N-(p-tolyl)benzamide;
N-(p-tolyl)-2-((4-(trifluoromethyl)phenyl)sulfonamido)benzamide;
2-((4-methoxyphenyl)sulfonamido)-N-(p-tolyl)benzamide;
2-((4-bromophenyl)sulfonamido)-N-(p-tolyl)benzamide;
2-([1,1'-biphenyl]-4-sulfonamido)-N-(p-tolyl)benzamide;
N-(p-tolyl)-2-((3-(trifluoromethyl)phenyl)sulfonamido)benzamide;
N-(p-tolyl)-2-((3-(trifluoromethoxy)phenyl)sulfonamido)benzamide;
N-(benzo[b]thiophen-2-yl)-2-((4-methylphenyl)sulfonamido)benzamide;
N-cyclohexyl-2-((4-methylphenyl)sulfonamido)benzamide;
2-((4-methylphenyl)sulfonamido)-N-(naphthalen-2-yl)benzamide;
2-((4-methylphenyl)sulfonamido)-N-(5,6,7,8-tetrahydronaphthalen-2-yl)benzamide;
methyl trans-4-(2-((4-methylphenyl)sulfonamido)benzamido)cyclohexane-1-carboxylate;

trans-4-(2-((4-methylphenyl)sulfonamido)benzamido)cyclohexane-1-carboxylic acid;
2-((4-methylphenyl)sulfonamido)-N-(p-tolyl)benzamide;
ethyl 2-(4-(2-((4-methylphenyl)sulfonamido)benzamido)phenyl)acetate;
N-(3-isopropylphenyl)-2-((4-methylphenyl)sulfonamido)benzamide;
ethyl 3-(2-((4-methylphenyl)sulfonamido)benzamido)benzoate;
2-(4-(2-((4-methylphenyl)sulfonamido)benzamido)phenyl)acetic acid;
3-(2-((4-methylphenyl)sulfonamido)benzamido)benzoic acid;
2-((4-methylphenyl)sulfonamido)-N-(m-tolyl)benzamide;
N-(benzo[b]thiophen-2-yl)-3-((4-methylphenyl)sulfonamido)-2-naphthamide;
2-((4-methylphenyl)sulfonamido)-N-(2-propylphenyl)benzamide;
N-(benzo[b]thiophen-2-yl)-5-methyl-2-((4-methylphenyl)sulfonamido)benzamide;
N-(3-butylphenyl)-2-((4-methylphenyl)sulfonamido)benzamide;
N-(benzo[b]thiophen-2-yl)-5-cyano-2-((4-methylphenyl)sulfonamido)benzamide;
N-(4-butylphenyl)-2-((4-methylphenyl)sulfonamido)benzamide;
N-(benzo[b]thiophen-2-yl)-2-((5,6,7,8-tetrahydronaphthalene)-2-sulfonamido)benzamide;
N-(4-hexylphenyl)-2-((4-methylphenyl)sulfonamido)benzamide;
2-((4-methylphenyl)sulfonamido)-N-(4-octylphenyl)benzamide;
methyl 6-(4-(2-((4-methylphenyl)sulfonamido)benzamido)phenyl)hexanoate;
6-(4-(2-((4-methylphenyl)sulfonamido)benzamido)phenyl)hexanoic acid;
N-(benzo[b]thiophen-2-yl)-2-((4-butylphenyl)sulfonamido)benzamide;
N-(4-(6-hydroxyhexyl)phenyl)-2-((4-methylphenyl)sulfonamido)benzamide;
N-(benzo[b]thiophen-2-yl)-2-((4-pentylphenyl)sulfonamido)benzamide;
N-(benzo[b]thiophen-2-yl)-5-butyl-2-((4-methylphenyl)sulfonamido)benzamide;
N-(4-(4-hydroxybutyl)phenyl)-2-((4-methylphenyl)sulfonamido)benzamide;
N-(4-(4-bromobutyl)phenyl)-2-((4-methylphenyl)sulfonamido)benzamide;
5-methoxy-2-((4-methylphenyl)sulfonamido)-N-(p-tolyl)benzamide;
N-(benzo[b]thiophen-2-yl)-5-methoxy-2-((4-methylphenyl)sulfonamido)benzamide;
4-methoxy-2-((4-methylphenyl)sulfonamido)-N-(p-tolyl)benzamide;
N-(benzo[b]thiophen-2-yl)-4-methoxy-2-((4-methylphenyl)sulfonamido)benzamide;
2-((3-methoxyphenyl)sulfonamido)-N-(p-tolyl)benzamide;
N-(benzo[b]thiophen-2-yl)-2-((3-methoxyphenyl)sulfonamido)benzamide;
5-hydroxy-2-((4-methylphenyl)sulfonamido)-N-(p-tolyl)benzamide;
2-((3-hydroxyphenyl)sulfonamido)-N-(p-tolyl)benzamide;
2-((3-butoxyphenyl)sulfonamido)-N-(p-tolyl)benzamide;
N-(2-bromophenyl)-2-((4-methylphenyl)sulfonamido)benzamide;
N-(3-bromophenyl)-2-((4-methylphenyl)sulfonamido)benzamide;
N-([1,1'-biphenyl]-4-yl)-2-((4-methylphenyl)sulfonamido)benzamide;
N-(2-methoxyphenyl)-2-((4-methylphenyl)sulfonamido)benzamide;
N-([1,1'-biphenyl]-3-yl)-2-((4-methylphenyl)sulfonamido)benzamide;
N-(3-methoxyphenyl)-2-((4-methylphenyl)sulfonamido)benzamide;
N-(4-methoxyphenyl)-2-((4-methylphenyl)sulfonamido)benzamide;
2-((N-ethyl-4-methylphenyl)sulfonamido)-N-(4-methoxyphenyl)benzamide;
N-(benzo[b]thiophen-2-yl)-4-fluoro-2-((4-methylphenyl)sulfonamido)benzamide;
N-(benzo[b]thiophen-2-yl)-5-fluoro-2-((4-methylphenyl)sulfonamido)benzamide;
N-benzyl-2-((4-methylphenyl)sulfonamido)benzamide;
N-(4-methoxybenzyl)-2-((4-methylphenyl)sulfonamido)benzamide; and
N-(benzo[b]thiophen-2-yl)-2-((4-methylphenyl)sulfonamido)-5-(trifluoromethyl)benzamide,
or a salt thereof.

(1) Salt Forms

A thienopyrrole compound described herein can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular thienopyrrole compound herein also includes salt forms thereof.

(2) Isomers

Certain thienopyrrole compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In some embodiments, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In some embodiments, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In some embodiments, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

The present compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

3. *Oplophorus* Luciferase-Derived Bioluminescent Complexes

The disclosed compounds may be used to inhibit *Oplophorus* luciferase-derived bioluminescent complexes. The disclosed compounds may inhibit the luciferase activity of the *Oplophorus* luciferase-derived bioluminescent complexes. The *Oplophorus* luciferase may be a wild-type *Oplophorus* luciferase or a variant of an *Oplophorus* luciferase. The *Oplophorus* luciferase may be a variant of the luciferase of SEQ ID NO: 7. *Oplophorus* luciferase variants are described in U.S. Pat. Nos. 8,557,970 and 8,669,103, each of which is incorporated herein by reference in its entirety.

The *Oplophorus* luciferase-derived bioluminescent complex may be an assembly of two or more non-luminescent peptide and/or polypeptide units (e.g., non-luminescent pair). The *Oplophorus* luciferase-derived bioluminescent complexes may include (a) a peptide comprising a peptide amino acid sequence having less than 100% sequence identity (e.g., >99%, <95%, <90%, <80%, <70%, <60%, <50%, etc.) greater than 40% (e.g., >40%, >45%, >50%, >55%, >60%, >65%, >70%, >75%, >80%, >85%, >90%, >95%, >98%, >99%) with SEQ ID NO: 2; and (b) a polypeptide comprising a polypeptide amino acid sequence having less than 100% (e.g., >99%, <95%, <90%, <80%, <70%, <60%, <50%, etc.) and greater than 40% (e.g., >40%, >45%, >50%, >55%, >60%, >65%, >70%, >75%, >80%, >85%, >90%, >95%, >98%, >99%) sequence identity with SEQ ID NO: 3, wherein the bioluminescent complex exhibits detectable luminescence in the presence of a coelenterazine substrate. In certain embodiments, the present invention provides bioluminescent complexes comprising: (a) a peptide comprising a peptide amino acid sequence having SEQ ID NO: 4 or SEQ ID NO: 6; and (b) a polypeptide comprising a polypeptide amino acid sequence having SEQ ID NO: 5, wherein the bioluminescent complex exhibits detectable luminescence in the presence of a coelenterazine substrate. Exemplary *Oplophorus* luciferase-derived bioluminescent complexes include the NanoBiT® technology that includes a NanoBiT® SmBiT non-luminescent peptide (SEQ ID NO: 6), NanoBiT® HiBiT non-luminescent peptide (SEQ ID NO: 4), and/or NanoBiT® LgBiT non-luminescent polypeptide (SEQ ID NO: 5). *Oplophorus* luciferase-derived bioluminescent complexes are described in U.S. Pat. Nos. 9,797,889 and 9,797,890, each of which is incorporated herein by reference in its entirety.

4. Coelenterazine Substrates

The disclosed compounds of the present invention may be used to inhibit luciferase activity by competing or interfering with a coelenterazine or coelenterazine-derivative substrate from binding to a luciferase. Coelenterazine substrates are a class of reporter molecules that luminesce when acted upon by luciferases and other bioluminescent proteins. Examples of coelenterazine substrates include but are not limited to: coelenterazine; coelenterazine derivatives and/or analogs such as 2-furanylmethyl-deoxy-coelenterazine (furimazine), coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl-coelenterazine, in addition to those disclosed in WO 2003/040100, U.S. Patent Publication No. 2008/0248511, and U.S. Patent Publication No. US 2012/0117667; pro-coelenterazines (i.e. compounds that are not substrates for a non-luminescent enzyme, which converts the compound to a substrate for a luciferase), quinone-masked coelenterazines, and the like. Further examples of coelenterazine substrates are described in, for example, U.S. Publication No. 2012/0107849, U.S. Publication No. 2013/0130289, U.S. patent application Ser. No. 14/608,910, and U.S. patent application Ser. No. 14/609,372, each of which is incorporated herein by reference.

5. Methods of Inhibiting *Oplophorus* Luciferase-Derived Bioluminescent Complex Activity The disclosed compounds may be used in methods to inhibit *Oplophorus* luciferase-derived bioluminescent complex, e.g., inhibit luciferase activity of the bioluminescent complex. The method may include contacting a compound disclosed herein with a cell expressing or containing an *Oplophorus* luciferase-derived bioluminescent complex or a non-luminescent peptide and/or polypeptide of the *Oplophorus* luciferase-derived bioluminescent complex, wherein the disclosed compounds may selectively inhibit the *Oplophorus* luciferase-derived bioluminescent complex. The method may include contacting a compound disclosed herein with a non-luminescent peptide and/or polypeptide of an *Oplophorus* luciferase-derived bioluminescent complex, wherein the disclosed compound inhibits the *Oplophorus* luciferase-derived bioluminescent complex when the complex has been assembled. The disclosed compounds may be used in assays that are used detect the presence or activity of enzymes using *Oplophorus* luciferase-derived bioluminescent complexes to selectively inhibit the signal from the *Oplophorus* luciferase-derived bioluminescent complexes. For example, the disclosed compounds may be used in a bioluminogenic method which employs an *Oplophorus* luciferase-derived bioluminescent complex and a coelenterazine or coelenterazine-derivative substrate to detect one or more molecules in a sample, e.g., a protein of interest (e.g., an enzyme, a binding partner, a ligand, etc.), a cofactor for an enzymatic reaction, an enzyme substrate, an enzyme inhibitor, an enzyme activator, or OH radicals, or one or more conditions, e.g., redox conditions. While the coelenterazine substrate serves as a substrate for the *Oplophorus* luciferase-derived bioluminescent complex, the disclosed compounds may serve to inhibit the luciferase-derived bioluminescent complex to selectively suppress the luminescent signal in embodiments in which such suppression may be desired, such as in applications involving temporal multiplexing of multiple bioluminescent systems or in some plate-based luminescent assays. For example, the disclosed compounds may be used to inhibit intracellular and/or extracellular *Oplophorus* luciferase-derived bioluminescent complex activities.

(1) Protein Complementation Assays

In accordance with the above, the disclosed compounds may be used to inhibit an *Oplophorus* luciferase-derived bioluminescent complex when such a bioluminescent complex is used in other methods for detecting ligand-protein and protein-protein interactions or proximity or co-localization such as the protein complementation assay (PCA) or enzyme fragmentation complementation (EFC) assay. PCA and EFC assays provide a means to detect the interaction of two interaction elements, e.g., biomolecules, polypeptides. PCA utilizes two fragments of the same protein, e.g., enzyme, that are fused to polypeptides of interest that produce light only when the two fragments of the same protein are brought into close proximity with each other via the binding interactions of their fusion partners, e.g., polypeptides of interest, and reassembly into a functional, active protein, e.g., enzyme. For example, the NANOBIT® technology (Promega Corporation) may be used to detect molecular proximity by virtue of the reassembly of a luminescent enzyme via the binding interaction of enzyme units. The NanoBiT® system may comprise two or more non-luminescent peptide and/or polypeptide units that may be expressed as a fusion with target molecule of interest. In some embodiments, the two units may comprise a NanoBiT® LgBiT non-luminescent polypeptide (NLpoly) and NanoBiT® SmBiT non-luminescent peptide (NLpep). In some embodiments, the two units may comprise a NanoBiT® LgBiT non-luminescent polypeptide (NLpoly) and NanoBiT® HiBiT non-luminescent peptide (NLpep). *Oplophorus* luciferase-derived bioluminescent complexes are described in U.S. Pat. Nos. 9,797,889 and 9,797,890, each of which is incorporated herein by reference in its entirety.

For example, an *Oplophorus* luciferase or *Oplophorus* luciferase variant can be separated into two units, e.g., non-luminescent peptide or polypeptide, e.g., at a site(s) tolerant to separation, and each unit, e.g., non-luminescent peptide or polypeptide, can be fused to one of a pair of polypeptides of interest believed to interact, e.g., FKBP and FRB. If the two polypeptides of interest do interact, the non-luminescent units, for example, then come into close proximity with each other to reassembly into a bioluminescent complex. In some embodiments, the activity of the bioluminescent complex can then be detected and measured. In some embodiments, the bioluminescent complex can be used in a more general complementation system similar to lac-Z (Langley et al., *PNAS* 72:1254-1257 (1975)) or ribonuclease S (Levit and Berger, *J. Biol. Chem.* 251:1333-1339 (1976)). In some embodiments, a luminescent enzyme unit (designated "A") known to complement with another luminescent enzyme unit ("B") can be fused to a target protein, and the resulting fusion can be monitored via luminescence in a cell or cell lysate containing fragment B. In some embodiments, the source of unit B could be the same cell (e.g., if the gene for unit B is integrated into the genome of the cell or is contained on another plasmid within the cell) or it could be a lysate or purified protein derived from another cell. In some embodiments, this same fusion protein (unit A) could be captured or immobilized using a fusion between unit B and a polypeptide such as HaloTag capable of attachment to a solid support. In some embodiments, luminescence can be used to demonstrate successful capture or to quantify the amount of material captured.

(2) Molecule Detection Assays

In accordance with the above, the disclosed compounds may be used to inhibit an *Oplophorus* luciferase-derived bioluminescent complex when such a bioluminescent complex is used in other methods for detecting a molecule of interest. For example, NANOBIT® technology (Promega Corporation) may be used to detect a molecule of interest. The NanoBiT® system may comprise two or more non-luminescent peptide and/or polypeptide units. One or more of the non-luminescent peptide and/or polypeptide units may be fused to the molecule of interest. The two units may comprise a NanoBiT® LgBiT non-luminescent polypeptide (NLpoly) and NanoBiT® HiBiT non-luminescent peptide (NLpep). In some embodiments, the NanoBiT® HiBiT NLpep may be fused to the molecule of interest. The sample comprising the NanoBiT® HiBiT NLpep fused to the molecule of interest may be contacted with the NanoBiT® LgBiT NLpoly. For example, the NanoBiT® LgBiT NLpoly may be added to a detection reagent containing a coelenterazine substrate. The resulting bioluminescence can be detected and measured, and inhibited with a compound disclosed herein. In some embodiments, the NanoBiT® LgBiT NLpoly may be fused to the molecule of interest. The sample comprising the NanoBiT® LgBiT NLpoly fused to the molecule of interest may be contacted with the NanoBiT® HiBiT NLpep. For example, the NanoBiT® HiBiT NLpep may be added to a detection reagent containing a coelenterazine substrate.

(3) Use of Cell-Impermeable Compounds

In certain embodiments, the methods disclosed herein include contacting a sample (e.g., a cell) with a mixture of a cell-permeable coelenterazine substrate and a compound described herein that is modified such that it is cell-impermeable. In such embodiments, the disclosed compounds and methods may be used to build up the initial brightness of a high-throughput screening operation assay format and then selectively inhibit any *Oplophorus* luciferase-derived bioluminescent complex that may be excreted from cells to selectively inhibit luminescence that may occur outside of the cells. Such methods may provide for a more selective signal within cells.

(4) Use of Cell-Permeable Compounds

In certain embodiments, the methods disclosed herein include contacting a sample (e.g., a cell) with a mixture of a cell-permeable coelenterazine substrate and a compound described herein that is cell-permeable. In such embodiments, the disclosed compounds can enter in to cells and selectively inhibit an *Oplophorus* luciferase-derived bioluminescent complex therein. Such methods may be advantageous in multiplexing assays that involve use of two or more luciferases and may allow for inhibition of luminescence from an *Oplophorus* luciferase-derived bioluminescent complex so as to selectively view luminescence from another luciferase inside the cell.

(5) Use with Transcriptional Reporters

The disclosed compounds may be used with genetic transcriptional reporter systems. In certain embodiments, provided is a method for measuring the activity of a promoter in a sample, wherein the promoter is operably linked to a gene encoding a non-luminescent unit, e.g., non-luminescent polypeptide, of *Oplophorus* luciferase-derived bioluminescent complex. The method includes (a) contacting the sample, which expresses a non-luminescent polypeptide of an *Oplophorus* luciferase-derived bioluminescent complex capable of forming a bioluminescent complex with a non-luminescent peptide of *Oplophorus* luciferase-derived bioluminescent complex fused to a promoter, with a coelenterazine substrate and a non-luminescent peptide of an *Oplophorus* luciferase-derived bioluminescent complex capable of forming a bioluminescent complex with a non-luminescent polypeptide of *Oplophorus* luciferase-derived bioluminescent complex; and (b) determining the activity of the promoter by measuring luminescence of the sample. The method can further include a step of contacting the sample with a compound described herein to selectively inhibit the luminescence generated from the bioluminescent complex. The promoter may be operably linked to the gene via a translational or transcriptional fusion. A biological pathway of interest, for example, may be examined by treating a cell that comprises the promoter, which is operably linked to a gene encoding a non-luminescent unit, e.g., non-luminescent polypeptide, of the *Oplophorus* luciferase-derived bioluminescent complex with an inducer agent of the pathway. This promoter activity may then be measured and monitored to study any correlation between the activity of the promoter and the pathway of interest, as well as obtain kinetic measurements relating to gene expression (e.g. inducibility, repression and activation). The compound described herein can be used to selectively inhibit the luminescence from the *Oplophorus* luciferase-derived bioluminescent complex.

(6) Multiplexing

The disclosed compounds may be used to inhibit *Oplophorus* luciferase-derived bioluminescent complexes as applied to temporal multiplexing with other luciferases and assays. In some embodiments, the *Oplophorus* luciferase-derived bioluminescent complex may be multiplexed with another enzyme (e.g., a luciferase) that emits light at a different wavelength, e.g., green firefly luciferase, e.g., *Photinus pyralis* (e.g., Luc2; Promega Corp) or red click beetle luciferase (CHROMA-LUC™ luciferase; Promega Corp.). For example, if an *Oplophorus* luciferase-derived bioluminescent complex is used as a functional reporter, then the green firefly luciferase or red CHROMA-LUC™ luciferase could be used to control for non-specific effects on genetic regulation or to normalize for transfection efficiency. In some embodiments, luminescence generated from the *Oplophorus* luciferase-derived bioluminescent complex (approximately 460 nm) and red CHROMA-LUC (approximately 610 nm) can be easily resolved using a luminometer with wavelength-discriminating filters, enabling the measurement of both signals from the same sample. In such embodiments, a compound described herein can be used to selectively inhibit the *Oplophorus* luciferase-derived bioluminescent complex such that the signal from the other luciferase can be selectively viewed.

In another example, an *Oplophorus* luciferase-derived bioluminescent complex could be used as a transcriptional reporter and paired with a luciferase that emits light at a different wavelength contained in an assay reagent. In another example, an *Oplophorus* luciferase-derived bioluminescent complex may be used with one or more additional luciferases, wherein the luminescence of each luciferase and the bioluminescent complex may be separately measured through the use of selective enzyme inhibitors. For example, the luminescence of the *Oplophorus* luciferase-derived bioluminescent complex may be measured upon addition of appropriate substrates and buffers followed by measurement of a second luciferase upon a subsequent addition of appropriate substrates and buffers and one or more compounds described herein, which are selective for the an *Oplophorus* luciferase-derived bioluminescent complex.

In some embodiments, the *Oplophorus* luciferase-derived bioluminescent complex thereof may be multiplexed with another enzyme (e.g. a luciferase) that emits light at the same wavelength. For example, NANOBIT® technology (Promega Corporation) may be multiplexed with NANO-LUC. The NanoBiT® system may comprise two or more non-luminescent peptide and/or polypeptide units. One or more of the non-luminescent peptide and/or polypeptides units may be fused to a molecule of interest. In some embodiments, the NanoBiT® LgBiT non-luminescent polypeptide and/or the NanoBiT® HiBiT non-luminescent peptide may be fused to a molecule of interest. For example, the NanoBiT® LgBiT non-luminescent polypeptide can be added to a detection reagent containing furimazine as a means to detect and quantitate a protein of interest that is fused to NanoBiT® HiBiT non-luminescent peptide. As another example, the NanoBiT® HiBiT non-luminescent peptide can be added to a detection reagent containing furimazine as a means to detect and quantitate a protein of interest that is fused to NanoBiT® LgBiT non-luminescent polypeptide. The disclosed compounds may be used to inhibit the luminescence of the resulting bioluminescent complex (e.g., the HiBiT/LgBiT complex) without inhibiting luminescence from NanoLuc.

(7) Bioluminescence Resonance Energy Transfer (BRET)

The disclosed compounds may be used in any method in which an *Oplophorus* luciferase-derived bioluminescent complex is used for detecting ligand-protein and/or protein-protein interactions. In various embodiments, the *Oplophorus* luciferase-derived bioluminescent complex may be used to transfer energy to an energy acceptor. One such method is Bioluminescence Resonance Energy Transfer (BRET). With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo.

In some embodiments, the *Oplophorus* luciferase-derived bioluminescent complex used in BRET analysis can be used to determine if two molecules are capable of binding to each other or co-localize in a cell. For example, an *Oplophorus* luciferase-derived bioluminescent complex can be used as a bioluminescence donor molecule, wherein one of the non-luminescent units is combined with a molecule or protein of interest to create a first fusion protein. In some embodiments, the non-luminescent peptide may be combined with a molecule or protein of interest to create a first fusion protein. In other embodiments, the non-luminescent polypeptide may be combined with a molecule or protein of interest to create a first fusion protein. In various embodiments, the first fusion proteins containing the non-luminescent unit, (e.g., non-luminescent peptide or non-luminescent polypeptide) of an *Oplophorus* luciferase-derived bioluminescent complex can be used in BRET analysis to detect protein/protein interaction in systems including but not limited to cell lysates, intact cells, and living animals. In various embodiments, HALOTAG can be used as a fluorescent acceptor molecule. In some embodiments, HALOTAG can be fused to a second protein of interest or to a complementing non-luminescent unit of the bioluminescent complex (e.g., non-luminescent polypeptide or non-luminescent peptide). For example, a non-luminescent polypeptide of an *Oplophorus* luciferase-derived bioluminescent complex can be fused to HALOTAG, expressed in cells or animals, and labeled with a fluorescent HALOTAG® ligand such as HALOTAG® TMR ligand. The fusion can subsequently be excited to fluoresce in the presence of a cell-permeant luminescent enzyme substrate. As another example, a non-luminescent peptide of an *Oplophorus* luciferase-derived bioluminescent complex can be fused to HaloTag, expressed in cells or animals, and labeled with a fluorescent HaloTag® ligand such as HaloTag® TMR ligand. The fusion can subsequently be excited to fluoresce in the presence of a cell-permeant luminescent enzyme substrate. In some embodiments, HALOTAG can be fused to a second protein of interest, and a complementing non-luminescent unit of the *Oplophorus* luciferase-derived bioluminescent complex (e.g., non-luminescent polypeptide or non-luminescent peptide) added via a detection reagent. In some embodiments, BRET may be performed using an *Oplophorus* luciferase-derived bioluminescent complex in combination with fluorescent proteins including but not limited to Green Fluorescent Protein (GFP) or Red Fluorescent Protein (RFP) or fluorescent labels including fluorescein, rhodamine green, Oregon green, or Alexa 488, to name a few non-limiting examples.

In some embodiments, quenching the signal from *Oplophorus* luciferase-derived bioluminescent complex can improve the signal to background ratio when using a BRET-based plate assay.

In certain embodiments, a cell-permeable compound may be used to inhibit intracellular BRET. In certain embodiments, a cell-impermeable compound may be used to inhibit extracellular BRET. In certain embodiments, a cell-impermeable compound may be used in a target engagement model.

6. Sample

The disclosed compounds may be used with samples containing biological components. The sample may comprise cells. The sample may comprise heterogeneous mixtures of components (including intact cells, cell extracts, cell lysates, bacteria, viruses, organelles, exosomes, and mixtures thereof) or a single component or homogeneous group of components (e.g., natural or synthetic amino acid, nucleic acid or carbohydrate polymers, or lipid membrane complexes). The disclosed compounds may be generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase. The cells may have been genetically modified via recombinant techniques.

7. Kits

Disclosed are kits for determining the presence or activity of an *Oplophorus* luciferase-derived bioluminescent complex. The kit may include one or more of the following: a compound or composition of the invention that may inhibit the *Oplophorus* luciferase-derived bioluminescent complex, a coelenterazine or coelenterazine-derivative substrate, and an *Oplophorus* luciferase-derived bioluminescent complex, e.g., polynucleotides for the expression of the non-luminescent peptides and/or polypeptides of the *Oplophorus* luciferase-derived bioluminescent complex, instructions for carrying out a luminescence assay, and reaction buffer(s). The reaction buffers may be present in individual formulations for the non-luciferase enzyme reactions and the luminescent enzyme reactions or in a single formulation for a single step assay. The reaction buffer may contain a non-luminescent unit of the *Oplophorus* luciferase-derived bioluminescent complex, e.g., non-luminescent peptide. The kits may also contain other inhibitors, activators and/or enhancers for the non-luciferase enzyme(s). The kits may also contain a positive and/or negative control for the assay.

8. Examples

Example 1

Syntheses of Compounds

General Procedure A: Sulfonamide Bond Formation.

To a solution of aniline derivative (1 eq) in pyridine was added substituted benzenesulfonyl chloride (1.1 eq). The solution stirred at rt for 4-18 h. The mixture was diluted with dichloromethane and washed with HCl (2 M). The organic layer was dried with sodium sulfate, filtered, concentrated, and purified with silica gel chromatography.

General Procedure B: Saponification.

To a solution of methyl or ethyl ester (1 eq) in dioxane, sodium hydroxide (2 M, 2 eq) was added. The solution was stirred at 60° C. for 2-18 h. The solution was acidified with HCl (2 M), diluted with ethyl acetate and water, and the aqueous layer extracted with ethyl acetate. The organic layers were combined, dried with sodium sulfate, filtered, concentrated, and used as crude product in the next step.

General Procedure C1: Amide Bond Formation Via Acid Chloride.

To a solution of acid chloride derivative (1 eq) in dichloroethane was added pyridine (3-5 eq) and amine (1 eq). The reaction was stirred at rt for 2-18 h. The mixture was diluted with DCM and washed with water and HCl (2 M). The organic layers were combined, dried with sodium sulfate, filtered, concentrated, and purified with silica gel chromatography.

General Procedure C2: Amide Bond Formation Via Carboxylate.

To a solution of carboxylic acid derivative (1 eq) in DMF was added amine (1.2 eq), HBTU (2 eq), and diisopropylethylamine (3 eq). The reaction was heated to 60-85° C. for 2-18 h. The mixture was diluted with ethyl acetate and washed with water and brine. The organic layers were combined, dried with sodium sulfate, filtered, concentrated, and purified with silica gel chromatography.

General Procedure D: Nitro Reduction.

To a solution of nitro derivative (1 eq) in ethyl acetate was added tin chloride hydrate (3-5 eq). The mixture was heated to reflux for 24-48 h. Saturated potassium carbonate was added and stirred at rt for 1 h. The layers were separated and the organic layer was washed with water, dried with sodium sulfate, filtered, concentrated, and purified with silica gel chromatography.

Example compounds may be prepared according to the representative synthesis methods of Scheme 1 or Scheme 2.

Scheme 1. Representative synthesis of amide analogues via acid chloride

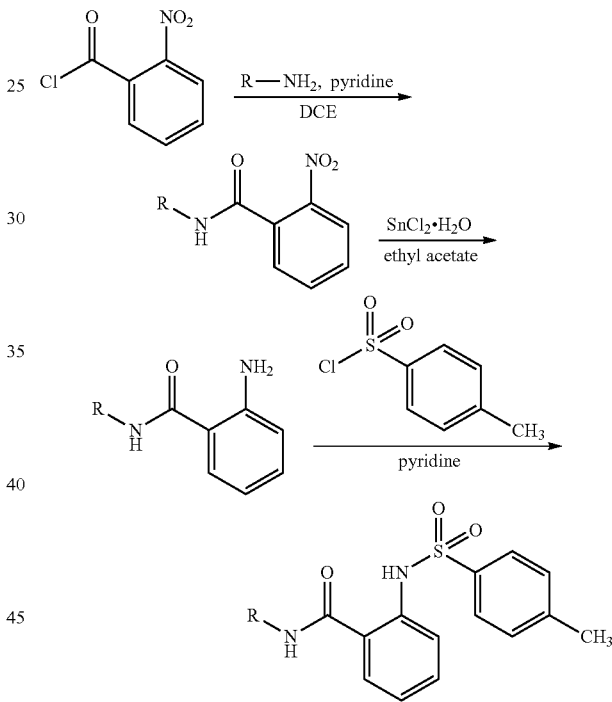

Example 2

N-(3-cyano-5,6-dihydro-4H-cyclopenta[b]thiophen-2-yl)-2-((4-methylphenyl)sulfonamido)benzamide (JRW-0998)

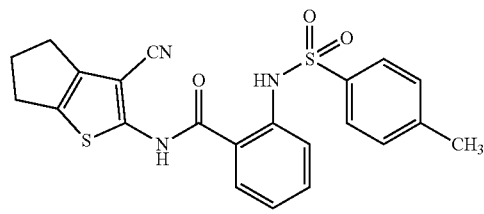 [SMILES: Cc1ccc(S(=O)(=O)Nc2ccccc2C(=O)Nc2sc3c(c2C#N)CCC3)cc1]

Step 1. N-(3-cyano-5,6-dihydro-4H-cyclopenta[b]thiophen-2-yl)-2-nitrobenzamide (JRW-0994)

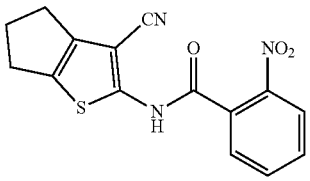 [SMILES: N#Cc1c(NC(=O)c2ccccc2[N+](=O)[O-])sc2c1CCC2]

Following general procedure C1, 2-nitrobenzoyl chloride (113 mg, 0.61 mmol) was reacted with 2-amino-5,6-dihydro-4H-cyclopenta[b]thiophene-3-carbonitrile (100 mg, 0.61 mmol) to afford the desired product (160 mg, 84%) as a yellow solid. ESI MS m/z 314 [M+H]$^+$.

Step 2. 2-amino-N-(3-cyano-5,6-dihydro-4H-cyclopenta[b]thiophen-2-yl)benzamide (JRW-0996)

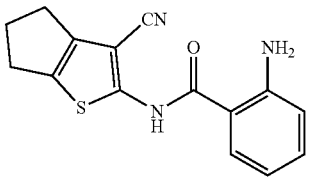 [SMILES: N#Cc1c(NC(=O)c2ccccc2N)sc2c1CCC2]

Following general procedure D, N-(3-cyano-5,6-dihydro-4H-cyclopenta[b]thiophen-2-yl)-2-nitrobenzamide (160 mg, 0.51 mmol) was reacted with tin chloride hydrate (318 mg, 1.5 mmol) to afford the desired product (80 mg, 55%) as a white solid. ESI MS m/z 284 [M+H]$^+$.

Step 3. N-(3-cyano-5,6-dihydro-4H-cyclopenta[b]thiophen-2-yl)-2-((4-methylphenyl)sulfonamido)benzamide (JRW-0998)

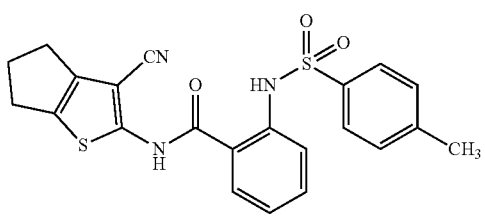 [SMILES: Cc1ccc(S(=O)(=O)Nc2ccccc2C(=O)Nc2sc3c(c2C#N)CCC3)cc1]

Following general procedure A, 2-amino-N-(3-cyano-5,6-dihydro-4H-cyclopenta[b]thiophen-2-yl)benzamide (80 mg, 0.28 mmol) was reacted with 4-methylbenzenesulfonyl chloride (54 mg, 0.28 mmol) to afford the desired product (75 mg, 61%) as a light yellow solid. ESI MS m/z 438 [M+H]$^+$.

Example 3

N-(3-cyano-4,5,6,7-tetrahydrobenzo[b]thiophen-2-yl)-2-((4-methylphenyl)sulfonamido)benzamide (JRW-1004)

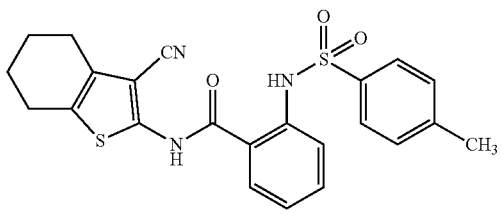 [SMILES: Cc1ccc(S(=O)(=O)Nc2ccccc2C(=O)Nc2sc3c(c2C#N)CCCC3)cc1]

Step 1. N-(3-cyano-4,5,6,7-tetrahydrobenzo[b]thiophen-2-yl)-2-nitrobenzamide (JRW-1000)

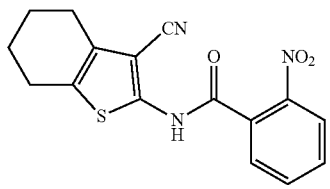 [SMILES: N#Cc1c(NC(=O)c2ccccc2[N+](=O)[O-])sc2c1CCCC2]

Following general procedure C1, 2-nitrobenzoyl chloride (187 mg, 1.0 mmol) was reacted with 2-amino-4,5,6,7-tetrahydrobenzo[b]thiophene-3-carbonitrile (180 mg, 1.0 mmol) to afford the desired product (290 mg, 87%) as a yellow solid. ESI MS m/z 328 [M+H]$^+$.

Step 2. 2-amino-N-(3-cyano-4,5,6,7-tetrahydrobenzo[b]thiophen-2-yl)benzamide (JRW-1002)

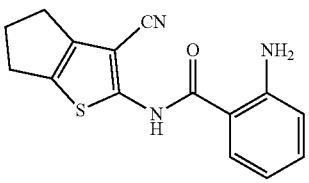 [SMILES: N#Cc1c(NC(=O)c2ccccc2N)sc2c1CCC2]

To a solution of N-(3-cyano-4,5,6,7-tetrahydrobenzo[b]thiophen-2-yl)-2-nitrobenzamide (290 mg, 0.88 mmol) in ethanol/water (8/2 mL) was added ammonium chloride (474 mg, 8.8 mmol) and iron dust (100 mg, 1.8 mmol). The suspension was heated to 60° C. for 18 h. The reaction was filtered and the filtrate was added to celite, concentrated, and purified with silica gel chromatography to afford the desired product (57 mg, 21%) as a light brown solid. ESI MS m/z 298 [M+H]$^+$.

Step 3. N-(3-cyano-4,5,6,7-tetrahydrobenzo[b]thiophen-2-yl)-2-((4-methylphenyl)sulfonamido)benzamide (JRW-1004)

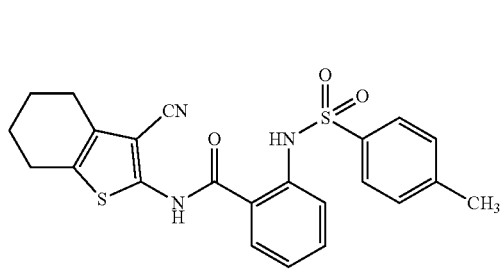 [SMILES: Cc1ccc(S(=O)(=O)Nc2ccccc2C(=O)Nc2sc3c(c2C#N)CCCC3)cc1]

Following general procedure A, 2-amino-N-(3-cyano-4,5,6,7-tetrahydrobenzo[b]thiophen-2-yl)benzamide (57 mg, 0.19 mmol) was reacted with 4-methylbenzenesulfonyl chloride (36 mg, 0.19 mmol) to afford the desired product (35 mg, 40%) as a white solid. ESI MS m/z 452 [M+H]$^+$.

Example 4

N-(3-cyanothiophen-2-yl)-2-((4-methylphenyl)sulfonamido)benzamide (JRW-1006)

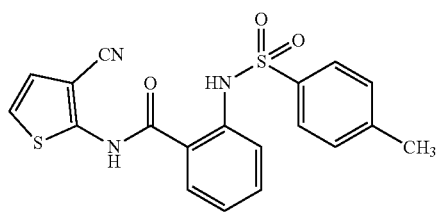 [SMILES: Cc1ccc(S(=O)(=O)Nc2ccccc2C(=O)Nc2sccc2C#N)cc1]

Step 1. N-(3-cyanothiophen-2-yl)-2-nitrobenzamide (JRW-1001)

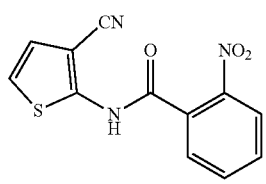 [SMILES: N#Cc1ccsc1NC(=O)c1ccccc1[N+](=O)[O-]]

Following general procedure C1, 2-nitrobenzoyl chloride (171 mg, 0.93 mmol) was reacted with 2-aminothiophene-3-carbonitrile (115 mg, 0.93 mmol) to afford the desired product (190 mg, 75%) as a light brown solid. ESI MS m/z 274 [M+H]$^+$.

Step 2. 2-amino-N-(3-cyanothiophen-2-yl)benzamide (JRW-1003)

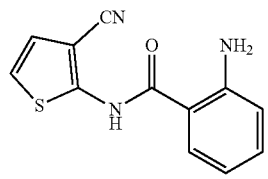 [SMILES: N#Cc1ccsc1NC(=O)c1ccccc1N]

Following general procedure D, N-(3-cyanothiophen-2-yl)-2-nitrobenzamide (190 mg, 0.69 mmol) was reacted with tin chloride hydrate (433 mg, 2.1 mmol) to afford the desired product (90 mg, 53%) as a light brown solid. ESI MS m/z 244 [M+H]$^+$.

Step 3. N-(3-cyanothiophen-2-yl)-2-((4-methylphenyl)sulfonamido)benzamide (JRW-1006)

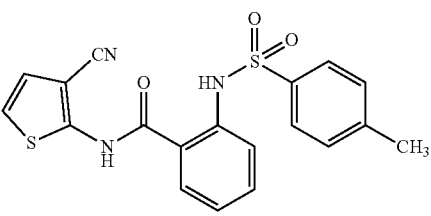 [SMILES: Cc1ccc(S(=O)(=O)Nc2ccccc2C(=O)Nc2sccc2C#N)cc1]

Following general procedure A, 2-amino-N-(3-cyanothiophen-2-yl)benzamide (90 mg, 0.37 mmol) was reacted with 4-methylbenzenesulfonyl chloride (85 mg, 0.44 mmol) to afford the desired product (97 mg, 66%) as a light brown solid. ESI MS m/z 398 [M+H]$^+$

Example 5

N-(2-cyanophenyl)-2-((4-methylphenyl)sulfonamido)benzamide (JRW-1008)

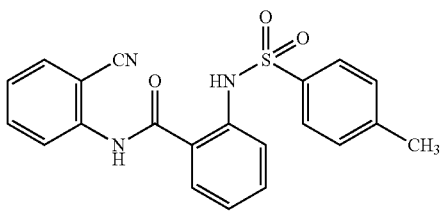 [SMILES: Cc1ccc(S(=O)(=O)Nc2ccccc2C(=O)Nc2ccccc2C#N)cc1]

Step 1. N-(2-cyanophenyl)-2-nitrobenzamide (JRW-1005)

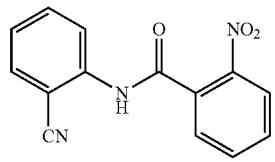 [SMILES: N#Cc1ccccc1NC(=O)c1ccccc1[N+](=O)[O-]]

Following general procedure C1, 2-nitrobenzoyl chloride (189 mg, 1.0 mmol) was reacted with 2-aminobenzonitrile (120 mg, 1.0 mmol) to afford the desired product (208 mg, 77%) as a white solid. ESI MS m/z 268 [M+H]⁺.

Step 2. 2-amino-N-(2-cyanophenyl)benzamide (JRW-1007)

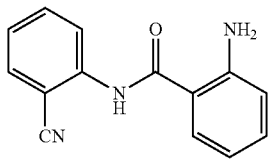 [SMILES: N#Cc1ccccc1NC(=O)c1ccccc1N]

Following general procedure D, N-(2-cyanophenyl)-2-nitrobenzamide (200 mg, 0.75 mmol) was reacted with tin chloride hydrate (466 mg, 2.2 mmol) to afford the desired product (80 mg, 45%) as a white solid. ESI MS m/z 238 [M+H]⁺.

Step 3. N-(2-cyanophenyl)-2-((4-methylphenyl)sulfonamido)benzamide (JRW-1008)

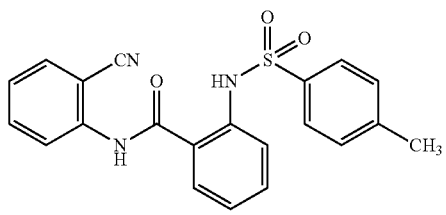 [SMILES: Cc1ccc(S(=O)(=O)Nc2ccccc2C(=O)Nc2ccccc2C#N)cc1]

Following general procedure A, 2-amino-N-(2-cyanophenyl)benzamide (80 mg, 0.34 mmol) was reacted with 4-methylbenzenesulfonyl chloride (128 mg, 0.67 mmol) to afford the desired product (91 mg, 68%) as a white solid. ESI MS m/z 392 [M+H]⁺.

Example 6

2-((4-methylphenyl)sulfonamido)-N-phenylbenzamide (JRW-1011)

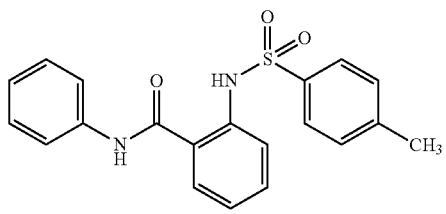 [SMILES: Cc1ccc(S(=O)(=O)Nc2ccccc2C(=O)Nc2ccccc2)cc1]

Step 1. 2-nitro-N-phenylbenzamide (JRW-1009)

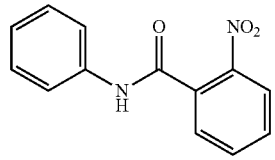 [SMILES: O=C(Nc1ccccc1)c1ccccc1[N+](=O)[O-]]

Following general procedure C1, 2-nitrobenzoyl chloride (239 mg, 1.3 mmol) was reacted with aniline (120 mg, 1.3 mmol) to afford crude product (350 mg) as a white solid. ESI MS m/z 243 [M+H]⁺.

Step 2. 2-amino-N-phenylbenzamide (JRW-1010)

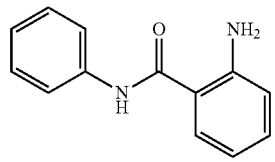

Following general procedure D, 2-nitro-N-phenylbenzamide (1.3 mmol) was reacted with tin chloride hydrate (803 mg, 3.9 mmol) to afford the desired product (200 mg, 73% over two steps) as a white solid. ESI MS m/z 213 [M+H]⁺.

Step 3. 2-((4-methylphenyl)sulfonamido)-N-phenylbenzamide (JRW-1011)

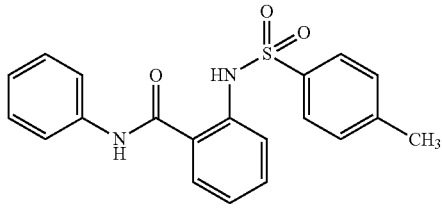 [SMILES: Cc1ccc(S(=O)(=O)Nc2ccccc2C(=O)Nc2ccccc2)cc1]

Following general procedure A, 2-amino-N-phenylbenzamide (200 mg, 0.94 mmol) was reacted with 4-methylbenzenesulfonyl chloride (359 mg, 1.9 mmol) to afford the desired product (340 mg, 98%) as a white solid. ESI MS m/z 367 [M+H]⁺.

Example 7

N-(3-cyano-5,6-dihydro-4H-cyclopenta[b]thiophen-2-yl)-2-(phenylsulfonamido)benzamide (HL-0010)

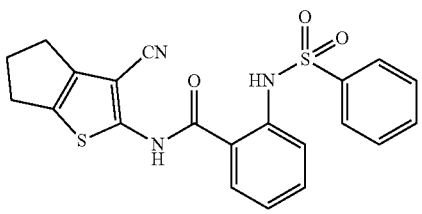 [SMILES: N#Cc1c(NC(=O)c2ccccc2NS(=O)(=O)c2ccccc2)sc2c1CCC2]

Following general procedure A, 2-amino-N-(3-cyano-5,6-dihydro-4H-cyclopenta[b]thiophen-2-yl)benzamide (40 mg, 0.14 mmol) was reacted with benzenesulfonyl chloride (30 mg, 0.17 mmol) to afford the desired product (17 mg, 26%) as a light brown solid. ESI MS m/z 424 [M+H]$^+$.

Example 8

N-(benzo[b]thiophen-2-yl)-2-((4-formylphenyl)sulfonamido)benzamide (HL-0038)

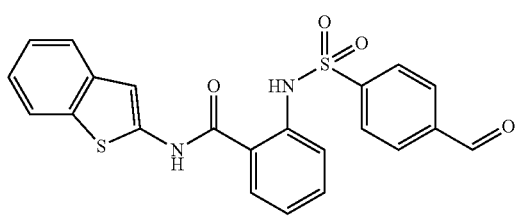 [SMILES: O=Cc1ccc(S(=O)(=O)Nc2ccccc2C(=O)Nc2cc3ccccc3s2)cc1]

Step 1. N-(benzo[b]thiophen-2-yl)-2-nitrobenzamide (HL-0028)

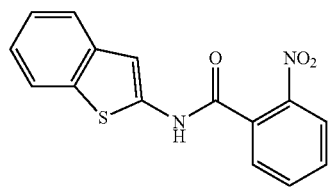 [SMILES: Nc1ccccc1C(=O)Nc1cc2ccccc2s1]

Following general procedure C1, 2-nitrobenzoyl chloride (373 mg, 2.0 mmol) was reacted with benzo[b]thiophen-2-amine (300 mg, 2.0 mmol) to afford desired product (50 mg, 8%) as a solid. ESI MS m/z 299 [M+H]$^+$.

Step 2. 2-amino-N-(benzo[b]thiophen-2-yl)benzamide (HL-0036)

Following general procedure D, N-(benzo[b]thiophen-2-yl)-2-nitrobenzamide (100 mg, 0.33 mmol) was reacted with tin chloride hydrate (209 mg, 1.0 mmol) to afford the desired product (27 mg, 30%) as a solid. ESI MS m/z 269 [M+H]$^+$.

Step 3. N-(benzo[b]thiophen-2-yl)-2-((4-formylphenyl)sulfonamido)benzamide (HL-0038)

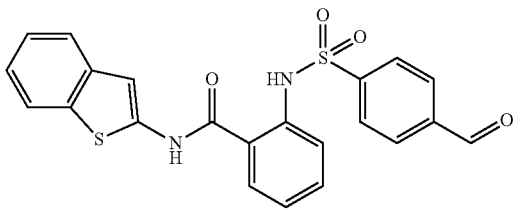 [SMILES: O=Cc1ccc(S(=O)(=O)Nc2ccccc2C(=O)Nc2cc3ccccc3s2)cc1]

Following general procedure A, 2-amino-N-(benzo[b]thiophen-2-yl)benzamide (10 mg, 0.036 mmol) was reacted with 4-formylbenzenesulfonyl chloride (7 mg, 0.037 mmol) to afford the desired product (5 mg, 31%) as a white solid. ESI MS m/z 437 [M+H]$^+$.

Example 9 methyl 3-(4-(N-(2-(benzo[b]thiophen-2-ylcarbamoyl)phenyl)sulfamoyl)phenyl)propanoate (HL-0040)

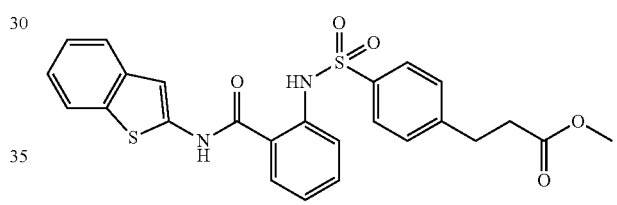

Following general procedure A, 2-amino-N-(benzo[b]thiophen-2-yl)benzamide (10 mg, 0.037 mmol) was reacted with methyl 3-(4-(chlorosulfonyl)phenyl)propanoate (10 mg, 0.037 mmol) to afford the desired product (12 mg, 63%) as a light brown solid. ESI MS m/z 495 [M+H]$^+$.

Example 10

N-(benzo[b]thiophen-2-yl)-2-((3-methylphenyl)sulfonamido)benzamide (HL-0041)

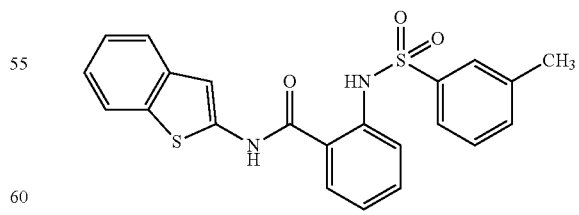

Following general procedure A, 2-amino-N-(benzo[b]thiophen-2-yl)benzamide (10 mg, 0.032 mmol) was reacted with 3-methylbenzenesulfonyl chloride (6 mg, 0.032 mmol) to afford the desired product (7 mg, 54%) as a white solid. ESI MS m/z 423 [M+H]$^+$.

Example 11

N-(benzo[b]thiophen-2-yl)-2-((4-(3-hydroxypropyl)phenyl)sulfonamido)benzamide (HL-0062)

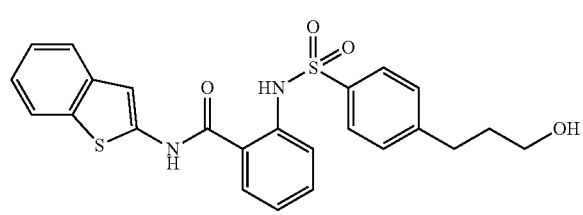 [SMILES: O=C(Nc1cc2ccccc2s1)c1ccccc1NS(=O)(=O)c1ccc(CCCO)cc1]

To a solution of methyl 3-(4-(N-(2-(benzo[b]thiophen-2-ylcarbamoyl)phenyl)sulfamoyl)phenyl)propanoate (31 mg, 0.063 mmol) in DMF (2 mL) at 0° C. was added lithium borohydride (4 mg, 0.19 mmol). The reaction warmed to rt and stirred overnight. The mixture was diluted with ethyl acetate and water, and the aqueous layer extracted with ethyl acetate. The organic layers were combined, dried with sodium sulfate, filtered, concentrated, and purified with silica gel chromatography to afford the desired product (17 mg, 60%) as a white solid. ESI MS m/z 467 [M+H]$^+$.

Example 12

2-([1,1'-biphenyl]-3-sulfonamido)-N-(p-tolyl)benzamide (JRW-1248)

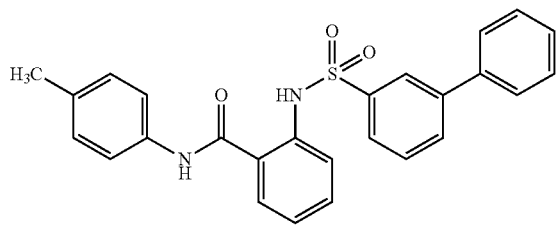 [SMILES: Cc1ccc(NC(=O)c2ccccc2NS(=O)(=O)c2cccc(-c3ccccc3)c2)cc1]

Step 1. 2-nitro-N-(p-tolyl)benzamide (JRW-1243)

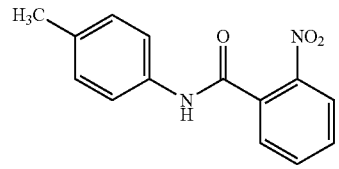 [SMILES: Cc1ccc(NC(=O)c2ccccc2[N+](=O)[O-])cc1]

Following general procedure C1, 2-nitrobenzoyl chloride (3.46 g, 18.6 mmol) was reacted with p-toluidine (2.0 g, 18.6 mmol) to afford desired product (4.6 g, 96%) as a light brown solid. ESI MS m/z 257 [M+H]$^+$.

Step 2. 2-amino-N-(p-tolyl)benzamide (JRW-1247)

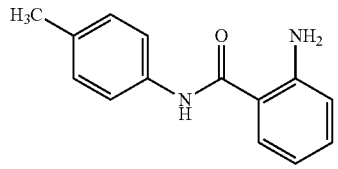 [SMILES: Cc1ccc(NC(=O)c2ccccc2N)cc1]

Following general procedure D, 2-nitro-N-(p-tolyl)benzamide (4.6 g, 18.0 mmol) was reacted with tin chloride hydrate (11.2 mg, 54.0 mmol) to afford the desired product (3.3 g, 81%) as a white solid. ESI MS m/z 227 [M+H]$^+$.

Step 3. 2-([1,1'-biphenyl]-3-sulfonamido)-N-(p-tolyl)benzamide (JRW-1248)

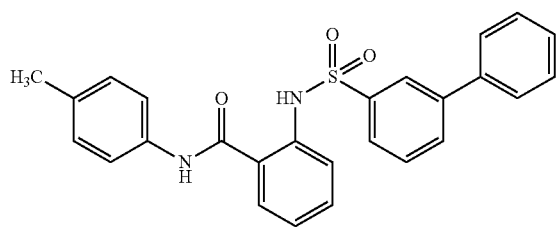 [SMILES: Cc1ccc(NC(=O)c2ccccc2NS(=O)(=O)c2cccc(-c3ccccc3)c2)cc1]

Following general procedure A, 2-amino-N-(p-tolyl)benzamide (75 mg, 0.33 mmol) was reacted with [1,1'-biphenyl]-3-sulfonyl chloride (92 mg, 0.36 mmol) to afford the desired product (85 mg, 58%) as a white solid. ESI MS m/z 443 [M+H]$^+$.

Example 13 methyl 3-(N-(2-(p-tolylcarbamoyl)phenyl)sulfamoyl)benzoate (JRW-1250)

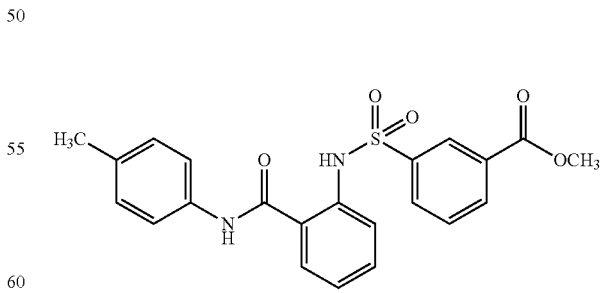

Following general procedure A, 2-amino-N-(p-tolyl)benzamide (400 mg, 1.78 mmol) was reacted with methyl 3-(chlorosulfonyl)benzoate (498 mg, 2.1 mmol) to afford the desired product (670 mg, 89%) as a white foam. ESI MS m/z 425 [M+H]$^+$.

Example 14

3-(N-(2-(p-tolylcarbamoyl)phenyl)sulfamoyl)benzoic acid (JRW-1251)

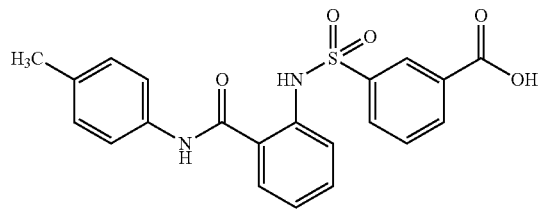 [SMILES: Cc1ccc(NC(=O)c2ccccc2NS(=O)(=O)c2cccc(C(=O)O)c2)cc1]

Following general procedure B, methyl 3-(N-(2-(p-tolylcarbamoyl)phenyl)sulfamoyl)benzoate (650 mg, 1.5 mmol) was reacted with LiOH (110 mg, 4.6 mmol) to afford the desired product (580 mg, 92%) as a white solid. ESI MS m/z 411 [M+H]+.

Example 15

2-((3-acetamidophenyl)sulfonamido)-N-(p-tolyl)benzamide (JRW-1253)

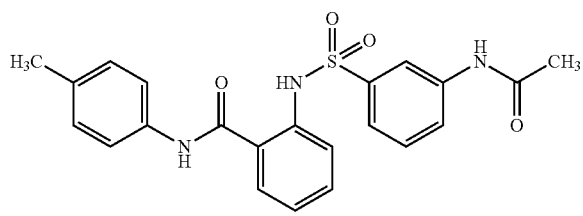 [SMILES: CC(=O)Nc1cccc(S(=O)(=O)Nc2ccccc2C(=O)Nc2ccc(C)cc2)c1]

Following general procedure A, 2-amino-N-(p-tolyl)benzamide (400 mg, 1.78 mmol) was reacted with 3-acetamidobenzenesulfonyl chloride (495 mg, 2.1 mmol) to afford the desired product (690 mg, 92%) as a white foam. ESI MS m/z 424 [M+H]+.

Example 16

2-((3-aminophenyl)sulfonamido)-N-(p-tolyl)benzamide (JRW-1255)

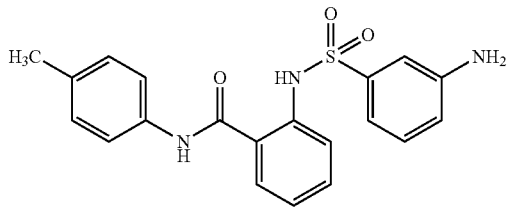 [SMILES: Cc1ccc(NC(=O)c2ccccc2NS(=O)(=O)c2cccc(N)c2)cc1]

To a solution of 2-((3-acetamidophenyl)sulfonamido)-N-(p-tolyl)benzamide (690 mg, 1.6 mmol) in methanol (20 mL) was added sodium hydroxide (5 mL, 2M). The mixture was heated to 85° C. for 5 h. The reaction was cooled, acidified to pH 5, diluted with DCM and water, and the aqueous layer extracted with DCM. The organic layers were combined, dried with sodium sulfate, filtered, concentrated, and purified with silica gel chromatography to afford the desired product (62 mg, 10%) as a white solid. ESI MS m/z 382 [M+H]+.

Example 17

2-((3-(hydroxymethyl)phenyl)sulfonamido)-N-(p-tolyl)benzamide (JRW-1261)

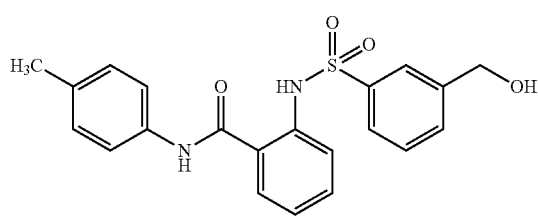 [SMILES: Cc1ccc(NC(=O)c2ccccc2NS(=O)(=O)c2cccc(CO)c2)cc1]

To a mixture of 3-(N-(2-(p-tolylcarbamoyl)phenyl)sulfamoyl)benzoic acid (54 mg, 0.13 mmol) in DCM (5 mL) was added HOBt (20 mg, 0.13 mmol) and EDC (25 mg, 0.13 mmol). The mixture stirred at rt for 30 min. The solution was concentrated to a white foam, after which the solid was dissolved in THE (10 mL) and water (0.5 mL). The solution was cooled and sodium borohydride (10 mg, 0.26 mmol) was added. The reaction was stirred at rt for 18 h, quenched with HCl, and diluted with ethyl acetate and water. The organic layers were combined, dried with sodium sulfate, filtered, concentrated, and purified with silica gel chromatography to afford the desired product (29 mg, 55%) as a white solid. ESI MS m/z 397 [M+H]+.

Example 18

2-((3-(butylcarbamoyl)phenyl)sulfonamido)-N-(p-tolyl)benzamide (JRW-1263)

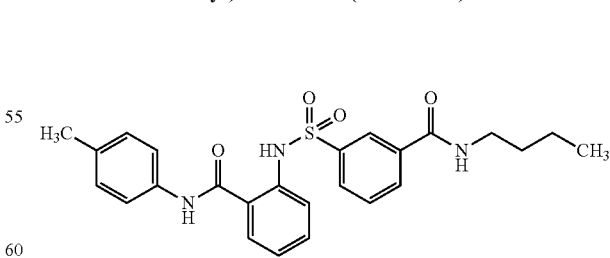

Following general procedure C2, 3-(N-(2-(p-tolylcarbamoyl)phenyl)sulfamoyl)benzoic acid (50 mg, 0.12 mmol) was reacted with butylamine (17 mg, 0.21 mmol) to afford desired product (43 mg, 76%) as a white solid. ESI MS m/z 466 [M+H]+.

Example 19

2-((3-bromophenyl)sulfonamido)-N-(p-tolyl)benzamide (JRW-1267)

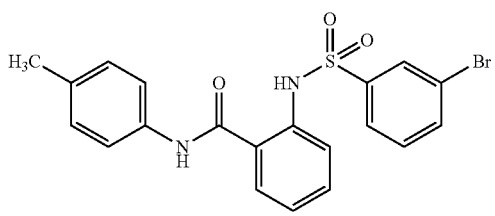 [SMILES: Cc1ccc(NC(=O)c2ccccc2NS(=O)(=O)c2cccc(Br)c2)cc1]

Following general procedure A, 2-amino-N-(p-tolyl)benzamide (350 mg, 1.5 mmol) was reacted with 3-bromobenzenesulfonyl chloride (474 mg, 1.8 mmol) to afford the desired product (620 mg, 90%) as a light brown solid. ESI MS m/z 446 [M+H]$^+$.

Example 20

2-((3-(butylamino)phenyl)sulfonamido)-N-(p-tolyl)benzamide (JRW-1269)

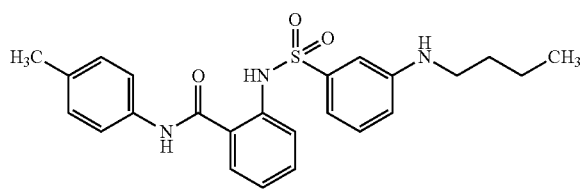 [SMILES: CCCCNc1cccc(S(=O)(=O)Nc2ccccc2C(=O)Nc2ccc(C)cc2)c1]

To a solution of 2-((3-aminophenyl)sulfonamido)-N-(p-tolyl)benzamide (50 mg, 0.13 mmol) in THF (5 mL) was added butyraldehyde (14 mg, 0.20 mmol). The mixture was stirred at rt for 30 min after which sodium triacetoxyborohydride (55 mg, 0.26 mmol) was added. The reaction stirred for at rt for 5 h, quenched with a saturated solution of NaHCO$_3$, and diluted with ethyl acetate and water. The organic layers were combined, dried with sodium sulfate, filtered, concentrated, and purified with silica gel chromatography to afford the desired product (27 mg, 47%) as a white solid. ESI MS m/z 438 [M+H]$^+$.

Example 21

2-((3-(hex-1-yn-1-yl)phenyl)sulfonamido)-N-(p-tolyl)benzamide (JRW-1270)

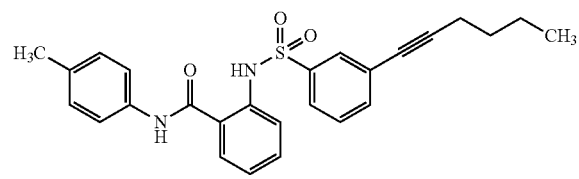 [SMILES: CCCCC#Cc1cccc(S(=O)(=O)Nc2ccccc2C(=O)Nc2ccc(C)cc2)c1]

To a solution of 2-((3-bromophenyl)sulfonamido)-N-(p-tolyl)benzamide (100 mg, 0.22 mmol) in DMF (5 mL) was added 1-hexyne (36 mg, 0.45 mmol), triethylamine (68 mg, 0.67 mmol), triphenylphosphine (6 mg, 0.022 mmol), and PdCl$_2$(PPh$_3$)$_2$ (8 mg, 0.011 mmol). The suspension was purged with nitrogen. Copper iodide (4 mg, 0.022 mmol) was added and the reaction stirred at 60° C. for 18 h. The reaction was diluted with ethyl acetate and water, extracted with ethyl acetate, the organic layers were combined, dried with sodium sulfate, filtered, concentrated, and purified with silica gel chromatography to afford the desired product (50 mg, 50%) as an orange oil. ESI MS m/z 447 [M+H]$^+$.

Example 22

2-((3-hexylphenyl)sulfonamido)-N-(p-tolyl)benzamide (JRW-1271)

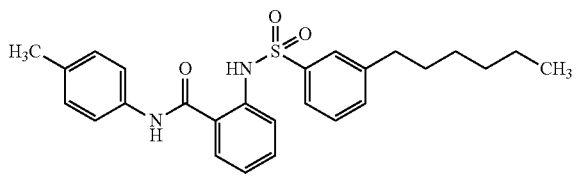 [SMILES: CCCCCCc1cccc(S(=O)(=O)Nc2ccccc2C(=O)Nc2ccc(C)cc2)c1]

To a solution of 2-((3-(hex-1-yn-1-yl)phenyl)sulfonamido)-N-(p-tolyl)benzamide (40 mg, 0.090 mmol) in ethanol (10 mL) was added palladium on carbon (5 mg). The reaction stirred at rt for 2 h with 40 psi hydrogen. The mixture was filtered through celite, concentrated, purified with silica gel chromatography to afford the desired product (25 mg, 62%) as a white solid. ESI MS m/z 451 [M+H]$^+$.

Example 23

2-((3-(3-hydroxyprop-1-yn-1-yl)phenyl)sulfonamido)-N-(p-tolyl)benzamide (JRW-1272)

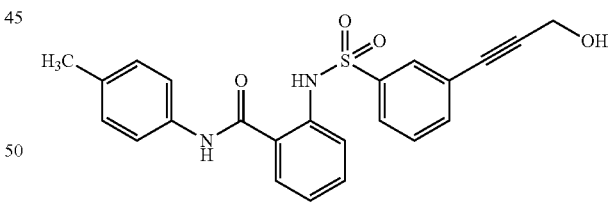

To a solution of 2-((3-bromophenyl)sulfonamido)-N-(p-tolyl)benzamide (100 mg, 0.22 mmol) in DMF (5 mL) was added propargyl alcohol (25 mg, 0.45 mmol), triethylamine (68 mg, 0.67 mmol), triphenylphosphine (6 mg, 0.022 mmol), and PdCl$_2$(PPh$_3$)$_2$ (8 mg, 0.011 mmol). The suspension was purged with nitrogen. Copper iodide (4 mg, 0.022 mmol) was added and the reaction stirred at 85° C. for 48 h. The reaction was diluted with ethyl acetate and water, extracted with ethyl acetate, the organic layers were combined, dried with sodium sulfate, filtered, concentrated, and purified with silica gel chromatography to afford the desired product (30 mg, 31%) as a light yellow gum. ESI MS m/z 421 [M+H]$^+$.

Example 24

2-((3-(3-hydroxypropyl)phenyl)sulfonamido)-N-(p-tolyl)benzamide (JRW-1275)

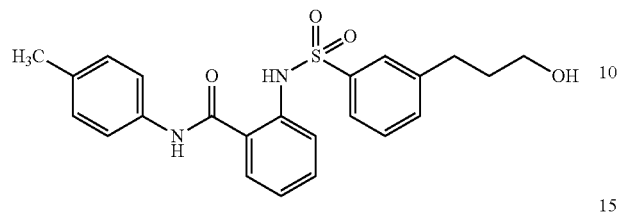

To a solution of 2-((3-(3-hydroxyprop-1-yn-1-yl)phenyl)sulfonamido)-N-(p-tolyl)benzamide (23 mg, 0.055 mmol) in ethanol (10 mL) was added palladium on carbon (5 mg). The reaction stirred at rt for 1 h with 40 psi hydrogen. The mixture was filtered through celite, concentrated, purified with silica gel chromatography to afford the desired product (17 mg, 74%) as a white solid. ESI MS m/z 425 [M+H]+.

Example 25

N-(p-tolyl)-2-((4-(trifluoromethyl)phenyl)sulfonamido)benzamide (JRW-1284)

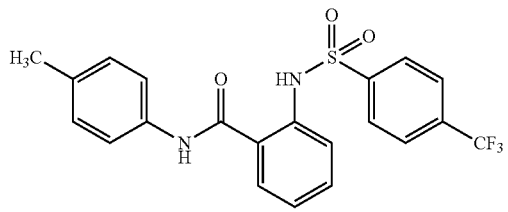 [SMILES: Cc1ccc(NC(=O)c2ccccc2NS(=O)(=O)c2ccc(C(F)(F)F)cc2)cc1]

Following general procedure A, 2-amino-N-(p-tolyl)benzamide (50 mg, 0.22 mmol) was reacted with 4-(trifluoromethyl)benzenesulfonyl chloride (64 mg, 0.26 mmol) to afford the desired product (86 mg, 89%) as a white solid. ESI MS m/z 434 [M+H]+.

Example 26

2-((4-methoxyphenyl)sulfonamido)-N-(p-tolyl)benzamide (JRW-1285)

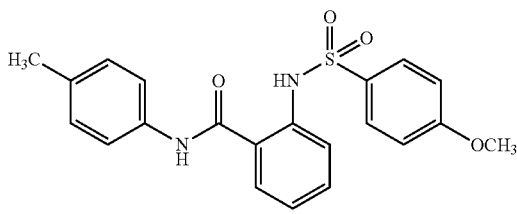 [SMILES: COc1ccc(S(=O)(=O)Nc2ccccc2C(=O)Nc2ccc(C)cc2)cc1]

Following general procedure A, 2-amino-N-(p-tolyl)benzamide (50 mg, 0.22 mmol) was reacted with 4-methoxybenzenesulfonyl chloride (55 mg, 0.26 mmol) to afford the desired product (82 mg, 94%) as a white solid. ESI MS m/z 397 [M+H]+.

Example 27

2-((4-bromophenyl)sulfonamido)-N-(p-tolyl)benzamide (JRW-1287)

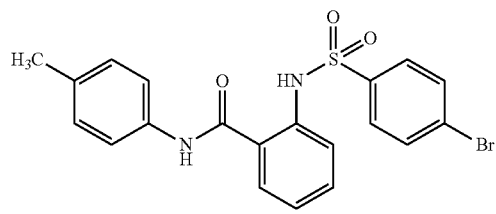 [SMILES: Cc1ccc(NC(=O)c2ccccc2NS(=O)(=O)c2ccc(Br)cc2)cc1]

Following general procedure A, 2-amino-N-(p-tolyl)benzamide (190 mg, 0.84 mmol) was reacted with 4-bromobenzenesulfonyl chloride (257 mg, 1.0 mmol) to afford the desired product (310 mg, 83%) as a white solid. ESI MS m/z 446 [M+H]+.

Example 28

2-([1,1'-biphenyl]-4-sulfonamido)-N-(p-tolyl)benzamide (JRW-1293)

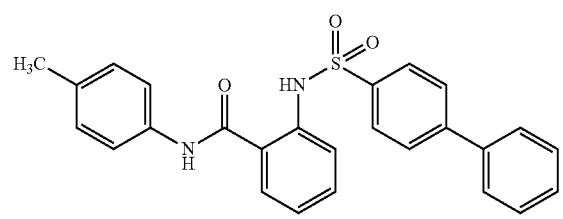 [SMILES: Cc1ccc(NC(=O)c2ccccc2NS(=O)(=O)c2ccc(-c3ccccc3)cc2)cc1]

To a solution of 2-((4-bromophenyl)sulfonamido)-N-(p-tolyl)benzamide (100 mg, 0.22 mmol) in dioxane (5 mL) was added phenylboronic acid (32 mg, 0.27 mmol) and Pd(dppf)Cl$_2$ (18 mg, 0.022 mmol). The mixture was purged with nitrogen after which aqueous Cs$_2$CO$_3$ (0.67 mL, 1 M) was added. The reaction was heated to 80° C. for 2 h. The mixture was diluted with ethyl acetate and washed with water and brine. The organic layers were combined, dried with sodium sulfate, filtered, concentrated, and purified with silica gel chromatography to afford the desired product (64 mg, 64%) as a white solid. ESI MS m/z 443 [M+H]+.

Example 29

N-(p-tolyl)-2-((3-(trifluoromethyl)phenyl)sulfonamido)benzamide (JRW-1327)

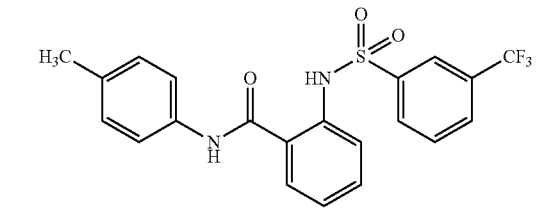 [SMILES: Cc1ccc(NC(=O)c2ccccc2NS(=O)(=O)c2cccc(C(F)(F)F)c2)cc1]

Following general procedure A, 2-amino-N-(p-tolyl)benzamide (55 mg, 0.24 mmol) was reacted with 3-(trifluoromethyl)benzenesulfonyl chloride (71 mg, 0.29 mmol) to afford the desired product (13 mg, 12%) as a white solid. ESI MS m/z 435 [M+H]$^+$.

Example 30

N-(p-tolyl)-2-((3-(trifluoromethoxy)phenyl)sulfonamido)benzamide (JRW-1328)

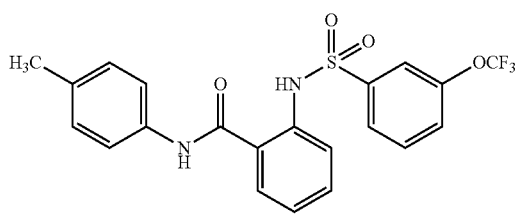 [SMILES: Cc1ccc(NC(=O)c2ccccc2NS(=O)(=O)c2cccc(OC(F)(F)F)c2)cc1]

Following general procedure A, 2-amino-N-(p-tolyl)benzamide (55 mg, 0.24 mmol) was reacted with 3-(trifluoromethoxy)benzenesulfonyl chloride (76 mg, 0.29 mmol) to afford the desired product (42 mg, 38%) as a white solid. ESI MS m/z 451 [M+H]$^+$.

Scheme 2. Representative synthesis of amide analogues via carboxylate

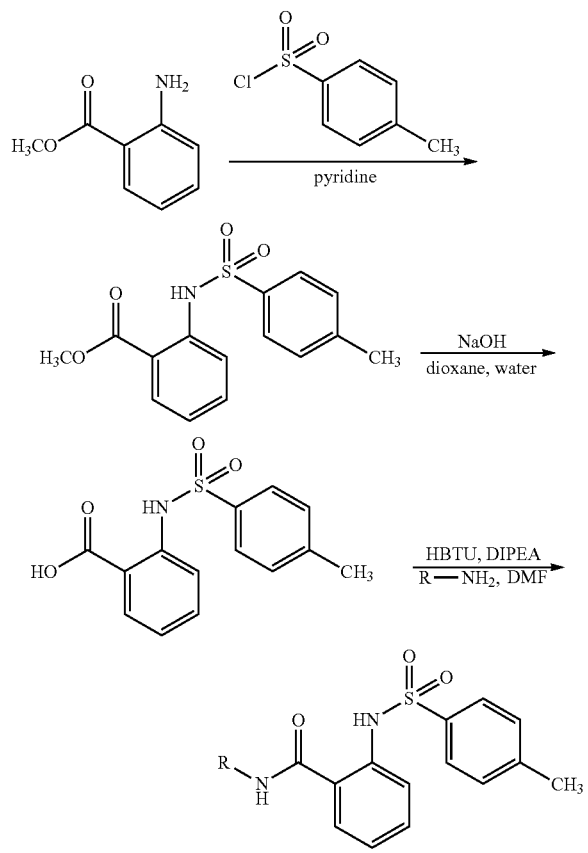

Example 31

N-(benzo[b]thiophen-2-yl)-2-((4-methylphenyl)sulfonamido)benzamide (HL-0005)

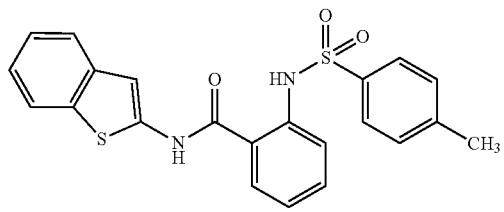 [SMILES: Cc1ccc(S(=O)(=O)Nc2ccccc2C(=O)Nc2cc3ccccc3s2)cc1]

Step 1. Methyl 2-((4-methylphenyl)sulfonamido)benzoate (HL-0001)

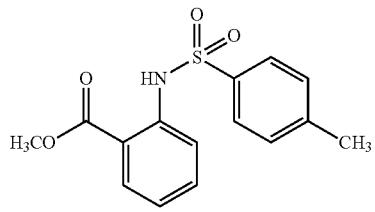 [SMILES: COC(=O)c1ccccc1NS(=O)(=O)c1ccc(C)cc1]

Following general procedure A, methyl 2-aminobenzoate (1.0 g, 6.6 mmol) was reacted with 4-methylbenzenesulfonyl chloride (1.5 g, 7.9 mmol) to afford the desired product (1.25 g, 62%) as a white solid. ESI MS m/z 306 [M+H]$^+$.

Step 2. 2-((4-methylphenyl)sulfonamido)benzoic acid (HL-0003)

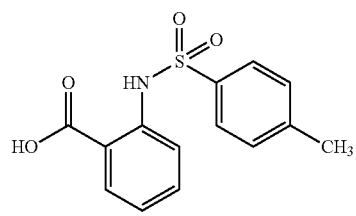 [SMILES: Cc1ccc(S(=O)(=O)Nc2ccccc2C(=O)O)cc1]

Following general procedure B, methyl 2-((4-methylphenyl)sulfonamido)benzoate (1.2 g, 4.1 mmol) was reacted with LiOH (294 mg, 12.3 mmol) to afford the desired product (1.0 g, 86%) as a white solid. ESI MS m/z 292 [M+H]$^+$.

Step 3. N-(benzo[b]thiophen-2-yl)-2-((4-methylphenyl)sulfonamido)benzamide (HL-0005)

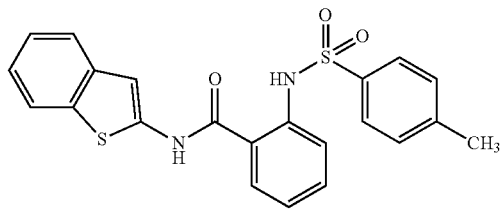 [SMILES: Cc1ccc(S(=O)(=O)Nc2ccccc2C(=O)Nc2cc3ccccc3s2)cc1]

Following general procedure C2, 2-((4-methylphenyl)sulfonamido)benzoic acid (50 mg, 0.17 mmol) was reacted with benzo[b]thiophen-2-amine (31 mg, 0.21 mmol) to afford desired product (44 mg, 96%) as a brown solid. ESI MS m/z 423 [M+H]+.

Example 32

N-cyclohexyl-2-((4-methylphenyl)sulfonamido)benzamide (HL-0006)

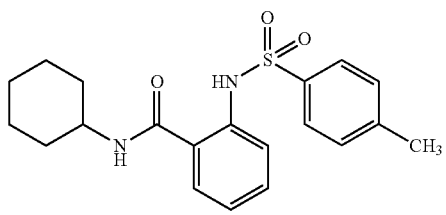 [SMILES: Cc1ccc(S(=O)(=O)Nc2ccccc2C(=O)NC2CCCCC2)cc1]

Following general procedure C2, 2-((4-methylphenyl)sulfonamido)benzoic acid (50 mg, 0.17 mmol) was reacted with cyclohexylamine (20 mg, 0.21 mmol) to afford desired product (14 mg, 22%) as a light yellow solid. ESI MS m/z 373 [M+H]+.

Example 33

2-((4-methylphenyl)sulfonamido)-N-(naphthalen-2-yl)benzamide (HL-0007)

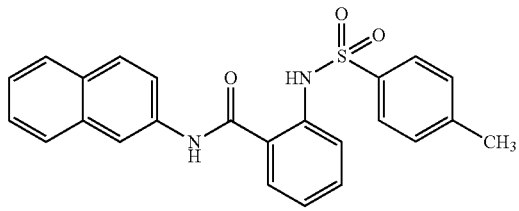 [SMILES: Cc1ccc(S(=O)(=O)Nc2ccccc2C(=O)Nc2ccc3ccccc3c2)cc1]

Following general procedure C2, 2-((4-methylphenyl)sulfonamido)benzoic acid (50 mg, 0.17 mmol) was reacted with naphthalen-2-amine (29 mg, 0.21 mmol) to afford desired product (40 mg, 54%) as a light brown solid. ESI MS m/z 417 [M+H]+.

Example 34

2-((4-methylphenyl)sulfonamido)-N-(5,6,7,8-tetrahydronaphthalen-2-yl)benzamide (HL-0008)

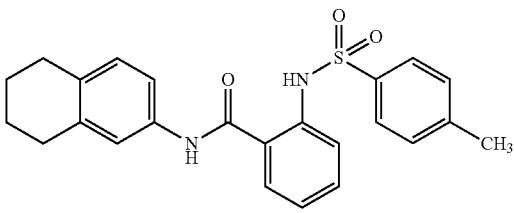 [SMILES: Cc1ccc(S(=O)(=O)Nc2ccccc2C(=O)Nc2ccc3c(c2)CCCC3)cc1]

Following general procedure C2, 2-((4-methylphenyl)sulfonamido)benzoic acid (50 mg, 0.17 mmol) was reacted with 5,6,7,8-tetrahydronaphthalen-2-amine (30 mg, 0.21 mmol) to afford desired product (33 mg, 44%) as a white solid. ESI MS m/z 421 [M+H]+.

Example 35 methyl trans-4-(2-((4-methylphenyl)sulfonamido)benzamido)cyclohexane-1-carboxylate (HL-0009)

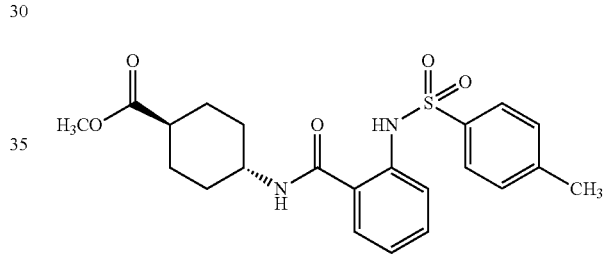

Following general procedure C2, 2-((4-methylphenyl)sulfonamido)benzoic acid (50 mg, 0.17 mmol) was reacted with methyl trans-4-aminocyclohexane-1-carboxylate HCl (40 mg, 0.21 mmol) to afford desired product (41 mg, 55%) as a solid. ESI MS m/z 431 [M+H]+.

Example 36 trans-4-(2-((4-methylphenyl)sulfonamido)benzamido)cyclohexane-1-carboxylic acid (HL-0012)

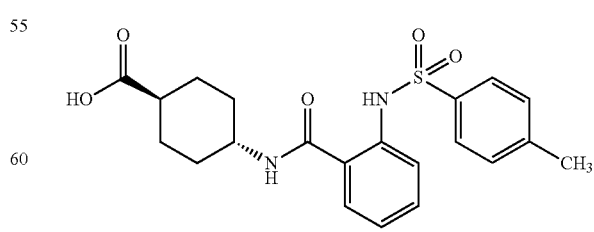

Following general procedure B, methyl trans-4-(2-((4-methylphenyl)sulfonamido)benzamido)cyclohexane-1-carboxylate (33 mg, 0.077 mmol) was reacted with LiOH (4 mg, 0.16 mmol) to afford the desired product (29 mg, 84%) as a light brown solid. ESI MS m/z 417 [M+H]⁺.

Example 37

2-((4-methylphenyl)sulfonamido)-N-(p-tolyl)benzamide (HL-0019)

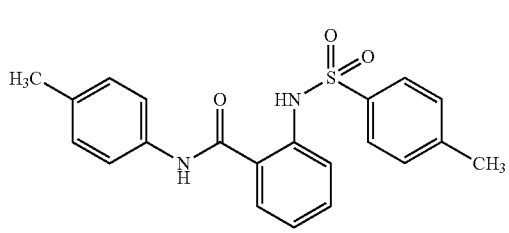

Following general procedure C2, 2-((4-methylphenyl)sulfonamido)benzoic acid (50 mg, 0.17 mmol) was reacted with 4-methyl-aniline (22 mg, 0.21 mmol) to afford desired product (34 mg, 52%) as a light brown solid. ESI MS m/z 381 [M+H]⁺.

Example 38 ethyl 2-(4-(2-((4-methylphenyl)sulfonamido)benzamido)phenyl)acetate (HL-0023)

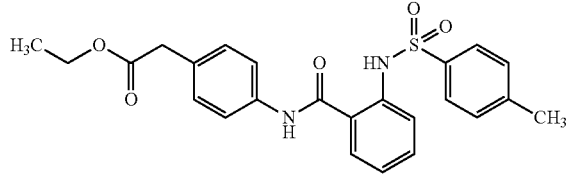 [SMILES: CCOC(=O)Cc1ccc(NC(=O)c2ccccc2NS(=O)(=O)c2ccc(C)cc2)cc1]

Following general procedure C2, 2-((4-methylphenyl)sulfonamido)benzoic acid (50 mg, 0.17 mmol) was reacted with ethyl 2-(4-aminophenyl)acetate (37 mg, 0.21 mmol) to afford desired product (32 mg, 42%) as a solid. ESI MS m/z 453 [M+H]⁺.

Example 39

N-(3-isopropylphenyl)-2-((4-methylphenyl)sulfonamido)benzamide (HL-0025)

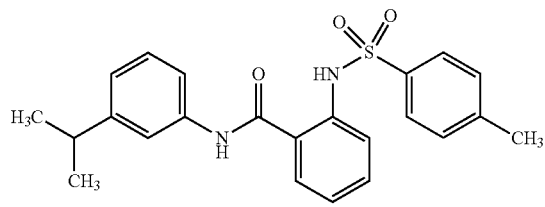 [SMILES: Cc1ccc(S(=O)(=O)Nc2ccccc2C(=O)Nc2cccc(C(C)C)c2)cc1]

Following general procedure C2, 2-((4-methylphenyl)sulfonamido)benzoic acid (50 mg, 0.17 mmol) was reacted with 3-isopropylaniline (28 mg, 0.21 mmol) to afford desired product (49 mg, 71%) as a white solid. ESI MS m/z 409 [M+H]⁺.

Example 40 ethyl 3-(2-((4-methylphenyl)sulfonamido)benzamido)benzoate (HL-0026)

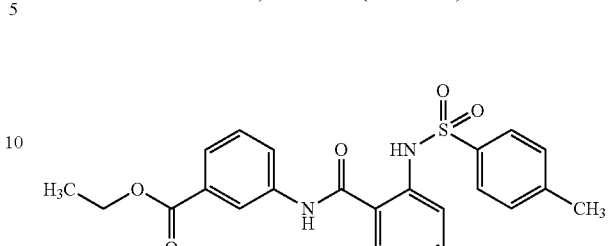

Following general procedure C2, 2-((4-methylphenyl)sulfonamido)benzoic acid (50 mg, 0.17 mmol) was reacted with ethyl 3-aminobenzoate (34 mg, 0.21 mmol) to afford desired product (50 mg, 67%) as a solid. ESI MS m/z 439 [M+H]⁺.

Example 41

2-(4-(2-((4-methylphenyl)sulfonamido)benzamido)phenyl)acetic acid (HL-0030)

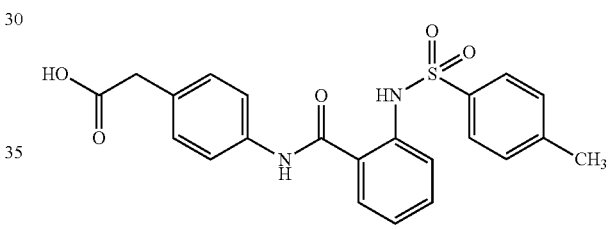

Following general procedure B, ethyl 2-(4-(2-((4-methylphenyl)sulfonamido)benzamido)phenyl)acetate (23 mg, 0.052 mmol) was reacted with LiOH (3 mg, 0.11 mmol) to afford the desired product (17 mg, 79%) as a brown solid. ESI MS m/z 425 [M+H]⁺.

Example 42

3-(2-((4-methylphenyl)sulfonamido)benzamido)benzoic acid (HL-0031)

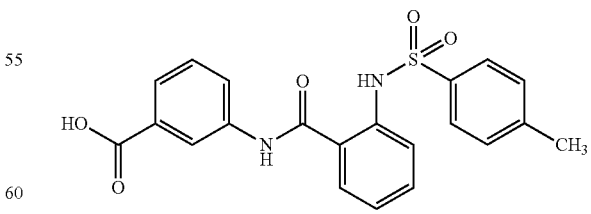

Following general procedure B, ethyl 3-(2-((4-methylphenyl)sulfonamido)benzamido)benzoate (23 mg, 0.054 mmol) was reacted with LiOH (3 mg, 0.11 mmol) to afford the desired product (12 mg, 54%) as a light yellow solid. ESI MS m/z 411 [M+H]⁺.

Example 43

2-((4-methylphenyl)sulfonamido)-N-(m-tolyl)benzamide (HL-0044)

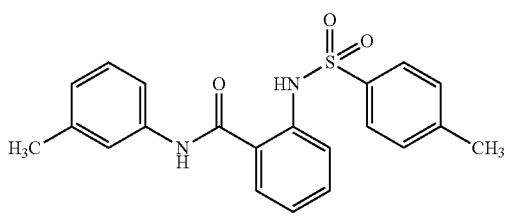

Following general procedure C2, 2-((4-methylphenyl)sulfonamido)benzoic acid (50 mg, 0.17 mmol) was reacted with m-toluidine (22 mg, 0.21 mmol) to afford desired product (57 mg, 87%) as a white solid. ESI MS m/z 381 [M+H]$^+$.

Example 44

N-(benzo[b]thiophen-2-yl)-3-((4-methylphenyl)sulfonamido)-2-naphthamide (HL-0057)

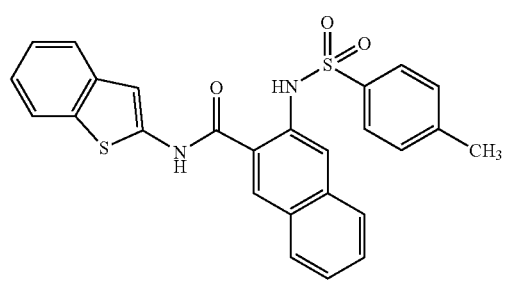 [SMILES: Cc1ccc(S(=O)(=O)Nc2cc3ccccc3cc2C(=O)Nc2cc3ccccc3s2)cc1]

Step 1. Methyl 3-((4-methylphenyl)sulfonamido)-2-naphthoate (HL-0049)

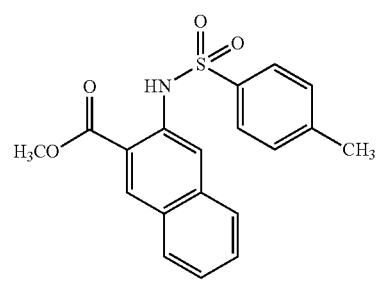 [SMILES: COC(=O)c1cc2ccccc2cc1NS(=O)(=O)c1ccc(C)cc1]

Following general procedure A, methyl 3-amino-2-naphthoate (300 mg, 1.5 mmol) was reacted with 4-methylbenzenesulfonyl chloride (341 mg, 1.8 mmol) to afford the desired product (340 mg, 64%) as a solid. ESI MS m/z 356 [M+H]+.

Step 2. 3-((4-methylphenyl)sulfonamido)-2-naphthoic acid (HL-0052)

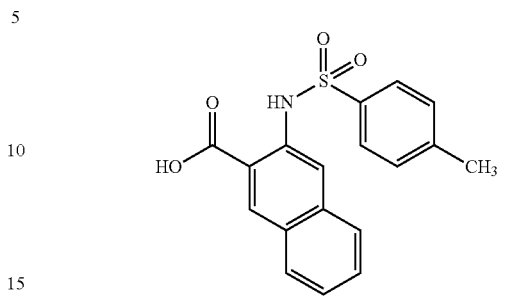

Following general procedure B, methyl 3-((4-methylphenyl)sulfonamido)-2-naphthoate (340 mg, 0.96 mmol) was reacted with LiOH (69 mg, 2.9 mmol) to afford the desired product (231 mg, 71%) as a solid. ESI MS m/z 342 [M+H]$^+$.

Step 3. N-(benzo[b]thiophen-2-yl)-3-((4-methylphenyl)sulfonamido)-2-naphthamide (HL-0057)

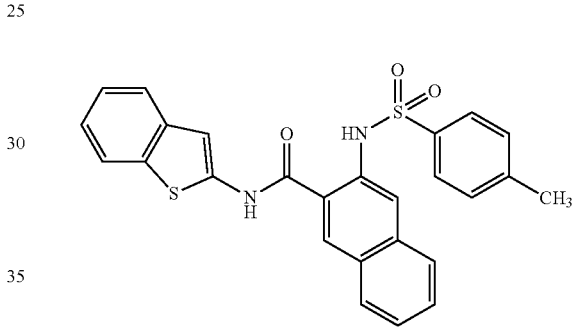

Following general procedure C2, 3-((4-methylphenyl)sulfonamido)-2-naphthoic acid (50 mg, 0.15 mmol) was reacted with benzo[b]thiophen-2-amine (22 mg, 0.15 mmol) to afford desired product (28 mg, 40%) as a light brown solid. ESI MS m/z 473 [M+H]$^+$.

Example 45

2-((4-methylphenyl)sulfonamido)-N-(2-propylphenyl)benzamide (HL-0059)

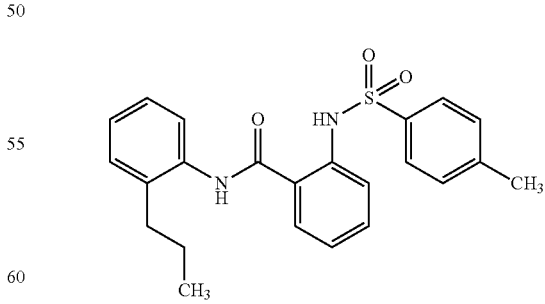

Following general procedure C2, 2-((4-methylphenyl)sulfonamido)benzoic acid (50 mg, 0.17 mmol) was reacted with 2-propylaniline (23 mg, 0.17 mmol) to afford desired product (28 mg, 40%) as a white solid. ESI MS m/z 409 [M+H]$^+$.

Example 46

N-(benzo[b]thiophen-2-yl)-5-methyl-2-((4-methylphenyl)sulfonamido)benzamide (HL-0061)

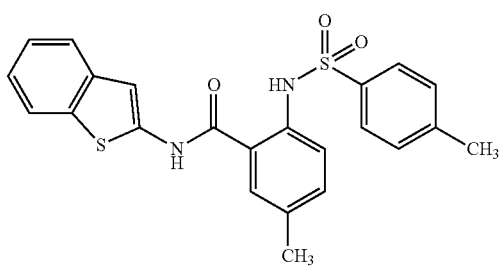

Step 1. Ethyl 5-methyl-2-((4-methylphenyl)sulfonamido)benzoate (HL-0053)

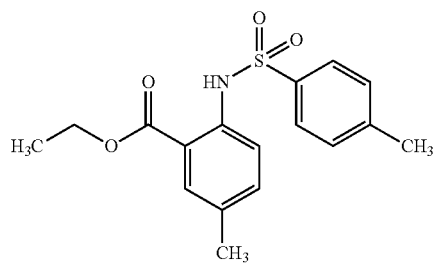 [SMILES: CCOC(=O)c1cc(C)ccc1NS(=O)(=O)c1ccc(C)cc1]

Following general procedure A, ethyl 2-amino-5-methylbenzoate (300 mg, 1.7 mmol) was reacted with 4-methylbenzenesulfonyl chloride (638 mg, 3.4 mmol) to afford the desired product (404 mg, 72%) as a solid. ESI MS m/z 334 [M+H]$^+$.

Step 2. 5-methyl-2-((4-methylphenyl)sulfonamido)benzoic acid (HL-0058)

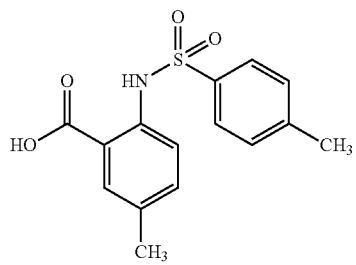

Following general procedure B, ethyl 5-methyl-2-((4-methylphenyl)sulfonamido)benzoate (404 mg, 1.2 mmol) was reacted with LiOH (87 mg, 3.6 mmol) to afford the desired product (262 mg, 71%) as a solid. ESI MS m/z 306 [M+H]$^+$.

Step 3. N-(benzo[b]thiophen-2-yl)-5-methyl-2-((4-methylphenyl)sulfonamido)benzamide (HL-0061)

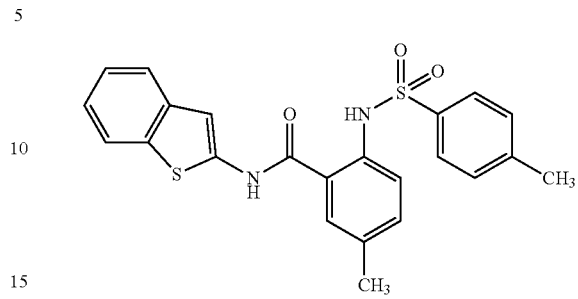

Following general procedure C2, 5-methyl-2-((4-methylphenyl)sulfonamido)benzoic acid (50 mg, 0.16 mmol) was reacted with benzo[b]thiophen-2-amine (24 mg, 0.16 mmol) to afford desired product (68 mg, 95%) as a light yellow solid. ESI MS m/z 437 [M+H]$^+$.

Example 47

N-(3-butylphenyl)-2-((4-methylphenyl)sulfonamido)benzamide (HL-0070)

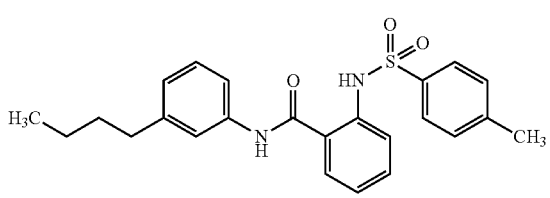 [SMILES: CCCCc1cccc(NC(=O)c2ccccc2NS(=O)(=O)c2ccc(C)cc2)c1]

Following general procedure C2, 2-((4-methylphenyl)sulfonamido)benzoic acid (50 mg, 0.17 mmol) was reacted with 3-butylaniline (25 mg, 0.17 mmol) to afford desired product (18 mg, 25%) as a white solid. ESI MS m/z 423 [M+H]$^+$.

Example 48

N-(benzo[b]thiophen-2-yl)-5-cyano-2-((4-methylphenyl)sulfonamido)benzamide (HL-0071)

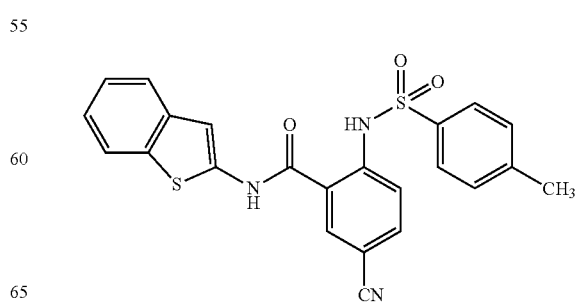

Step 1. Methyl 5-cyano-2-((4-methylphenyl)sulfonamido)benzoate (HL-0056)

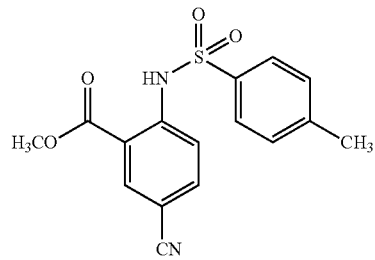 [SMILES: COC(=O)c1cc(C#N)ccc1NS(=O)(=O)c1ccc(C)cc1]

Following general procedure A, methyl 2-amino-5-cyanobenzoate (300 mg, 1.7 mmol) was reacted with 4-methylbenzenesulfonyl chloride (649 mg, 3.4 mmol) to afford the desired product (360 mg, 64%) as a solid. ESI MS m/z 331 [M+H]$^+$.

Step 2. 5-cyano-2-((4-methylphenyl)sulfonamido)benzoic acid (HL-0060)

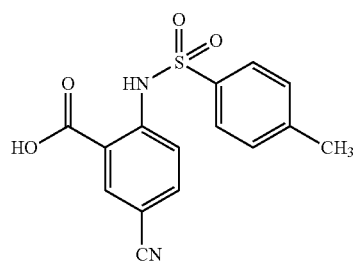 [SMILES: Cc1ccc(S(=O)(=O)Nc2ccc(C#N)cc2C(=O)O)cc1]

Following general procedure B, methyl 5-cyano-2-((4-methylphenyl)sulfonamido)benzoate (360 mg, 1.1 mmol) was reacted with LiOH (78 mg, 3.3 mmol) to afford the desired product (140 mg, 41%) as a solid. ESI MS m/z 317 [M+H]$^+$.

Step 3. N-(benzo[b]thiophen-2-yl)-5-cyano-2-((4-methylphenyl)sulfonamido)benzamide (HL-0071)

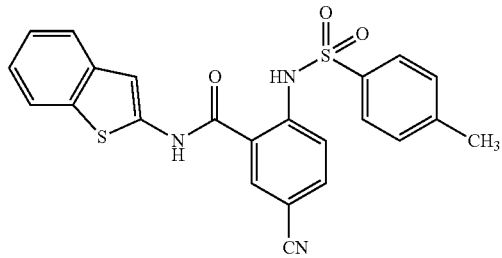 [SMILES: Cc1ccc(S(=O)(=O)Nc2ccc(C#N)cc2C(=O)Nc2cc3ccccc3s2)cc1]

Following general procedure C2, 5-cyano-2-((4-methylphenyl)sulfonamido)benzoic acid (92 mg, 0.29 mmol) was reacted with benzo[b]thiophen-2-amine (43 mg, 0.29 mmol) to afford desired product (47 mg, 36%) as a light brown solid. ESI MS m/z 448 [M+H]$^+$.

Example 49

N-(4-butylphenyl)-2-((4-methylphenyl)sulfonamido)benzamide (JRW-1076)

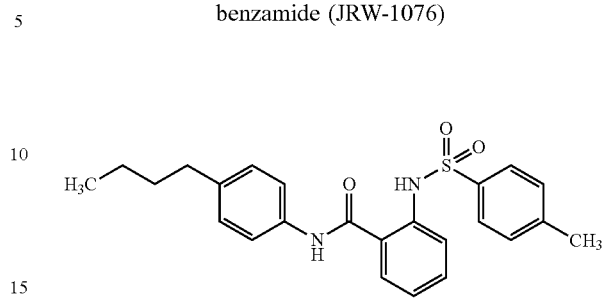

Following general procedure C2, 2-((4-methylphenyl)sulfonamido)benzoic acid (55 mg, 0.19 mmol) was reacted with 4-butylaniline (42 mg, 0.28 mmol) to afford desired product (68 mg, 86%) as a light brown oil. ESI MS m/z 423 [M+H]$^+$.

Example 50

N-(benzo[b]thiophen-2-yl)-2-((5,6,7,8-tetrahydronaphthalene)-2-sulfonamido)benzamide (JRW-1077)

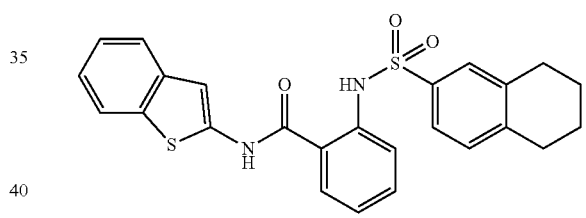

Step 1. Methyl 2-((5,6,7,8-tetrahydronaphthalene)-2-sulfonamido)benzoate (HL-0068)

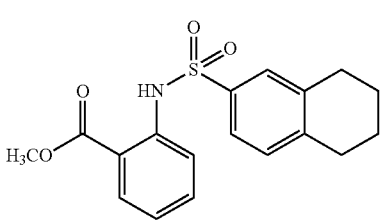 [SMILES: COC(=O)c1ccccc1NS(=O)(=O)c1ccc2c(c1)CCCC2]

Following general procedure A, methyl 2-aminobenzoate (200 mg, 1.7 mmol) was reacted with 5,6,7,8-tetrahydronaphthalene-2-sulfonyl chloride (366 mg, 1.6 mmol) to afford the desired product (289 mg, 63%) as a solid. ESI MS m/z 346 [M+H]$^+$.

Step 2. 2-((5,6,7,8-tetrahydronaphthalene)-2-sulfonamido)benzoic acid (HL-0072)

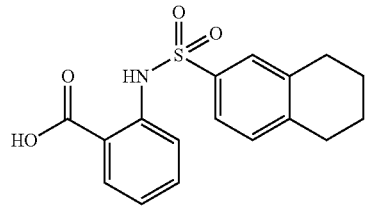 [SMILES: O=C(O)c1ccccc1NS(=O)(=O)c1ccc2c(c1)CCCC2]

Following general procedure B, methyl 2-((5,6,7,8-tetrahydronaphthalene)-2-sulfonamido)benzoate (289 mg, 0.84 mmol) was reacted with LiOH (60 mg, 2.5 mmol) to afford the desired product (264 mg, 95%) as a solid. ESI MS m/z 332 [M+H]$^+$.

Step 3. N-(benzo[b]thiophen-2-yl)-2-((5,6,7,8-tetrahydronaphthalene)-2-sulfonamido)benzamide (JRW-1077)

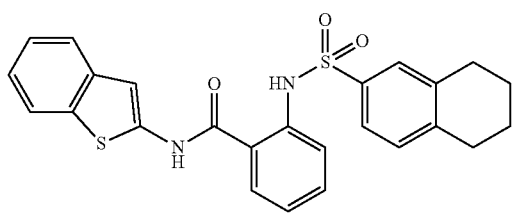 [SMILES: O=C(Nc1cc2ccccc2s1)c1ccccc1NS(=O)(=O)c1ccc2c(c1)CCCC2]

Following general procedure C2, 2-((5,6,7,8-tetrahydronaphthalene)-2-sulfonamido)benzoic acid (50 mg, 0.15 mmol) was reacted with benzo[b]thiophen-2-amine (27 mg, 0.18 mmol) to afford desired product (18 mg, 26%) as a brown oil. ESI MS m/z 463 [M+H]$^+$.

Example 51

N-(4-hexylphenyl)-2-((4-methylphenyl)sulfonamido)benzamide (JRW-1090)

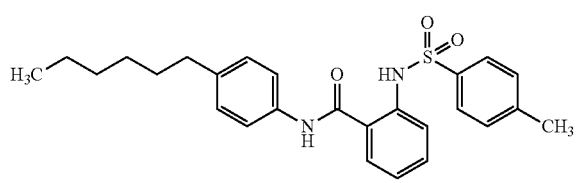 [SMILES: CCCCCCc1ccc(NC(=O)c2ccccc2NS(=O)(=O)c2ccc(C)cc2)cc1]

Following general procedure C2, 2-((4-methylphenyl)sulfonamido)benzoic acid (50 mg, 0.17 mmol) was reacted with 4-hexylaniline (36 mg, 0.21 mmol) to afford desired product (61 mg, 79%) as a white solid. ESI MS m/z 451 [M+H]$^+$.

Example 52

2-((4-methylphenyl)sulfonamido)-N-(4-octylphenyl)benzamide (JRW-1091)

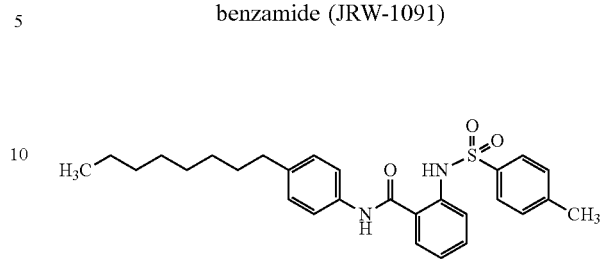

Following general procedure C2, 2-((4-methylphenyl)sulfonamido)benzoic acid (50 mg, 0.17 mmol) was reacted with 4-octylaniline (42 mg, 0.21 mmol) to afford desired product (67 mg, 81%) as a white solid. ESI MS m/z 479 [M+H]$^+$.

Example 53 methyl 6-(4-(2-((4-methylphenyl)sulfonamido)benzamido)phenyl)hexanoate (JRW-1107)

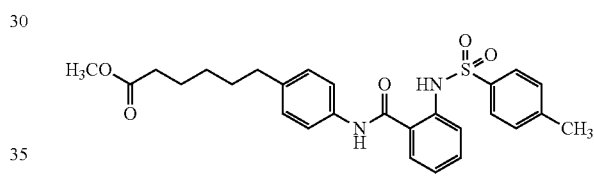

Following general procedure C2, 2-((4-methylphenyl)sulfonamido)benzoic acid (50 mg, 0.17 mmol) was reacted with methyl 6-(4-aminophenyl)hexanoate (45 mg, 0.21 mmol) to afford desired product (65 mg, 76%) as an orange oil. ESI MS m/z 479 [M+H]$^+$.

Example 54

6-(4-(2-((4-methylphenyl)sulfonamido)benzamido)phenyl)hexanoic acid (JRW-1110)

Following general procedure B, methyl 6-(4-(2-((4-methylphenyl)sulfonamido)benzamido)phenyl)hexanoate (55 mg, 0.11 mmol) was reacted with LiOH (8 mg, 0.33 mmol) to afford the desired product (50 mg, 94%) as a light brown solid. ESI MS m/z 481 [M+H]$^+$.

Example 55

N-(benzo[b]thiophen-2-yl)-2-((4-butylphenyl)sulfonamido)benzamide (JRW-1114)

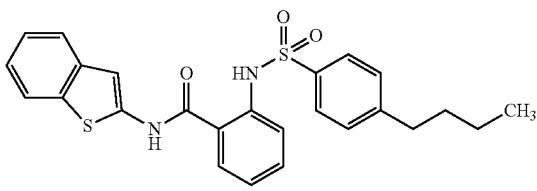 [SMILES: CCCCc1ccc(S(=O)(=O)Nc2ccccc2C(=O)Nc2cc3ccccc3s2)cc1]

Step 1. Methyl 2-((4-butylphenyl)sulfonamido)benzoate (JRW-1111)

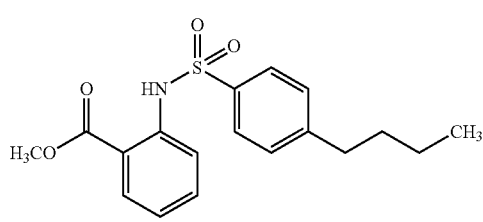 [SMILES: CCCCc1ccc(S(=O)(=O)Nc2ccccc2C(=O)OC)cc1]

Following general procedure A, methyl 2-aminobenzoate (1.0 g, 6.6 mmol) was reacted with 4-butylbenzenesulfonyl chloride (1.7 g, 7.3 mmol) to afford crude product as a light brown oil. ESI MS m/z 348 [M+H]$^+$.

Step 2. 2-((4-butylphenyl)sulfonamido)benzoic acid (JRW-1112)

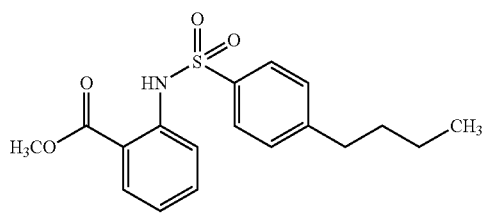 [SMILES: CCCCc1ccc(S(=O)(=O)Nc2ccccc2C(=O)OC)cc1]

Step 3. N-(benzo[b]thiophen-2-yl)-2-((4-butylphenyl)sulfonamido)benzamide (JRW-1114)

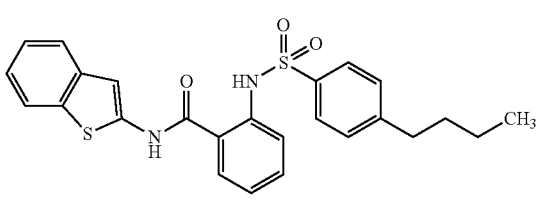 [SMILES: CCCCc1ccc(S(=O)(=O)Nc2ccccc2C(=O)Nc2cc3ccccc3s2)cc1]

Following general procedure C2, 2-((4-butylphenyl)sulfonamido)benzoic acid (120 mg, 0.36 mmol) was reacted with benzo[b]thiophen-2-amine (54 mg, 0.36 mmol) to afford desired product (25 mg, 15%) as an off white solid. ESI MS m/z 465 [M+H]$^+$.

Example 56

N-(4-(6-hydroxyhexyl)phenyl)-2-((4-methylphenyl)sulfonamido)benzamide (JRW-1120)

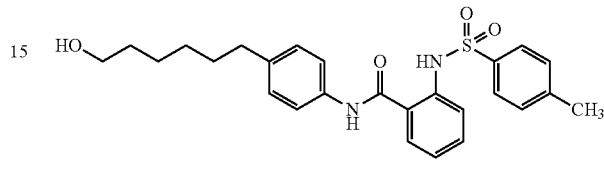

Following general procedure C2, 2-((4-methylphenyl)sulfonamido)benzoic acid (150 mg, 0.51 mmol) was reacted with 6-(4-aminophenyl)hexan-1-ol (100 mg, 0.51 mmol) to afford desired product (60 mg, 25%) as a white foam. ESI MS m/z 467 [M+H]$^+$.

Example 57

N-(benzo[b]thiophen-2-yl)-2-((4-pentylphenyl)sulfonamido)benzamide (JRW-1121)

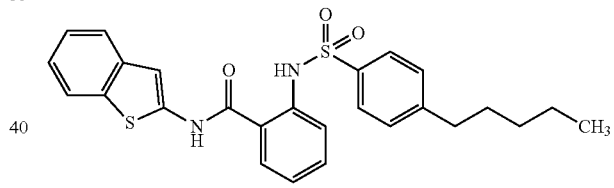

Step 1. Methyl 2-((4-pentylphenyl)sulfonamido)benzoate (JRW-1115)

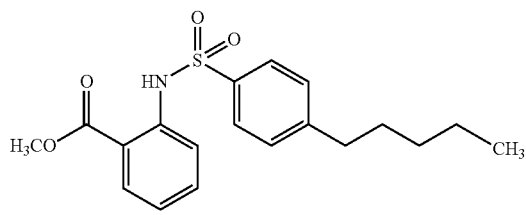 [SMILES: CCCCCc1ccc(S(=O)(=O)Nc2ccccc2C(=O)OC)cc1]

Following general procedure A, methyl 2-aminobenzoate (1.0 g, 6.6 mmol) was reacted with 4-pentylbenzenesulfonyl chloride (1.8 g, 7.3 mmol) to afford crude product (2.3 g) as an orange oil. ESI MS m/z 362 [M+H]$^+$.

Step 2. 2-((4-pentylphenyl)sulfonamido)benzoic acid (JRW-1116)

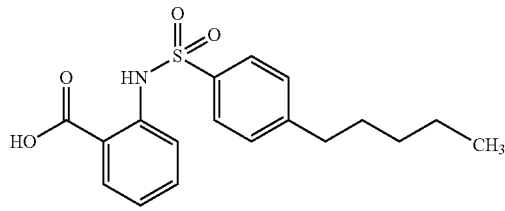 [SMILES: CCCCCc1ccc(S(=O)(=O)Nc2ccccc2C(=O)O)cc1]

Following general procedure B, methyl 2-((4-pentylphenyl)sulfonamido)benzoate (2.3 g, 6.4 mmol) was reacted with NaOH (6.4 mL, 2M, 12.7 mmol) to afford crude product (2.2 g) as a light pink solid. ESI MS m/z 348 [M+H]$^+$.

Step 3. N-(benzo[b]thiophen-2-yl)-2-((4-pentylphenyl)sulfonamido)benzamide (JRW-1121)

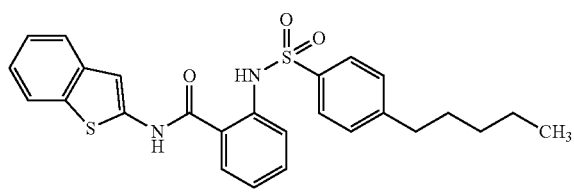 [SMILES: CCCCCc1ccc(S(=O)(=O)Nc2ccccc2C(=O)Nc2cc3ccccc3s2)cc1]

Following general procedure C2, 2-((4-pentylphenyl)sulfonamido)benzoic acid (100 mg, 0.29 mmol) was reacted with benzo[b]thiophen-2-amine (34 mg, 0.23 mmol) to afford desired product (57 mg, 41%) as an orange foam. ESI MS m/z 479 [M+H]$^+$.

Example 58

N-(benzo[b]thiophen-2-yl)-5-butyl-2-((4-methylphenyl)sulfonamido)benzamide (JRW-1146)

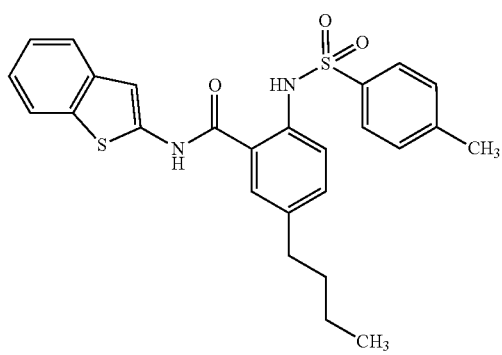 [SMILES: CCCCc1ccc(NS(=O)(=O)c2ccc(C)cc2)c(C(=O)Nc2cc3ccccc3s2)c1]

Step 1. 5-butyl-2-((4-methylphenyl)sulfonamido)benzoic acid (JRW-1142)

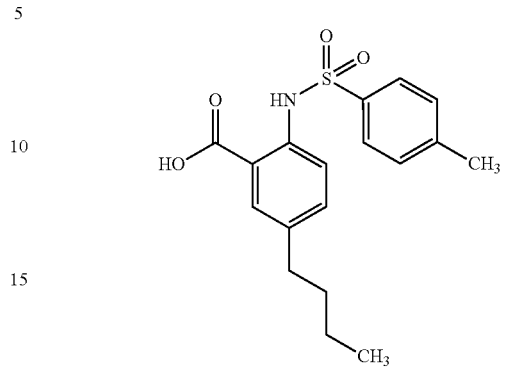

Following general procedure A, 2-amino-5-butylbenzoic acid (220 mg, 1.1 mmol) was reacted with 4-methylbenzenesulfonyl chloride (325 mg, 1.7 mmol) to afford desired product (275 mg, 69%) as a brown solid. ESI MS m/z 348 [M+H]$^+$.

Step 2. N-(benzo[b]thiophen-2-yl)-5-butyl-2-((4-methylphenyl)sulfonamido)benzamide (JRW-1146)

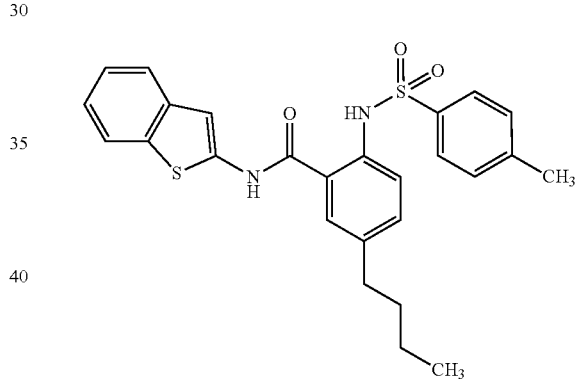

Following general procedure C2, 5-butyl-2-((4-methylphenyl)sulfonamido)benzoic acid (275 mg, 0.79 mmol) was reacted with benzo[b]thiophen-2-amine (118 mg, 0.79 mmol) to afford desired product (30 mg, 8%) as a brown solid. ESI MS m/z 479 [M+H]$^+$.

Example 59

N-(4-(4-hydroxybutyl)phenyl)-2-((4-methylphenyl)sulfonamido)benzamide (JRW-1150)

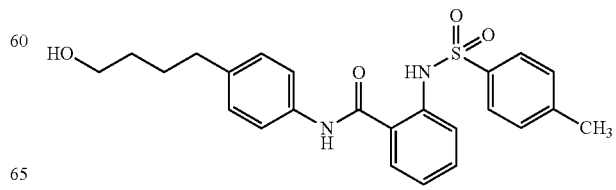

Following general procedure C2, 2-((4-methylphenyl)sulfonamido)benzoic acid (250 mg, 0.86 mmol) was reacted with 4-(4-aminophenyl)butan-1-ol (170 mg, 1.0 mmol) to afford desired product (140 mg, 37%) as a an oil. ESI MS m/z 439 [M+H]+.

Example 60

N-(4-(4-bromobutyl)phenyl)-2-((4-methylphenyl)sulfonamido)benzamide (JRW-1152)

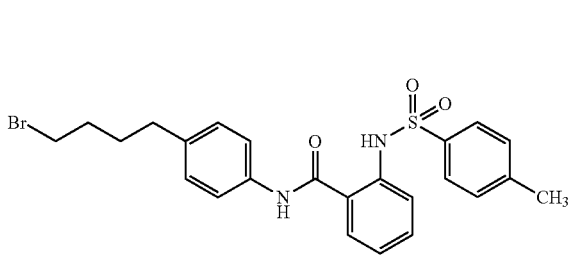 [SMILES: Cc1ccc(S(=O)(=O)Nc2ccccc2C(=O)Nc2ccc(CCCCBr)cc2)cc1]

To a solution of N-(4-(4-hydroxybutyl)phenyl)-2-((4-methylphenyl)sulfonamido)benzamide (40 mg, 0.091 mmol) in DCM (5 mL) was added carbon tetrabromide (60 mg, 0.18 mmol) and triphenylphosphine (47 mg, 0.18 mmol). The reaction stirred at rt overnight. The mixture was diluted with ethyl acetate and water, and the aqueous layer extracted with ethyl acetate. The organic layers were combined, dried with sodium sulfate, filtered, concentrated, and purified with silica gel chromatography to afford the desired product (18 mg, 40%) as a clear oil. ESI MS m/z 502 [M+H]+.

Example 61

5-methoxy-2-((4-methylphenyl)sulfonamido)-N-(p-tolyl)benzamide (JRW-1166)

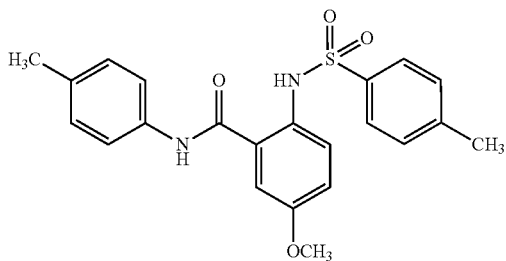

Step 1. Methyl 5-methoxy-2-((4-methylphenyl)sulfonamido)benzoate (JRW-1159)

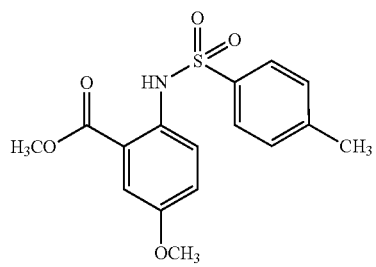 [SMILES: COC(=O)c1cc(OC)ccc1NS(=O)(=O)c1ccc(C)cc1]

Following general procedure A, methyl 2-amino-5-methoxybenzoate (5.0 g, 27.6 mmol) was reacted with 4-methylbenzenesulfonyl chloride (5.8 g, 30.3 mmol) to afford crude product as a purple solid. ESI MS m/z 336 [M+H]+.

Step 2. 5-methoxy-2-((4-methylphenyl)sulfonamido)benzoic acid (JRW-1161)

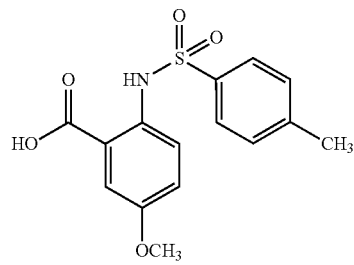 [SMILES: COc1ccc(NS(=O)(=O)c2ccc(C)cc2)c(C(=O)O)c1]

Following general procedure B, methyl 5-methoxy-2-((4-methylphenyl)sulfonamido)benzoate (27.6 mmol) was reacted with NaOH (27.6 mL, 2M, 55.2 mmol) to afford desired product (8.4 g, 94%) as a light purple solid. ESI MS m/z 322 [M+H]+.

Step 3. 5-methoxy-2-((4-methylphenyl)sulfonamido)-N-(p-tolyl)benzamide (JRW-1166)

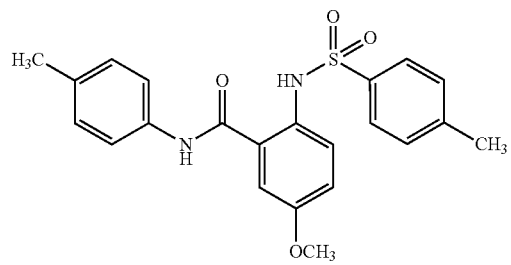

Following general procedure C2, 5-methoxy-2-((4-methylphenyl)sulfonamido)benzoic acid (500 mg, 1.6 mmol) was reacted with p-toluidine (200 mg, 1.9 mmol) to afford desired product (348 mg, 54%) as a white foam. ESI MS m/z 411 [M+H]+.

Example 62

N-(benzo[b]thiophen-2-yl)-5-methoxy-2-((4-methylphenyl)sulfonamido)benzamide (JRW-1167)

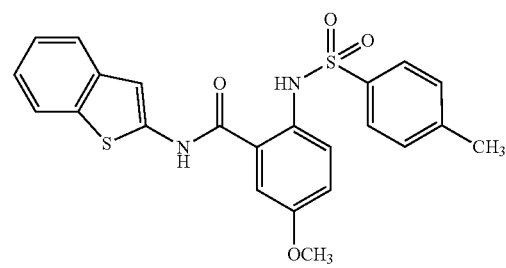

Following general procedure C2, 5-methoxy-2-((4-methylphenyl)sulfonamido)benzoic acid (100 mg, 0.31 mmol) was reacted with benzo[b]thiophen-2-amine (51 mg, 0.34 mmol) to afford desired product (34 mg, 24%) as a light brown solid. ESI MS m/z 453 [M+H]$^+$.

Example 63

4-methoxy-2-((4-methylphenyl)sulfonamido)-N-(p-tolyl)benzamide (JRW-1202)

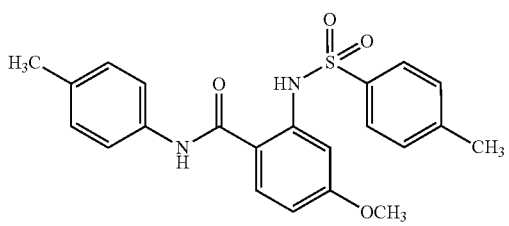

Step 1. Methyl 4-methoxy-2-((4-methylphenyl)sulfonamido)benzoate (JRW-1195)

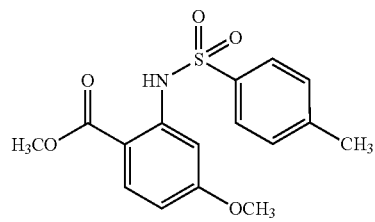 [SMILES: COC(=O)c1ccc(OC)cc1NS(=O)(=O)c1ccc(C)cc1]

Following general procedure A, methyl 2-amino-4-methoxybenzoate (1.0 g, 5.5 mmol) was reacted with 4-methylbenzenesulfonyl chloride (1.2 g, 6.1 mmol) to afford crude product (1.9 g) as a white foam. ESI MS m/z 336 [M+H]$^+$.

Step 2. 4-methoxy-2-((4-methylphenyl)sulfonamido)benzoic acid (JRW-1198)

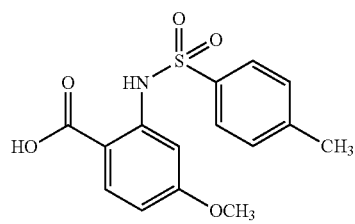 [SMILES: COc1ccc(C(=O)O)c(NS(=O)(=O)c2ccc(C)cc2)c1]

Following general procedure B, methyl 4-methoxy-2-((4-methylphenyl)sulfonamido)benzoate (5.5 mmol) was reacted with NaOH (5.6 mL, 2M, 11.3 mmol) to afford desired product (1.7 g, 94%) as a light yellow solid. ESI MS m/z 322 [M+H]$^+$.

Step 3. 4-methoxy-2-((4-methylphenyl)sulfonamido)-N-(p-tolyl)benzamide (JRW-1202)

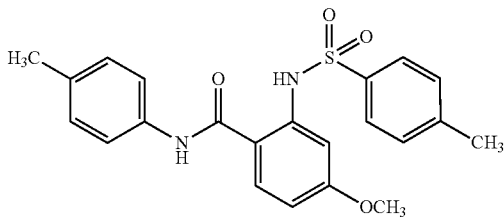

Following general procedure C2, 4-methoxy-2-((4-methylphenyl)sulfonamido)benzoic acid (510 mg, 1.6 mmol) was reacted with p-toluidine (200 mg, 1.9 mmol) to afford desired product (460 mg, 70%) as a white foam. ESI MS m/z 411 [M+H]$^+$.

Example 64

N-(benzo[b]thiophen-2-yl)-4-methoxy-2-((4-methylphenyl)sulfonamido)benzamide (JRW-1203)

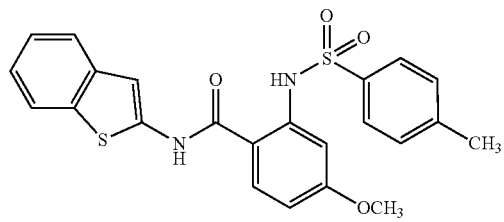 [SMILES: COc1ccc(C(=O)Nc2cc3ccccc3s2)c(NS(=O)(=O)c2ccc(C)cc2)c1]

Following general procedure C2, 4-methoxy-2-((4-methylphenyl)sulfonamido)benzoic acid (50 mg, 0.16 mmol) was reacted with benzo[b]thiophen-2-amine (27 mg, 1.8 mmol) to afford desired product (30 mg, 42%) as an orange solid. ESI MS m/z 453 [M+H]$^+$.

Example 65

2-((3-methoxyphenyl)sulfonamido)-N-(p-tolyl)benzamide (JRW-1205)

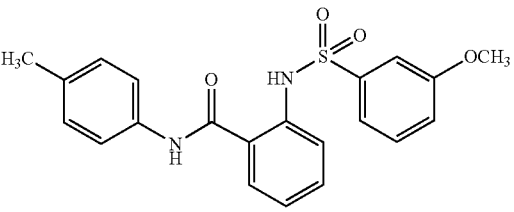 [SMILES: COc1cccc(S(=O)(=O)Nc2ccccc2C(=O)Nc2ccc(C)cc2)c1]

Step 1. Methyl 2-((3-methoxyphenyl)sulfonamido)benzoate (JRW-1196)

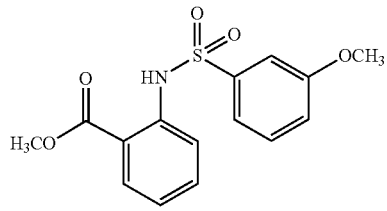 [SMILES: COC(=O)c1ccccc1NS(=O)(=O)c1cccc(OC)c1]

Following general procedure A, methyl 2-aminobenzoate (700 mg, 4.6 mmol) was reacted with 3-methoxybenzenesulfonyl chloride (1.05 g, 5.1 mmol) to afford desired product (1.3 g, 87%) as a white solid. ESI MS m/z 322 [M+H]$^+$.

Step 2. 2-((3-methoxyphenyl)sulfonamido)benzoic acid (JRW-1199)

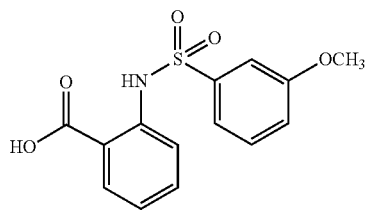 [SMILES: COc1cccc(S(=O)(=O)Nc2ccccc2C(=O)O)c1]

Following general procedure B, methyl 2-((3-methoxyphenyl)sulfonamido)benzoate (1.3 g, 4.1 mmol) was reacted with NaOH (4.0 mL, 2M, 8.0 mmol) to afford crude product (1.5 g) as a white solid. ESI MS m/z 308 [M+H]$^+$.

Step 3. 2-((3-methoxyphenyl)sulfonamido)-N-(p-tolyl)benzamide (JRW-1205)

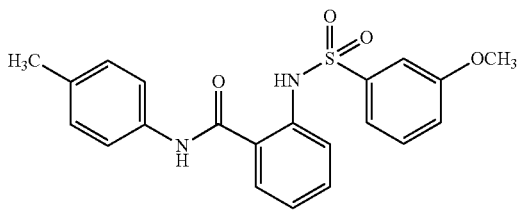 [SMILES: COc1cccc(S(=O)(=O)Nc2ccccc2C(=O)Nc2ccc(C)cc2)c1]

Following general procedure C2, 2-((3-methoxyphenyl)sulfonamido)benzoic acid (455 mg, 1.5 mmol) was reacted with p-toluidine (190 mg, 1.8 mmol) to afford desired product (335 mg, 57%) as a light brown solid. ESI MS m/z 397 [M+H]$^+$.

Example 66

N-(benzo[b]thiophen-2-yl)-2-((3-methoxyphenyl)sulfonamido)benzamide (JRW-1230)

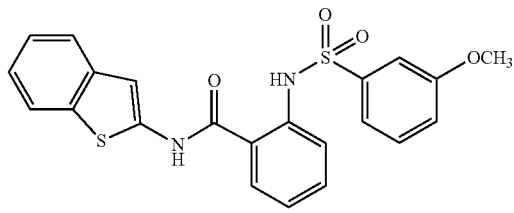 [SMILES: COc1cccc(S(=O)(=O)Nc2ccccc2C(=O)Nc2cc3ccccc3s2)c1]

Following general procedure C2, 2-((3-methoxyphenyl)sulfonamido)benzoic acid (60 mg, 0.19 mmol) was reacted with benzo[b]thiophen-2-amine (35 mg, 0.23 mmol) to afford desired product (30 mg, 35%) as a red brown solid. ESI MS m/z 439 [M+H]$^+$.

Example 67

5-hydroxy-2-((4-methylphenyl)sulfonamido)-N-(p-tolyl)benzamide (JRW-1232)

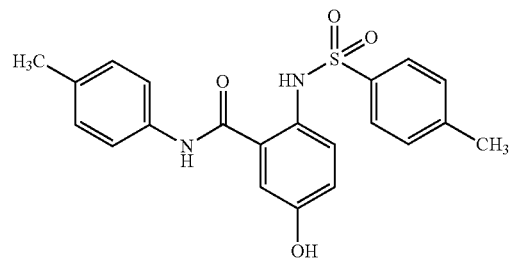

To a solution of 5-methoxy-2-((4-methylphenyl)sulfonamido)-N-(p-tolyl)benzamide (260 mg, 0.63 mmol) in DCM (10 mL) was added boron tribromide (1.6 mL, 1.0M, 1.6 mmol) at 0° C. The reaction warmed to rt, stirred for 18 h, and quenched with a saturated solution of NaHCO$_3$. The mixture was diluted with DCM and water, and the aqueous layer extracted with DCM. The organic layers were combined, dried with sodium sulfate, filtered, concentrated, and purified with silica gel chromatography to afford the desired product (29 mg, 11%) as a brown solid. ESI MS m/z 397 [M+H]$^+$.

Example 68

2-((3-hydroxyphenyl)sulfonamido)-N-(p-tolyl)benzamide (JRW-1236)

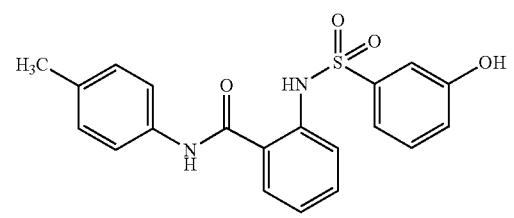 [SMILES: Cc1ccc(NC(=O)c2ccccc2NS(=O)(=O)c2cccc(O)c2)cc1]

To a solution of 2-((3-methoxyphenyl)sulfonamido)-N-(p-tolyl)benzamide (190 mg, 0.48 mmol) in DCM (10 mL) was added boron tribromide (0.96 mL, 1.0M, 0.96 mmol) at 0° C. The reaction warmed to rt, stirred for 18 h, and quenched with a saturated solution of NaHCO₃. The mixture was diluted with DCM and water, and the aqueous layer extracted with DCM. The organic layers were combined, dried with sodium sulfate, filtered, concentrated, and purified with silica gel chromatography to afford the desired product (140 mg, 76%) as a light brown solid. ESI MS m/z 383 [M+H]⁺.

Example 69

2-((3-butoxyphenyl)sulfonamido)-N-(p-tolyl)benzamide (JRW-1266)

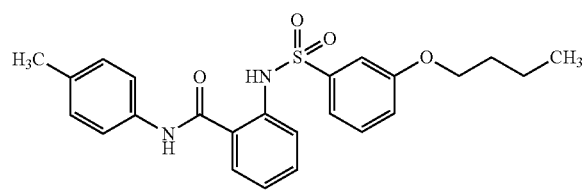 [SMILES: CCCCOc1cccc(S(=O)(=O)Nc2ccccc2C(=O)Nc2ccc(C)cc2)c1]

To a solution of 2-((3-hydroxyphenyl)sulfonamido)-N-(p-tolyl)benzamide (40 mg, 0.10 mmol) in THF (3 mL) was added n-butanol (15 mg, 0.20 mmol), triphenylphosphine (30 mg, 0.12 mmol) and DIAD (46 mg, 0.23 mmol). The mixture stirred at rt for 18 h. The mixture was diluted with ethyl acetate and water, and the aqueous layer extracted with ethyl acetate. The organic layers were combined, dried with sodium sulfate, filtered, concentrated, and purified with silica gel chromatography to afford the desired product (30 mg, 65%) as a white solid. ESI MS m/z 439 [M+H]⁺.

Example 70

N-(2-bromophenyl)-2-((4-methylphenyl)sulfonamido)benzamide (JRW-1282)

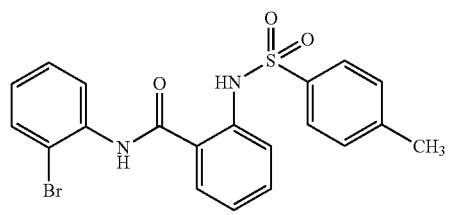 [SMILES: Cc1ccc(S(=O)(=O)Nc2ccccc2C(=O)Nc2ccccc2Br)cc1]

Following general procedure C2, 2-((4-methylphenyl)sulfonamido)benzoic acid (200 mg, 0.68 mmol) was reacted with 2-bromoaniline (141 mg, 0.82 mmol) to afford desired product (48 mg, 15%) as a white solid. ESI MS m/z 446 [M+H]⁺.

Example 71

N-(3-bromophenyl)-2-((4-methylphenyl)sulfonamido)benzamide (JRW-1283)

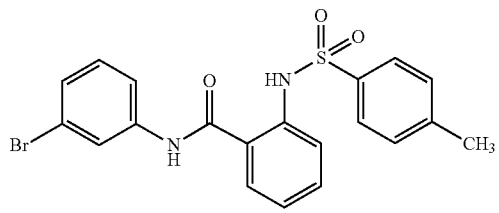 [SMILES: Cc1ccc(S(=O)(=O)Nc2ccccc2C(=O)Nc2cccc(Br)c2)cc1]

Following general procedure C2, 2-((4-methylphenyl)sulfonamido)benzoic acid (200 mg, 0.68 mmol) was reacted with 3-bromoaniline (141 mg, 0.82 mmol) to afford desired product (122 mg, 40%) as a white solid. ESI MS m/z 446 [M+H]⁺.

Example 72

N-([1,1'-biphenyl]-4-yl)-2-((4-methylphenyl)sulfonamido)benzamide (JRW-1288)

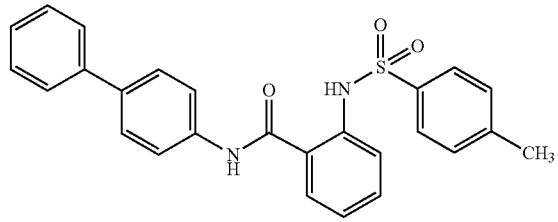 [SMILES: Cc1ccc(S(=O)(=O)Nc2ccccc2C(=O)Nc2ccc(-c3ccccc3)cc2)cc1]

Following general procedure C2, 2-((4-methylphenyl)sulfonamido)benzoic acid (50 mg, 0.17 mmol) was reacted with [1,1'-biphenyl]-4-amine (34 mg, 0.20 mmol) to afford desired product (42 mg, 55%) as a white solid. ESI MS m/z 443 [M+H]⁺.

Example 73

N-(2-methoxyphenyl)-2-((4-methylphenyl)sulfonamido)benzamide (JRW-1292)

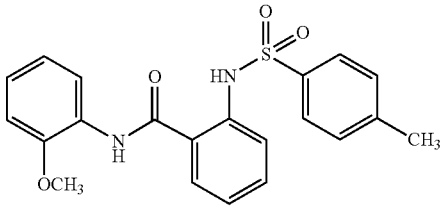 [SMILES: COc1ccccc1NC(=O)c1ccccc1NS(=O)(=O)c1ccc(C)cc1]

Following general procedure C2, 2-((4-methylphenyl)sulfonamido)benzoic acid (190 mg, 0.65 mmol) was reacted with 2-methoxyaniline (96 mg, 0.78 mmol) to afford desired product (155 mg, 60%) as a light brown solid. ESI MS m/z 397 [M+H]⁺.

Example 74

N-([1,1'-biphenyl]-3-yl)-2-((4-methylphenyl)sulfonamido)benzamide (JRW-1297)

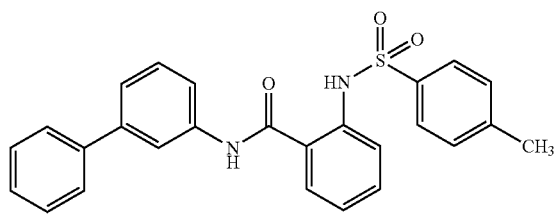 [SMILES: Cc1ccc(S(=O)(=O)Nc2ccccc2C(=O)Nc2cccc(-c3ccccc3)c2)cc1]

To a solution of N-(3-bromophenyl)-2-((4-methylphenyl)sulfonamido)benzamide (110 mg, 0.24 mmol) in dioxane (5 mL) was added phenylboronic acid (36 mg, 0.29 mmol) and Pd(dppf)Cl$_2$ (20 mg, 0.024 mmol). The mixture was purged with nitrogen after which aqueous Cs$_2$CO$_3$ (0.74 mL, 1 M) was added. The reaction was heated to 80° C. for 2 h. The mixture was diluted with ethyl acetate and washed with water and brine. The organic layers were combined, dried with sodium sulfate, filtered, concentrated, and purified with silica gel chromatography to afford the desired product (105 mg, 96%) as a white solid. ESI MS m/z 443 [M+H]$^+$.

Example 75

N-(3-methoxyphenyl)-2-((4-methylphenyl)sulfonamido)benzamide (JRW-1299)

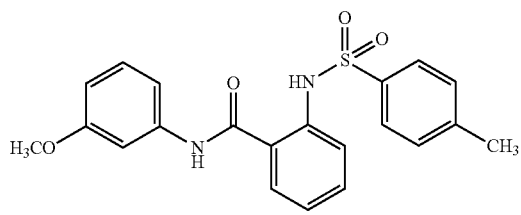 [SMILES: COc1cccc(NC(=O)c2ccccc2NS(=O)(=O)c2ccc(C)cc2)c1]

Following general procedure C2, 2-((4-methylphenyl)sulfonamido)benzoic acid (190 mg, 0.65 mmol) was reacted with 3-methoxyaniline (96 mg, 0.78 mmol) to afford desired product (165 mg, 64%) as a white solid. ESI MS m/z 397 [M+H]$^+$.

Example 76

N-(4-methoxyphenyl)-2-((4-methylphenyl)sulfonamido)benzamide (JRW-1300)

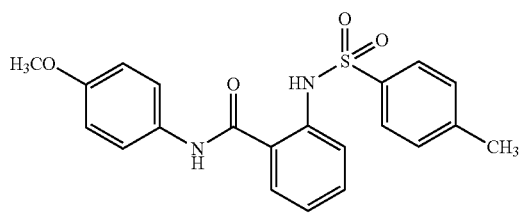 [SMILES: COc1ccc(NC(=O)c2ccccc2NS(=O)(=O)c2ccc(C)cc2)cc1]

Following general procedure C2, 2-((4-methylphenyl)sulfonamido)benzoic acid (190 mg, 0.65 mmol) was reacted with 4-methoxyaniline (96 mg, 0.78 mmol) to afford desired product (156 mg, 60%) as a light brown solid. ESI MS m/z 397 [M+H]$^+$.

Example 77

2-((N-ethyl-4-methylphenyl)sulfonamido)-N-(4-methoxyphenyl)benzamide (JRW-1325)

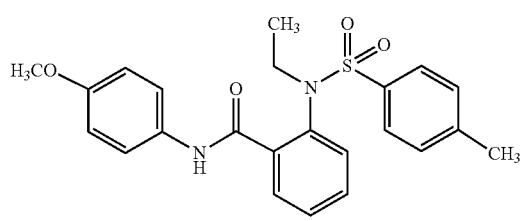 [SMILES: CCN(c1ccccc1C(=O)Nc1ccc(OC)cc1)S(=O)(=O)c1ccc(C)cc1]

To a solution of N-(4-methoxyphenyl)-2-((4-methylphenyl)sulfonamido)benzamide (50 mg, 0.12 mmol) in DMF (3 mL) was added diisopropylethylamine (49 mg, 0.38 mmol) and ethyl iodide (0.5 mL). The solution stirred for 18 h at 60° C. The mixture was diluted with ethyl acetate and washed with water and brine. The organic layers were combined, dried with sodium sulfate, filtered, concentrated, and purified with silica gel chromatography to afford the desired product (50 mg, 94%) as a light yellow foam. ESI MS m/z 425 [M+H]$^+$.

Example 78

N-(benzo[b]thiophen-2-yl)-4-fluoro-2-((4-methylphenyl)sulfonamido)benzamide (JRW-1346)

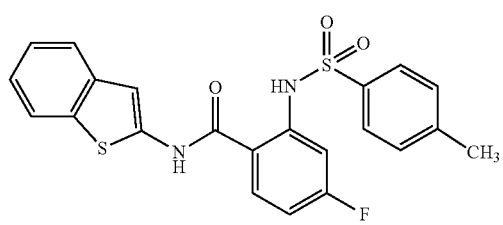 [SMILES: Cc1ccc(S(=O)(=O)Nc2cc(F)ccc2C(=O)Nc2cc3ccccc3s2)cc1]

Step 1. Methyl 4-fluoro-2-((4-methylphenyl)sulfonamido)benzoate (JRW-1342)

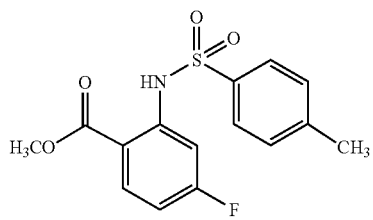 [SMILES: COC(=O)c1ccc(F)cc1NS(=O)(=O)c1ccc(C)cc1]

Following general procedure A, methyl 2-amino-4-fluorobenzoate (1.0 g, 5.9 mmol) was reacted with 4-methylbenzenesulfonyl chloride (1.2 g, 6.5 mmol) to afford the desired product (1.52 g, 79%) as a light yellow solid. ESI MS m/z 324 [M+H]+.

Step 2. 4-fluoro-2-((4-methylphenyl)sulfonamido) benzoic acid (JRW-1344)

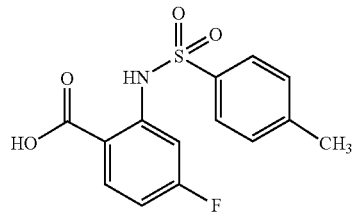 [SMILES: Cc1ccc(S(=O)(=O)Nc2cc(F)ccc2C(=O)O)cc1]

Following general procedure B, methyl 4-fluoro-2-((4-methylphenyl)sulfonamido)benzoate (1.5 g, 4.6 mmol) was reacted with NaOH (7 mL, 2 M, 14 mmol) to afford crude product (1.6 g) as a light yellow solid. ESI MS m/z 310 [M+H]+.

Step 3. N-(benzo[b]thiophen-2-yl)-4-fluoro-2-((4-methylphenyl)sulfonamido)benzamide (JRW-1346)

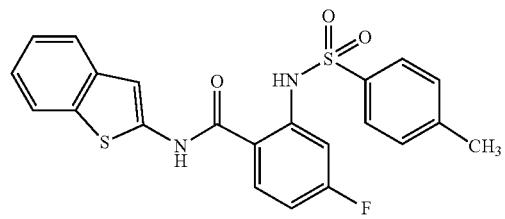 [SMILES: Cc1ccc(S(=O)(=O)Nc2cc(F)ccc2C(=O)Nc2cc3ccccc3s2)cc1]

Following general procedure C2, 4-fluoro-2-((4-methylphenyl)sulfonamido)benzoic acid (100 mg, 0.32 mmol) was reacted with benzo[b]thiophen-2-amine (58 mg, 0.39 mmol) to afford desired product (93 mg, 65%) as a light pink solid. ESI MS m/z 441 [M+H]+.

Example 79

N-(benzo[b]thiophen-2-yl)-5-fluoro-2-((4-methylphenyl)sulfonamido)benzamide (JRW-1347)

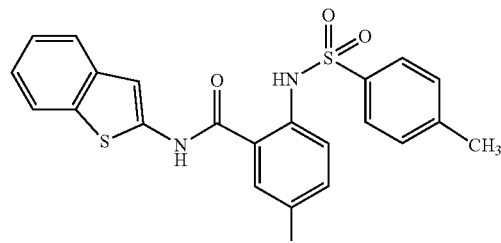

Step 1. Methyl 5-fluoro-2-((4-methylphenyl)sulfonamido)benzoate (JRW-1343)

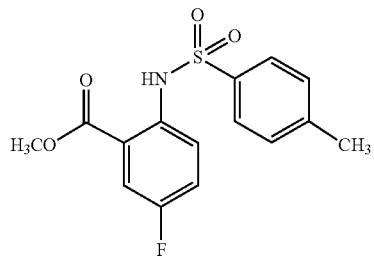 [SMILES: COC(=O)c1cc(F)ccc1NS(=O)(=O)c1ccc(C)cc1]

Following general procedure A, methyl 2-amino-5-fluorobenzoate (1.0 g, 5.9 mmol) was reacted with 4-methylbenzenesulfonyl chloride (1.2 g, 6.5 mmol) to afford the desired product (1.9 g, 99%) as a white solid. ESI MS m/z 324 [M+H]+.

Step 2. 5-fluoro-2-((4-methylphenyl)sulfonamido) benzoic acid (JRW-1345)

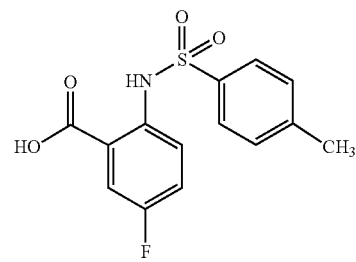 [SMILES: Cc1ccc(S(=O)(=O)Nc2ccc(F)cc2C(=O)O)cc1]

Following general procedure B, methyl 5-fluoro-2-((4-methylphenyl)sulfonamido)benzoate (1.9 g, 5.9 mmol) was reacted with NaOH (9 mL, 2 M, 18 mmol) to afford crude product (1.8 g) as a white solid. ESI MS m/z 310 [M+H]+.

Step 3. N-(benzo[b]thiophen-2-yl)-5-fluoro-2-((4-methylphenyl)sulfonamido)benzamide (JRW-1347)

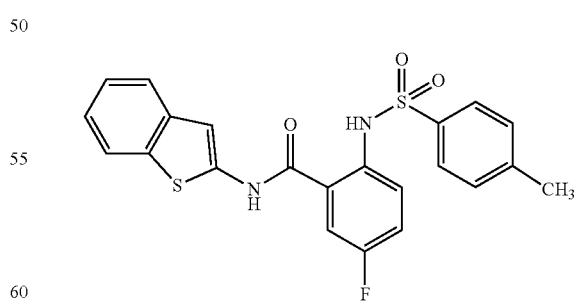

Following general procedure C2, 5-fluoro-2-((4-methylphenyl)sulfonamido)benzoic acid (100 mg, 0.32 mmol) was reacted with benzo[b]thiophen-2-amine (58 mg, 0.39 mmol) to afford desired product (38 mg, 26%) as a light brown solid. ESI MS m/z 441 [M+H]+.

Example 80

N-benzyl-2-((4-methylphenyl)sulfonamido)benzamide (JRW-1383)

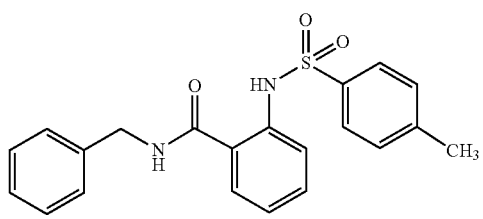 [SMILES: Cc1ccc(S(=O)(=O)Nc2ccccc2C(=O)NCc2ccccc2)cc1]

Following general procedure C2, 2-((4-methylphenyl)sulfonamido)benzoic acid (50 mg, 0.17 mmol) was reacted with benzylamine (31 mg, 0.21 mmol) to afford desired product (6 mg, 9%) as a light brown solid. ESI MS m/z 381 [M+H]$^+$.

Example 81

N-(4-methoxybenzyl)-2-((4-methylphenyl)sulfonamido)benzamide (JRW-1384)

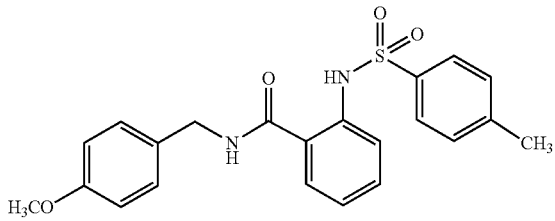 [SMILES: COc1ccc(CNC(=O)c2ccccc2NS(=O)(=O)c2ccc(C)cc2)cc1]

Following general procedure C2, 2-((4-methylphenyl)sulfonamido)benzoic acid (50 mg, 0.17 mmol) was reacted with 4-methoxy-benzylamine (31 mg, 0.21 mmol) to afford desired product (25 mg, 35%) as a light brown solid. ESI MS m/z 411 [M+H]$^+$.

Example 82

N-(benzo[b]thiophen-2-yl)-2-((4-methylphenyl)sulfonamido)-5-(trifluoromethyl)benzamide (JRW-1388)

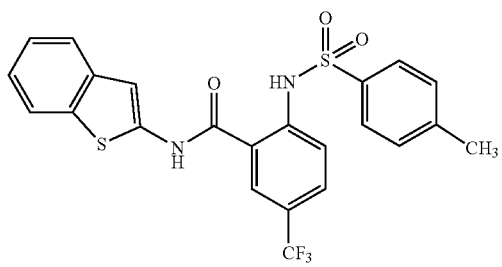 [SMILES: Cc1ccc(S(=O)(=O)Nc2ccc(C(F)(F)F)cc2C(=O)Nc2cc3ccccc3s2)cc1]

Step 1. Methyl 2-((4-methylphenyl)sulfonamido)-5-(trifluoromethyl)benzoate (JRW-1382)

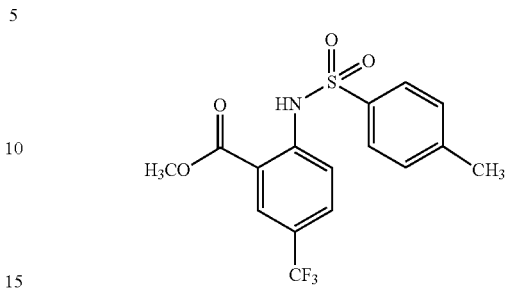

Following general procedure A, methyl 2-amino-5-(trifluoromethyl)benzoate (1.0 g, 4.6 mmol) was reacted with 4-methylbenzenesulfonyl chloride (0.96 g, 5.0 mmol) to afford the desired product (1.4 g, 81%) as a white solid. ESI MS m/z 374 [M+H]$^+$.

Step 2. 2-((4-methylphenyl)sulfonamido)-5-(trifluoromethyl)benzoic acid (JRW-1386)

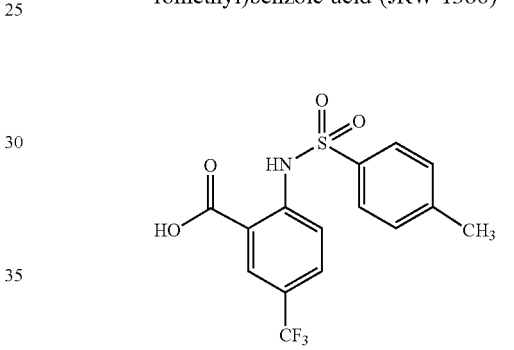

Following general procedure B, methyl 2-((4-methylphenyl)sulfonamido)-5-(trifluoromethyl)benzoate (1.4 g, 3.7 mmol) was reacted with NaOH (3.7 mL, 2 M, 7.4 mmol) to afford crude product (1.3 g) as a white solid. ESI MS m/z 360 [M+H]$^+$.

Step 3. N-(benzo[b]thiophen-2-yl)-2-((4-methylphenyl)sulfonamido)-5-(trifluoromethyl)benzamide (JRW-1388)

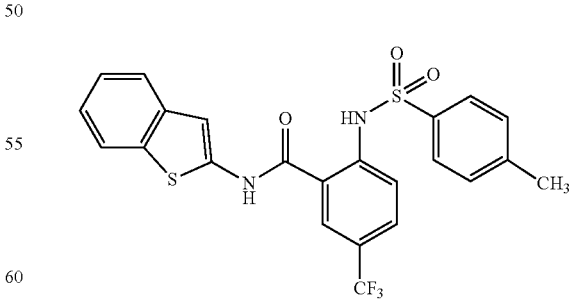

Following general procedure C2, 2-((4-methylphenyl)sulfonamido)-5-(trifluoromethyl)benzoic acid (110 mg, 0.31 mmol) was reacted with benzo[b]thiophen-2-amine (55 mg, 0.37 mmol) to afford desired product (140 mg, 93%) as a light brown solid. ESI MS m/z 491 [M+H]$^+$.

Example 83

Selective Inhibition of Bioluminescent Complexes

Figure 1B:
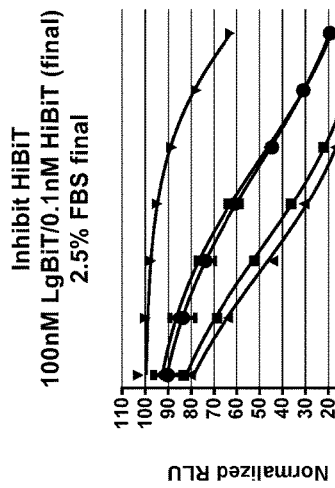
Figure 1C:
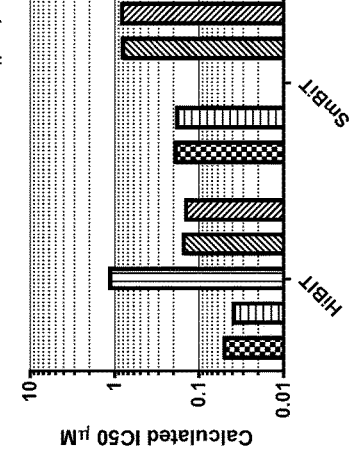

The following example provides a use for the disclosed inhibitor to selectively inhibit various bioluminescent complexes, e.g., *Oplophorus* luciferase-derived bioluminescent complex, without inhibiting NanoLuc® luciferase. FIG. 1A shows inhibition of the NanoBiT® HiBiT/LgBiT bioluminescent complex by exemplary compounds. NanoBiT® HiBiT non-luminescent peptide and NanoBiT® LgBiT non-luminescent polypeptide were diluted in PBS+0.01% BSA, respectively (final concentration of 0.1 nM and 100 nM, respectively), and incubated with the serially diluted concentrations of the indicated compounds for 2 hours at room temperature in the presence of RPMI media. (2.5% FBS final) Samples were analyzed after addition of furimazine (10 μM final concentration) using a GloMax®-Multi+ Plate Reader. Each sample was normalized to a "no inhibitor" control. The $IC_{50}$ values were then determined using GraphPad Prism (log[inhibitor] vs. normalized response). FIG. 1B shows the inhibition of the NanoBiT® SmBiT/LgBiT bioluminescent complex by exemplary compounds of the present invention. The NanoBiT® SmBiT-annexin fusion and NanoBiT® LgBiT-annexin fusion were diluted to a final concentration of 60 nM and 30 nM, respectively, in PBS/ 0.01% BSA and incubated with serially diluted concentrations of the indicated compounds for 2 hours at room temperature in the presence of K562 cell lysate diluted into RPMI media (2.5% FBS final). Samples were analyzed after addition of furimazine (10 μM final concentration) using a GloMax®-Multi+ Plate Reader. Each sample was normalized to a "no inhibitor" control. The $IC_{50}$ values were then determined using GraphPad Prism (log[inhibitor] vs. normalized response). FIG. 1C is a bar graph comparing the calculated $IC_{50}$ values between the NanoBiT® HiBiT/ LgBiT and SmBiT/LgBiT complexes of the exemplary compounds shown in FIGS. 1A and 1B.

Figure 2:
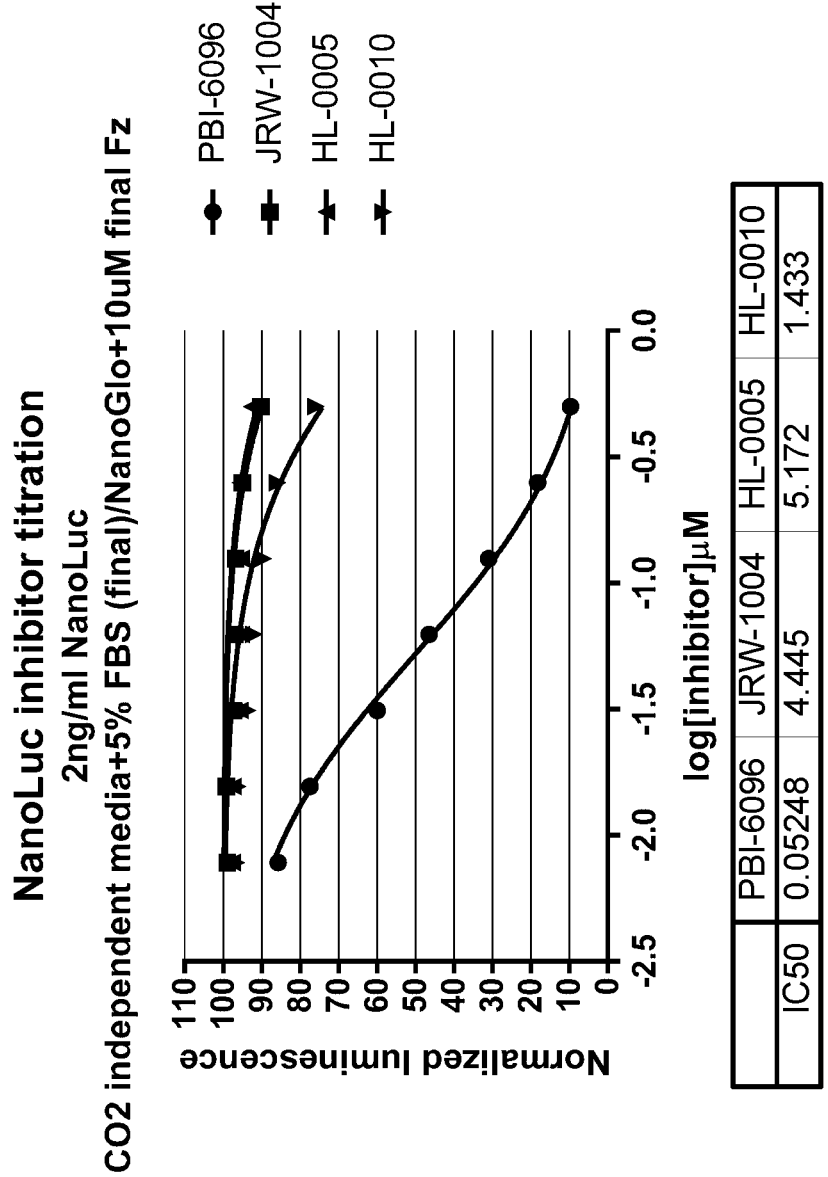
FIG. 2 compares the NANOLUC® (Nluc) inhibitory activity of exemplary compounds of the present invention to PBI-6096, a known Nluc inhibitor. JRW-1004, HL-0005, and HL-0010 do not show any appreciable inhibition against NanoLuc indicating selective inhibition for *Oplophorus* luciferase-derived bioluminescent complexes.

FIG. 2 compares the NANOLUC® (Nluc) inhibitory activity of exemplary compounds of the present invention to PBI-6096, a known Nluc inhibitor. Inhibitors were diluted into $CO_2$-independent media with 10% FBS. Nluc was diluted to 2 ng/ml into NanoGlo® buffer with 100 μM furimazine. Serial dilutions of the inhibitors were added to the NanoLuc/furimazine/NanoGlo® solution, and samples were immediately analyzed using a GloMax®-Multi+ Plate Reader. As shown in FIG. 2, JRW-1004, HL-0005, and HL-0010 do not show any appreciable inhibition against NanoLuc demonstrating the selectivity of the compounds for *Oplophorus* luciferase-derived bioluminescent complexes.

Example 84

Inhibition of Bioluminescent Complexes in Cells

Figures 3A, 3B:
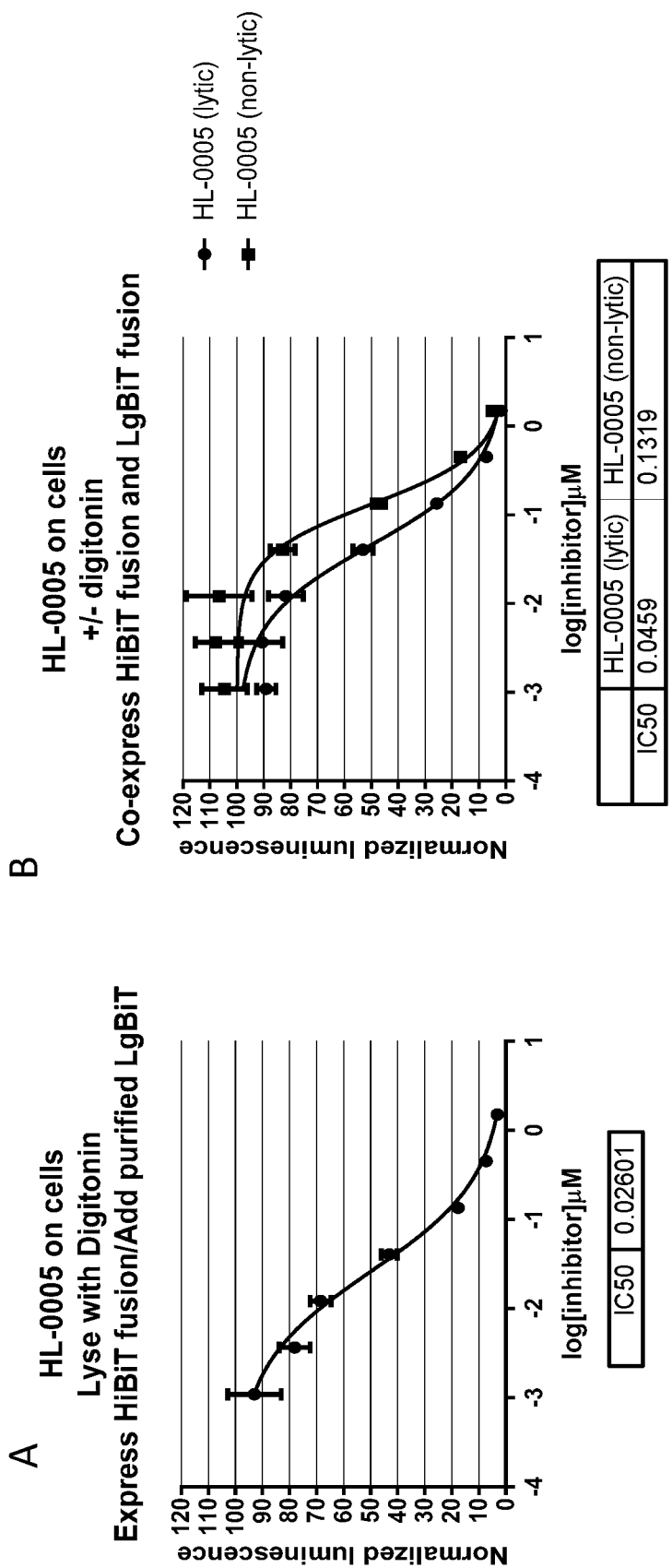
FIGS. 3A-3B show the inhibition of bioluminescent complexes in cells by exemplary compounds of the present invention.

FIGS. 3A-3B show the inhibition of bioluminescent complexes in cells. In FIG. 3A, HEK293 cells were transfected with DNA encoding an intracellular NanoBiT® HiBiT fusion protein, plated at 20,000 cells/100 μL growth medium, and incubated for 24 hours. Following 24 hours of expression, cells were lysed with 50 ug/mL (final) of digitonin in OptiMEM and treated with purified NanoBiT® LgBiT non-luminescent polypeptide and serial dilutions of HL-0005. After 2 hours of incubation at room temperature, furimazine was added (10 μM final concentration), and luminescence was measured on a GloMax®-Multi+ Plate Reader.

In FIG. 3B, HEK293 cells were transfected with DNA encoding an intracellular NanoBiT® HiBiT fusion protein and DNA encoding an intracellular NanoBiT® LgBiT fusion protein such that the fusion proteins were co-expressed within the cell. Transfected cells were plated at 20,000 cells/100 μL growth medium and incubated for 24 hours. Following 24 hours of expression, cells were optionally lysed with 50 ug/mL of digitonin in OptiMEM and treated with serial dilutions of HL-0005. After 2 hours of incubation at room temperature, furimazine was added (10 μM final concentration), and luminescence was measured on a GloMax® Multi+ Plate Reader. FIG. 3A shows inhibition of the NanoBiT® HiBit/LgBit bioluminescent complex with HL-0005 in a cellular context. FIG. 3B compares $IC_{50}$ values in lytic and non-lytic conditions indicating HL-0005 is mostly cell permeable.

Example 85

Inhibitor $IC_{50}$ Determination

The following example provides the $IC_{50}$ values for the compounds disclosed herein. The results are shown in Table 1. NanoBiT® HiBiT non-luminescent peptide and LgBiT non-luminescent non-polypeptide were diluted to 0.1 nM and 1 nM, respectively, in TBS buffer with 0.01% BSA to make the detection reagent. A 3× dilution series of each inhibitor was then made in the detection reagent. A "no inhibitor" control was also made for each sample. 50 ul of each inhibitor dilution was mixed 6 μM (final) furimazine, and luminescence was measured. Each sample was normalized to the "no inhibitor" control. The $IC_{50}$ values were then determined using GraphPad Prism (log[inhibitor] vs. normalized response)

TABLE 1

| Identifier | IC50 (uM) |
|---|---|
| JRW-0998 | 0.043 |
| JRW-1004 | 0.03 |
| JRW-1006 | 1.0 |
| JRW-1008 | 0.24 |
| JRW-1011 | 0.094 |
| HL-0005 | 0.0039 |
| HL-0006 | 0.21 |
| HL-0007 | 0.014 |
| HL-0008 | 0.024 |
| HL-0009 | 16 |
| HL-0010 | 0.022 |
| HL-0012 | 0.49 |
| HL-0017 | NA |
| HL-0019 | 0.029 |
| HL-0023 | 0.58 |
| HL-0025 | 0.085 |
| HL-0026 | 0.24 |
| HL-0030 | NA |
| HL-0031 | NA |
| HL-0035 | NA |
| HL-0038 | 0.044 |
| HL-0040 | 0.43 |
| HL-0041 | 0.013 |
| HL-0044 | 0.088 |
| HL-0057 | 0.055 |
| HL-0059 | 0.19 |
| HL-0061 | 0.029 |
| HL-0062 | 1.2 |
| JRW-1076 | 0.026 |
| JRW-1077 | 0.089 |
| HL-0070 | 0.13 |
| HL-0071 | 0.043 |
| JRW-1090 | 1.1 |
| JRW-1091 | NA |

TABLE 1-continued

| Identifier | IC50 (uM) |
|---|---|
| JRW-1107 | NA |
| JRW-1110 | NA |
| JRW-1114 | 0.17 |
| JRW-1120 | NA |
| JRW-1121 | NA |
| JRW-1146 | 0.63 |
| JRW-1150 | 19 |
| JRW-1152 | 0.12 |
| JRW-1154 | NA |
| JRW-1164 | 6.5 |
| JRW-1166 | 0.13 |
| JRW-1167 | 0.02 |
| JRW-1202 | 0.18 |
| JRW-1203 | 0.1 |
| JRW-1205 | 0.029 |
| JRW-1230 | 0.0078 |
| JRW-1232 | 1.0 |
| JRW-1236 | 0.033 |
| JRW-1248 | 0.28 |
| JRW-1250 | 0.54 |
| JRW-1251 | NA |
| JRW-1253 | 2.3 |
| JRW-1255 | 0.060 |
| JRW-1261 | 0.17 |
| JRW-1263 | NA |
| JRW-1266 | 1.5 |
| JRW-1267 | 0.036 |
| JRW-1269 | 1.1 |
| JRW-1268 | NA |
| JRW-1270 | 1.2 |
| JRW-1271 | NA |
| JRW-1272 | 0.70 |
| JRW-1273 | NA |
| JRW-1275 | 0.34 |
| JRW-1282 | 0.20 |
| JRW-1283 | 0.046 |
| JRW-1284 | 0.71 |
| JRW-1285 | 0.36 |
| JRW-1287 | 0.15 |
| JRW-1288 | 0.11 |
| JRW-1293 | NA |
| JRW-1292 | 0.59 |
| JRW-1297 | 0.10 |
| JRW-1299 | 0.090 |
| JRW-1300 | 0.043 |
| JRW-1325 | 1.3 |
| JRW-1327 | 0.36 |
| JRW-1328 | 1.1 |
| JRW-1346 | 0.014 |
| JRW-1347 | 0.0008 |
| JRW-1383 | NA |
| JRW-1384 | NA |
| JRW-1388 | 0.00058 |

NA—no activity
NT—not tested

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

APPENDIX

SEQ ID NO: 1
Native Mature Oplophorus luciferase amino acid sequence
FTLADFVGDWQQTAGYNQDQVLEQGGLSSLFQALGVSVTPIQKVVLSGEN

GLKADIHVIIPYEGLSGFQMGLIEMIFKVVYPVDDHHFKIILHYGTLVID

GVTPNMIDYFGRPYPGIAVFDGKQITVTGTLWNGNKIYDERLINPDGSLL

FRVTINGVTGWRLCENILA

SEQ ID NO: 2
Wild-Type NLpep
MGVTGWRLCERILA

SEQ ID NO: 3
Wild-Type NLpoly
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTINV

SEQ ID NO: 4
amino acid sequence for HiBiT
VSGWRLFKKIS

SEQ ID NO: 5
amino acid sequence for LgBiT
MVFTLEDFVGDWEQTAAYNLDQVLEQGGVSSLLQNLAVSVTPIQRIVRSG

ENALKIDIHVIIPYEGLSADQMAQIEEVFKVVYPVDDHHFKVILPYGTLV

IDGVTPNMLNYFGRPYEGIAVFDGKKITVTGTLWNGNKIIDERLITPDGS

MLFRVTINS

SEQ ID NO: 6
amino acid sequence for SmBiT
VTGYRLFEEIL

SEQ ID NO: 7
NanoLuc
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTINGVTGWRLCERILA

The invention claimed is:

1. A compound selected from the group consisting of:
N-(3-cyano-4,5,6,7-tetrahydrobenzo[b]thiophen-2-yl)-2-((4-methylphenyl)sulfonamido)benzamide;
N-(3-cyanothiophen-2-yl)-2-((4-methylphenyl)sulfonamido)benzamide;
N-(2-cyanophenyl)-2-((4-methylphenyl)sulfonamido)benzamide;
N-(3-cyano-5,6-dihydro-4H-cyclopenta[b]thiophen-2-yl)-2-(phenylsulfonamido)benzamide;
2-([1,1'-biphenyl]-3-sulfonamido)-N-(p-tolyl)benzamide;
methyl 3-(N-(2-(p-tolylcarbamoyl)phenyl)sulfamoyl)benzoate;
3-(N-(2-(p-tolylcarbamoyl)phenyl)sulfamoyl)benzoic acid;
2-((3-acetamidophenyl)sulfonamido)-N-(p-tolyl)benzamide;
2-((3-aminophenyl)sulfonamido)-N-(p-tolyl)benzamide;
2-((3-(hydroxymethyl)phenyl)sulfonamido)-N-(p-tolyl)benzamide;
2-((3-(butylcarbamoyl)phenyl)sulfonamido)-N-(p-tolyl)benzamide;
2-((3-bromophenyl)sulfonamido)-N-(p-tolyl)benzamide;
2-((3-(butylamino)phenyl)sulfonamido)-N-(p-tolyl)benzamide;
2-((3-(hex-1-yn-1-yl)phenyl)sulfonamido)-N-(p-tolyl)benzamide;
2-((3-hexylphenyl)sulfonamido)-N-(p-tolyl)benzamide;
2-((3-(3-hydroxyprop-1-yn-1-yl)phenyl)sulfonamido)-N-(p-tolyl)benzamide;
2-((3-(3-hydroxypropyl)phenyl)sulfonamido)-N-(p-tolyl)benzamide;
N-(p-tolyl)-2-((4-(trifluoromethyl)phenyl)sulfonamido)benzamide;
2-((4-methoxyphenyl)sulfonamido)-N-(p-tolyl)benzamide;
2-((4-bromophenyl)sulfonamido)-N-(p-tolyl)benzamide;
2-([1,1'-biphenyl]-4-sulfonamido)-N-(p-tolyl)benzamide;
N-(p-tolyl)-2-((3-(trifluoromethyl)phenyl)sulfonamido)benzamide;
N-(p-tolyl)-2-((3-(trifluoromethoxy)phenyl)sulfonamido)benzamide;
2-((4-methylphenyl)sulfonamido)-N-(naphthalen-2-yl)benzamide;
2-((4-methylphenyl)sulfonamido)-N-(5,6,7,8-tetrahydronaphthalen-2-yl)benzamide;
methyl trans-4-(2-((4-methylphenyl)sulfonamido)benzamido)cyclohexane-1-carboxylate;
trans-4-(2-((4-methylphenyl)sulfonamido)benzamido)cyclohexane-1-carboxylic acid;
2-((4-methylphenyl)sulfonamido)-N-(p-tolyl)benzamide;
ethyl 2-(4-(2-((4-methylphenyl)sulfonamido)benzamido)phenyl)acetate;
N-(3-isopropylphenyl)-2-((4-methylphenyl)sulfonamido)benzamide;
ethyl 3-(2-((4-methylphenyl)sulfonamido)benzamido)benzoate;
2-(4-(2-((4-methylphenyl)sulfonamido)benzamido)phenyl)acetic acid;
3-(2-((4-methylphenyl)sulfonamido)benzamido)benzoic acid;
2-((4-methylphenyl)sulfonamido)-N-(m-tolyl)benzamide;
2-((4-methylphenyl)sulfonamido)-N-(2-propylphenyl)benzamide;
N-(3-butylphenyl)-2-((4-methylphenyl)sulfonamido)benzamide;

N-(4-butylphenyl)-2-((4-methylphenyl)sulfonamido)benzamide;
N-(4-hexylphenyl)-2-((4-methylphenyl)sulfonamido)benzamide;
2-((4-methylphenyl)sulfonamido)-N-(4-octylphenyl)benzamide;
methyl 6-(4-(2-((4-methylphenyl)sulfonamido)benzamido)phenyl)hexanoate;
6-(4-(2-((4-methylphenyl)sulfonamido)benzamido)phenyl)hexanoic acid;
N-(4-(6-hydroxyhexyl)phenyl)-2-((4-methylphenyl)sulfonamido)benzamide;
N-(4-(4-hydroxybutyl)phenyl)-2-((4-methylphenyl)sulfonamido)benzamide;
N-(4-(4-bromobutyl)phenyl)-2-((4-methylphenyl)sulfonamido)benzamide;
5-methoxy-2-((4-methylphenyl)sulfonamido)-N-(p-tolyl)benzamide;
4-methoxy-2-((4-methylphenyl)sulfonamido)-N-(p-tolyl)benzamide;
2-((3-methoxyphenyl)sulfonamido)-N-(p-tolyl)benzamide;
5-hydroxy-2-((4-methylphenyl)sulfonamido)-N-(p-tolyl)benzamide;
2-((3-hydroxyphenyl)sulfonamido)-N-(p-tolyl)benzamide;
2-((3-butoxyphenyl)sulfonamido)-N-(p-tolyl)benzamide;
N-(2-bromophenyl)-2-((4-methylphenyl)sulfonamido)benzamide;
N-(3-bromophenyl)-2-((4-methylphenyl)sulfonamido)benzamide;
N-([1,1'-biphenyl]-4-yl)-2-((4-methylphenyl)sulfonamido)benzamide;
N-(2-methoxyphenyl)-2-((4-methylphenyl)sulfonamido)benzamide;
N-([1,1'-biphenyl]-3-yl)-2-((4-methylphenyl)sulfonamido)benzamide;
N-(3-methoxyphenyl)-2-((4-methylphenyl)sulfonamido)benzamide;
N-(4-methoxyphenyl)-2-((4-methylphenyl)sulfonamido)benzamide;
2-((N-ethyl-4-methylphenyl)sulfonamido)-N-(4-methoxyphenyl)benzamide;
N-(4-methoxybenzyl)-2-((4-methylphenyl)sulfonamido)benzamide;
or a salt thereof.

2. A method of inhibiting luciferase activity of an *Oplophorus* luciferase-derived bioluminescent complex, the method comprising contacting the bioluminescent complex with the compound of claim 1.

3. The method of claim 2, wherein the bioluminescent complex comprises two or more substantially non-luminescent peptide and/or polypeptide units, and wherein association of the two or more non-luminescent peptide and/or polypeptide units produces a detectable bioluminescent signal in the presence of a coelenterazine substrate.

4. The method of claim 3, wherein association of the two or more substantially non-luminescent peptide and/or polypeptide units generates a bioluminescent complex capable of binding the coelenterazine substrate.

5. The method of claim 2, wherein the bioluminescent complex comprises:
a) a peptide comprising an amino acid sequence having less than 100% and greater than 40% identity to SEQ ID NO: 2; and
b) a polypeptide comprising an amino acid sequence having less than 100% and greater than 40% identity with SEQ ID NO: 3,
wherein the bioluminescent complex exhibits detectable luminescence in the presence of a coelenterazine substrate.

6. The method of claim 5, wherein the bioluminescent complex comprises a polypeptide having an amino acid sequence of SEQ ID NO: 5 and a peptide having an amino acid sequence of SEQ ID NO: 4 or SEQ ID NO: 6.

7. A method for modulating luminescence of an *Oplophorus* luciferase-derived bioluminescent complex in a sample, the method comprising:
(a) contacting the sample with a coelenterazine substrate and the compound of claim 1; and
(b) detecting luminescence in the sample,
wherein the compound of claim 1 causes a decrease in the luminescence from the bioluminescent complex.

8. A method to detect an interaction or co-localization between a first molecule and a second molecule in a sample, the method comprising:
(a) contacting a sample with a coelenterazine substrate and the compound of claim 1, wherein the sample comprises:
(i) a first fusion, wherein the first fusion comprises a non-luminescent peptide or polypeptide of an *Oplophorus*-derived luciferase and a first molecule; and
(ii) a second fusion, wherein the second fusion comprises a non-luminescent complementary polypeptide or peptide of an *Oplophorus*-derived luciferase and a second molecule, wherein the non-luminescent polypeptide is capable of forming a bioluminescent complex with the non-luminescent peptide; and
(b) detecting luminescence in the sample,
wherein the detection of luminescence indicates an interaction or co-localization between the first molecule and the second molecule.

9. A method to detect an interaction or co-localization of a first molecule and a second molecule in a sample, the method comprising:
(a) contacting a sample with a non-luminescent polypeptide or peptide of an *Oplophorus*-derived luciferase, a coelenterazine substrate, and the compound of claim 1, wherein the sample comprises:
(i) a first polynucleotide encoding a first fusion, wherein the first fusion comprises an non-luminescent complementary peptide or polypeptide of an *Oplophorus*-derived luciferase and a first molecule, wherein the non-luminescent complementary peptide or polypeptide is capable of forming a bioluminescent complex with the non-luminescent polypeptide or peptide; and
(ii) a second polynucleotide encoding a second fusion, wherein the second fusion comprises a fluorescent acceptor molecule and a second molecule; and
(b) detecting bioluminescence resonance energy transfer (BRET) in the sample indicating an interaction or co-localization of the first molecule and the second molecule.

10. A method to detect interaction or co-localization of molecules in a sample, the method comprising:
(a) contacting a sample with a coelenterazine substrate and the compound of claim 1, wherein the sample comprises:
(i) a first fusion comprising a non-luminescent polypeptide of an *Oplophorus*-derived luciferase and a first molecule;

(ii) a second fusion comprising a non-luminescent peptide of an *Oplophorus*-derived luciferase and a second molecule, wherein the non-luminescent peptide is capable of forming a bioluminescent complex with the non-luminescent polypeptide; and (iii) a third fusion comprising a fluorescent acceptor molecule and a third molecule; and (b) detecting bioluminescence resonance energy transfer (BRET) in the sample, indicating an interaction or co-localization between the first molecule, second molecule, and third molecule in the sample.

11. A method to detect a molecule of interest in a sample, the method comprising:
(a) contacting a sample comprising the molecule of interest fused to a non-luminescent peptide or polypeptide of an *Oplophorus*-derived luciferase with
(i) a coelenterazine substrate;
(ii) the compound of claim 1; and
(iii) a non-luminescent complementary polypeptide or peptide of an *Oplophorus*-derived luciferase, wherein the non-luminescent complementary polypeptide or peptide is capable of forming a bioluminescent complex with the non-luminescent peptide or polypeptide; and
(b) detecting luminescence in the sample, wherein detection of luminescence indicates formation of a bioluminescent complex between the non-luminescent peptide and the non-luminescent polypeptide.

12. A method to detect a molecule of interest in a sample, the method comprising:
(a) contacting a sample comprising the molecule of interest fused to a non-luminescent peptide or polypeptide of an *Oplophorus*-derived luciferase with
(i) a coelenterazine substrate;
(ii) a compound of claim 1; and
(iii) a fusion comprising a non-luminescent complementary polypeptide or peptide of an *Oplophorus*-derived luciferase and a fluorescent moiety, wherein the non-luminescent complementary polypeptide or peptide is capable of forming a bioluminescent complex with the non-luminescent peptide or polypeptide; and
(b) detecting bioluminescence resonance energy transfer (BRET) in the sample, indicating detection of the molecule.

13. A bioluminescence resonance energy transfer (BRET) system comprising:
(a) a first fusion comprising a non-luminescent peptide or polypeptide of an *Oplophorus*-derived luciferase and a first molecule;
(b) a second fusion comprising a non-luminescent complementary polypeptide or peptide of an *Oplophorus*-derived luciferase and a fluorescent moiety, wherein the non-luminescent complementary polypeptide or peptide is capable of forming a bioluminescent complex with the non-luminescent peptide or polypeptide;
(c) a coelenterazine substrate; and
(d) the compound of claim 1.

14. A bioluminescence resonance energy transfer (BRET) system comprising:
(a) a first fusion comprising a first molecule and a non-luminescent peptide or polypeptide of an *Oplophorus*-derived luciferase;
(b) a second fusion comprising a second molecule and a fluorescent acceptor molecule;
(c) a non-luminescent complementary polypeptide or peptide of *Oplophorus*-derived luciferase capable of forming a bioluminescent complex with the non-luminescent peptide or polypeptide of an *Oplophorus*-derived luciferase;
(d) a coelenterazine substrate; and
(e) the compound of claim 1.

15. A kit comprising:
(a) the compound of claim 1; and
(b) an *Oplophorus* luciferase-derived bioluminescent complex.

16. The kit of claim 15, wherein the *Oplophorus* luciferase-derived bioluminescent complex comprises:
(a) a non-luminescent peptide comprising an amino acid sequence having less than 100% and greater than 40% sequence identity with SEQ ID NO: 2; and
(b) a non-luminescent polypeptide comprising an amino acid sequence having less than 100% and greater than 40% sequence identity with SEQ ID NO: 3.

17. A kit comprising:
(a) the compound of claim 1; and
(b) a first polynucleotide encoding a non-luminescent peptide of an *Oplophorus*-derived luciferase; and
(c) a second polynucleotide encoding a non-luminescent polypeptide of an *Oplophorus*-derived luciferase, wherein the non-luminescent polypeptide is capable of forming a bioluminescent complex with the non-luminescent peptide.

18. The kit of claim 17, wherein the non-luminescent peptide comprises an amino acid sequence having less than 100% and greater than 40% sequence identity with SEQ ID NO: 2; and the non-luminescent polypeptide comprises an amino acid sequence having less than 100% and greater than 40% sequence identity with SEQ ID NO: 3.

19. The kit of claim 15, further comprising a coelenterazine substrate.

20. The kit of claim 17, further comprising a coelenterazine substrate.

* * * * *

SEQUENCE LISTING

<160> NUMBER OF SEQ ID NOS: 7

<210> SEQ ID NO 1
<211> LENGTH: 169
<212> TYPE: PRT
<213> ORGANISM: Oplophorus gracilirostris

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
            35                  40                  45

Glu Asn Gly Leu Lys Ala Asp Ile His Val Ile Ile Pro Tyr Glu Gly
50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
                100                 105                 110

Pro Tyr Pro Gly Ile Ala Val Phe Asp Gly Lys Gln Ile Thr Val Thr
            115                 120                 125

Gly Thr Leu Trp Asn Gly Asn Lys Ile Tyr Asp Glu Arg Leu Ile Asn
            130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 14
<212> TYPE: PRT
<213> ORGANISM: Artificial sequence
<220> FEATURE:
<223> OTHER INFORMATION: Synthetic

<400> SEQUENCE: 2

Met Gly Val Thr Gly Trp Arg Leu Cys Glu Arg Ile Leu Ala
1               5                   10

<210> SEQ ID NO 3
<211> LENGTH: 159
<212> TYPE: PRT
<213> ORGANISM: Artificial sequence
<220> FEATURE:
<223> OTHER INFORMATION: Synthetic

<400> SEQUENCE: 3

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
            35                  40                  45

Ser Gly Glu Asn Gly Leu Lys Ile Asp Ile His Val Ile Ile Pro Tyr
50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
            115                 120                 125

```
Val Thr Gly Thr Leu Trp Asn Gly Asn Lys Ile Ile Asp Glu Arg Leu
        130                 135                 140

Ile Asn Pro Asp Gly Ser Leu Leu Phe Arg Val Thr Ile Asn Val
145                 150                 155
```

<210> SEQ ID NO 4
<211> LENGTH: 11
<212> TYPE: PRT
<213> ORGANISM: Artificial sequence
<220> FEATURE:
<223> OTHER INFORMATION: Synthetic

<400> SEQUENCE: 4

```
Val Ser Gly Trp Arg Leu Phe Lys Lys Ile Ser
1               5                   10
```

<210> SEQ ID NO 5
<211> LENGTH: 159
<212> TYPE: PRT
<213> ORGANISM: Artificial sequence
<220> FEATURE:
<223> OTHER INFORMATION: Synthetic

<400> SEQUENCE: 5

```
Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser
145                 150                 155
```

<210> SEQ ID NO 6
<211> LENGTH: 11
<212> TYPE: PRT
<213> ORGANISM: Artificial sequence
<220> FEATURE:
<223> OTHER INFORMATION: Synthetic

<400> SEQUENCE: 6

```
Val Thr Gly Tyr Arg Leu Phe Glu Glu Ile Leu
1               5                   10
```

<210> SEQ ID NO 7
<211> LENGTH: 171
<212> TYPE: PRT
<213> ORGANISM: Artificial sequence
<220> FEATURE:

<223> OTHER INFORMATION: Synthetic

<400> SEQUENCE: 7

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```